US011730794B2

(12) United States Patent
Yancopoulos

(10) Patent No.: US 11,730,794 B2
(45) Date of Patent: *Aug. 22, 2023

(54) USE OF A VEGF ANTAGONIST TO TREAT ANGIOGENIC EYE DISORDERS

(71) Applicant: REGENERON PHARMACEUTICALS, INC., Tarrytown, NY (US)

(72) Inventor: George Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 212 days.

This patent is subject to a terminal disclaimer.

(21) Appl. No.: 17/112,404

(22) Filed: Dec. 4, 2020

(65) Prior Publication Data

US 2021/0085753 A1  Mar. 25, 2021

Related U.S. Application Data

(63) Continuation of application No. 17/072,417, filed on Oct. 16, 2020, which is a continuation of application No. 16/397,267, filed on Apr. 29, 2019, now Pat. No. 10,888,601, which is a continuation of application No. 16/159,282, filed on Oct. 12, 2018, now Pat. No. 10,828,345, which is a continuation of application No. 15/471,506, filed on Mar. 28, 2017, now Pat. No. 10,130,681, which is a continuation of application No. 14/972,560, filed on Dec. 17, 2015, now Pat. No. 9,669,069, which is a continuation of application No. 13/940,370, filed on Jul. 12, 2013, now Pat. No. 9,254,338, which is a continuation-in-part of application No. PCT/US2012/020855, filed on Jan. 11, 2012.

(60) Provisional application No. 61/432,245, filed on Jan. 13, 2011, provisional application No. 61/434,836, filed on Jan. 21, 2011, provisional application No. 61/561,957, filed on Nov. 21, 2011.

(51) Int. Cl.
| | |
|---|---|
| *A61K 38/17* | (2006.01) |
| *C07K 14/71* | (2006.01) |
| *C07K 19/00* | (2006.01) |
| *C07K 16/22* | (2006.01) |
| *A61K 9/00* | (2006.01) |
| *A61K 39/00* | (2006.01) |

(52) U.S. Cl.
CPC .......... *A61K 38/179* (2013.01); *A61K 9/0048* (2013.01); *C07K 14/71* (2013.01); *C07K 16/22* (2013.01); *A61K 2039/505* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | |
|---|---|---|
| 6,171,586 B1 | 1/2001 | Lam et al. |
| 6,833,349 B2 | 12/2004 | Xia et al. |
| 6,879,294 B2 | 5/2005 | Davis-Smyth et al. |
| 6,897,294 B2 | 5/2005 | Davis-Smyth et al. |
| 7,070,959 B1 | 7/2006 | Papadopoulos |
| 7,087,411 B2 | 8/2006 | Daly et al. |
| 7,300,563 B2 | 11/2007 | Diaddario, Jr. |
| 7,300,653 B2 | 11/2007 | Wiegand et al. |
| 7,303,746 B2 | 12/2007 | Wiegand |
| 7,303,747 B2 | 12/2007 | Wiegand et al. |
| 7,303,748 B2 | 12/2007 | Wiegand |
| 7,306,799 B2 | 12/2007 | Wiegand |
| 7,374,757 B2 | 5/2008 | Papadopoulos et al. |
| 7,374,758 B2 | 5/2008 | Papadopoulos et al. |
| 7,378,095 B2 | 5/2008 | Cao et al. |
| 7,396,664 B2 | 7/2008 | Daly et al. |
| 7,482,002 B2 | 1/2009 | Cedarbaum |
| 7,521,049 B2 | 4/2009 | Wiegand et al. |
| 7,531,173 B2 | 5/2009 | Wiegand et al. |
| 7,608,261 B2 | 10/2009 | Furfine et al. |
| 7,750,138 B2 | 7/2010 | Fang et al. |
| 7,951,585 B2 | 5/2011 | Ke |
| 7,972,598 B2 | 7/2011 | Daly et al. |
| 8,029,791 B2 | 10/2011 | Papadopoulos et al. |
| 8,092,803 B2 | 1/2012 | Furfine et al. |

(Continued)

FOREIGN PATENT DOCUMENTS

| | | |
|---|---|---|
| CN | 1304427 C | 3/2007 |
| CN | 100502945 C | 6/2009 |

(Continued)

OTHER PUBLICATIONS

Eylea®, Highlights of Prescribing Information, Revised Nov. 2011.

(Continued)

*Primary Examiner* — Christine J Saoud
*Assistant Examiner* — Jon M Lockard
(74) *Attorney, Agent, or Firm* — Arnold & Porter Kaye Scholer LLP

(57) ABSTRACT

The present invention provides methods for treating angiogenic eye disorders by sequentially administering multiple doses of a VEGF antagonist to a patient. The methods of the present invention include the administration of multiple doses of a VEGF antagonist to a patient at a frequency of once every 8 or more weeks. The methods of the present invention are useful for the treatment of angiogenic eye disorders such as age related macular degeneration, diabetic retinopathy, diabetic macular edema, central retinal vein occlusion, branch retinal vein occlusion, and corneal neovascularization.

41 Claims, 1 Drawing Sheet

Specification includes a Sequence Listing.

(56) References Cited

U.S. PATENT DOCUMENTS

| | | |
|---|---|---|
| 8,216,575 B2 | 7/2012 | Yu |
| 8,343,737 B2 | 1/2013 | Papadopoulos et al. |
| 8,647,842 B2 | 2/2014 | Papadopoulos et al. |
| 9,254,338 B2 | 2/2016 | Yancopoulos |
| 9,657,084 B2 | 5/2017 | Ke et al. |
| 9,669,069 B2 | 6/2017 | Yancopoulos |
| 10,130,681 B2 | 11/2018 | Yancopoulos |
| 10,406,226 B2 | 9/2019 | Dix et al. |
| 10,464,992 B2 | 11/2019 | Furfine et al. |
| 10,828,345 B2 | 11/2020 | Yancopoulos |
| 10,857,205 B2 | 12/2020 | Yancopoulos |
| 10,888,601 B2 | 1/2021 | Yancopoulos |
| 11,066,458 B2 | 7/2021 | Furfine et al. |
| 11,084,865 B2 | 8/2021 | Furfine et al. |
| 11,253,572 B2 | 2/2022 | Yancopoulos |
| 2003/0113316 A1 | 6/2003 | Kaisheva et al. |
| 2003/0138417 A1 | 7/2003 | Kaisheva et al. |
| 2003/0171320 A1 | 9/2003 | Guyer |
| 2004/0197324 A1 | 10/2004 | Liu et al. |
| 2004/0213787 A1 | 10/2004 | Sleeman et al. |
| 2004/0266688 A1 | 12/2004 | Nayak |
| 2005/0032699 A1 | 2/2005 | Holash et al. |
| 2005/0163798 A1 | 7/2005 | Papadopoulos et al. |
| 2005/0260203 A1 | 11/2005 | Wiegand et al. |
| 2005/0281822 A1 | 12/2005 | Cedarbaum et al. |
| 2006/0030000 A1 | 2/2006 | Alitalo et al. |
| 2006/0058234 A1 | 3/2006 | Daly et al. |
| 2006/0172944 A1 | 8/2006 | Wiegand et al. |
| 2006/0217311 A1 | 9/2006 | Dix et al. |
| 2007/0190058 A1 | 8/2007 | Shams |
| 2008/0220004 A1 | 9/2008 | Wiegand et al. |
| 2009/0264358 A1 | 10/2009 | Yu |
| 2010/0160233 A1 | 6/2010 | Bissery et al. |
| 2013/0295094 A1 | 11/2013 | Yancopoulos |
| 2016/0130337 A1 | 5/2016 | Gekkieva et al. |
| 2019/0290725 A1 | 9/2019 | Vitti et al. |
| 2019/0388539 A1 | 12/2019 | Dix et al. |
| 2020/0017572 A1 | 1/2020 | Furfine et al. |

FOREIGN PATENT DOCUMENTS

| | | |
|---|---|---|
| CN | 100567325 C | 12/2009 |
| CN | 102233132 B | 10/2013 |
| CN | 102380096 B | 4/2014 |
| CN | 103212075 B | 6/2017 |
| CN | 107115294 A | 9/2017 |
| EP | 2663325 | 11/2013 |
| EP | 3222285 A1 | 9/2017 |
| JP | 2010-509369 | 3/2010 |
| WO | 97/04801 | 2/1997 |
| WO | WO 97/04801 | 2/1997 |
| WO | WO 2000/75319 | 12/2000 |
| WO | WO 2004/106378 A2 | 12/2004 |
| WO | WO 2005/000895 A2 | 1/2005 |
| WO | WO 2006/047325 | 3/2006 |
| WO | WO 2007/022101 A2 | 2/2007 |
| WO | WO 2008/063932 | 5/2008 |
| WO | WO 2012/097019 | 7/2012 |

OTHER PUBLICATIONS

IPR2021-00880, Paper 1, Petition for IPR (May 5, 2021).
IPR2021-00880, Exhibit 1002, Albini Declaration (May 4, 2021).
IPR2021-00880, Exhibit 1003, Gerritsen Declaration (Apr. 30, 2021).
IPR2021-00880, Paper 10, Preliminary Response of Patent Owner (Aug. 16, 2021).
IPR2021-00881, Paper 1, Petition for IPR (May 5, 2021).
IPR2021-00881, Exhibit 1002, Albini Declaration (May 4, 2021).
IPR2021-00881, Exhibit 1003, Gerritsen Declaration (Apr. 26, 2021).
IPR2021-00881, Paper 10, Preliminary Response of Patent Owner (Aug. 16, 2021).
IPR2021-00881, Exhibit 2001, Do Declaration (Aug. 13, 2021).
Mitchell et al., "Evaluating the Impact of Intravitreal Aflibercept on Diabetic Retinopathy Progression in the VIVID-DME and VISTA-DME Studies" Ophthalmol Retina 2(10):988-96 (2018).
PGR2021-00035, Paper 2, Petition for PGR (Jan. 7, 2021).
PGR2021-00035, Paper 6, Preliminary Response of Patent Owner (Apr. 15, 2021).
PGR2021-00035, Exhibit 1003 Wu Declaration (Jan. 7, 2021).
PGR2021-00035, Exhibit 2001 Do Declaration (Apr. 14, 2021).
PGR2021-00035, Exhibit 2002 D. Brown Declaration (Apr. 14, 2021).
Cao, J. R., R.; Wang, Q.; Yancopoulos, G.D.; Wiegand, S.J. (2002). Inhibition of Corneal Neovascularization and Inflammation by VEGF Trap. In "ARVO", Invest. Ophthalmol. Vis. Sci. vol. 43. E-Abstract 1863.
Wang, Q. R., R.; Cao, J.; Yancopoulos, G.D.; and Wiegand, S.J. (2002). Anti-Angiogenic Properties of a New VEGF Antagonist, VEGF Trap, in a Mouse Model of Retinal Neovascularization. In "ARVO", Invest. Ophthalmol. Vis. Sci., vol. 43. E-Abstract. 3714.
Saishin, Y., Saishin, Y., Takahashi, K., Lima e Silva, R., et al. (2003). VEGF-TRAP(R1R2) suppresses choroidal neovascularization and VEGF-induced breakdown of the blood-retinal barrier. J Cell Physiol 195:241-48.
Cursiefen, C., Cao, J., Chen, L., Liu, Y., Maruyama, K., et al. (2004). Inhibition of hemangiogenesis and lymphangiogenesis after normal-risk corneal transplantation by neutralizing VEGF promotes graft survival. Invest Ophthalmol Vis Sci 45(8):2666-73.
Cursiefen, C., Chen, L., Borges, L. P., Jackson, D., Cao, J., et al. (2004). VEGF-A stimulates lymphangiogenesis and hemangiogenesis in inflammatory neovascularization via macrophage recruitment. J Clin Invest 113(7):1040-50.
Cao, J.; Song, H.; Renard, R.A.; Liu, Y.; Yancopolous, G.D.; Wiegand, S.J. (2005). Systemic Administration of VEGF Trap Suppresses Vascular Leak and Leukostasis in the Retinas of Diabetic Rats. In "ARVO", vol. 46. Invest. Ophthalmol. Vis. Sci. E-Abstract 446.
Nork, T. M., Dubielzig, R. R., Christian, B. J., Miller, P. E., Miller, J. M., et al. (2011). Prevention of experimental choroidal neovascularization and resolution of active lesions by VEGF trap in nonhuman primates. Arch Ophthalmol 129(8):1042-52.
U.S. Appl. No. 16/055,847—Third Party Submissions dated May 1, 2019.
U.S. Appl. No. 16/159,282—Third Party Submissions dated May 31, 2019.
ADSIS R&D Profile "Aflibercept: AVE 0005, AVE 005, AVE0005, VEGF Trap—Regeneron, VEGF Trap (R1R2), VEGF Trap-Eye." Drugs R D, 9(4):261-269 (2008).
Anonymous "Lucentis (rangibizymab injection) Intravitreal Injection" pp. 103 (Jun. 2006).
Anonymous "Anti-VEGF 2019: The State of the Art" Review of Ophthalmology (published Aug. 5, 2019).
Barbazetto, "Dosing Regimen and the Frequency of Macular Hemorrhagesi In Neovascular Age-Related Macular Degeneration Treated With Ranibizumab." Retina, 30(9):1376-85 (2010).
Bayer Investor News, "Bayer and Regeneron Start additional Phase 3 Study for VEGF Trap-Eye in Wet Age-related Macular Degeneration." (May 8, 2008).
Bayer Investor News, "VEGF Trap-Eye: New Data Confirm Successes in the Treatment of Age-related Macular Degeneration" (Sep. 28, 2008).
Benz et al. "Clear-It-2: Interim Results of the Phase II, Randomized, Controlled Dose- and Interval-ranging Study of Repeated Intravitreal VEGF Trap Administration in Patients With Neovascular Age-related Macular Degeneration (AMD)" ARVO Annual Meeting Abstract (May 2007).
Boyer, "A Phase IIIb Study to Evaluate the Safety of Ranibizumab in Subjects with Neovascular Age-related Macular Degeneration." Ophthalmology, 116(9):1731-39 (Sep. 2009).
Brown, "Ranibizumab versus Verteporfin for Neovascular Age-Related Macular Degeneration." N Engl J Med, 355(14):1432-44 (Oct. 5, 2006).

(56) References Cited

OTHER PUBLICATIONS

Brown, "Primary Endpoint Results of a Phase II Study of Vascular Endothelial Growth Factor Trap-Eye in Wet Age-related Macular Degeneration." Ophthalmology, 118(6):1089-97 (Jun. 2011).
Brown, "Long-term Outcomes of Ranibizumab Therapy for Diabetic Macular Edema: The 36-Month Results from Two phase III Trials." Ophthalmology, 120(10):2013-22 (Oct. 2013).
Browning et al. "Aflibercept for age-related macular degeneration: a game-changer or quiet addition?" American Journal of Ophthalmology, 154(2):222-226 (Aug. 2012).
Campochiaro et al. "Ranibizumab for Macular Edema Due to Retinal Vein Occlusions Implication of VEGF as a Critical Stimulator" Molecular Therapy, 16(4):791-799 (2008).
Campochiaro, "Ranibizumab for Macular Edema following Branch Retinal Vein Occlusion: six-month primary end point results of a phase III study." Ophthalmology, 117(6):1102-1112 (Jun. 2010).
Campochiaro, "Sustained Benefits from Ranibizumab for Macular Edema following Central Retinal Vein Occlusion: Twelve-Month Outcomes of a phase III Study." Ophthalmology, 188(10):2041-49 (Oct. 2011).
Cao, "A Subretinal Matrigel Rat Choroidal Neovascularization (CNV) Model and Inhibition of CNV and Associated Inflammation and Fibrosis by VEGF Trap" Investigative Ophthalmology & Visual Science, 51(11):6009-6017 (Nov. 2010).
Center for Drug Evaluation and Research Application No. 21-756 Medical Review(s) (Dec. 17, 2004) <URL:https://www.accessdata.fda.gov/drugsatfda_docs/nda/2004/21-756_Macugen_medr.pdf>.
Center for Drug Evaluation and Research BLA Application No. 125156 Medical Review, (Jun. 2006) <URL:https://www.accessdata.fda.gov/drugsatfda_docs/nda/2006/125156s000_Lucentis_MedR.pdf>.
Charles, Steve (Guest Lecturer) "VEGF Trap Has Positive DME Data" Tenth Annual Retina Fellows Forum Jan. 29 and 30, Chicago, (Article Date Mar. 1, 2010).
Chatziralli et al. "Intravitreal aflibercept for neovascular age-related macular degeneration in patients aged 90 years or older: 2-year visual acuity outcomes" Eye (2018) 32:1523-1529.
Chung et al. "Ziv-aflibercept: A novel angiogenesis inhibitor for the treatment of metastatic colorectal cancer" Am J Heath-Syst Pharm (Nov. 1, 2013) 70:1887-1896.
Cooper et al., "Increased Renal Expression of Vascular Endothelial Growth Factor (VEGF) and Its Receptor VEGFR-2 in Experimental Diabetes" Diabetes (1999) 48:2229-2239.
Croll et al., "VEGF-mediated inflammation precedes angiogenesis in adult brain" Experimental Neurology (2004) 187:388-402.
Csaky, "Safety Implications of Vascular Endothelial Growth Factor Blockade for Subjects Receiving Intravitreal Anti-Vascular Endothelial Growth Factor Therapies." Am. J. Ophthalmology, 148(5):647-56, (Nov. 2009).
DeVriese et al., "Antibodies against Vascular Endothelial Growth Factor Improve Early Renal Dysfunction in Experimental Diabetes" J. Am. Soc. Nephrol (2001) 12:993-1000.
Dixon et al., "VEGF Trap-Eye for the treatment of neovascular age-related macular degeneration" Expert Opin. Investig. Drugs, 18(10):1573-1580 (2009).
Do et al., "An exploratory study of the safety, tolerability and bioactivity of a single intravitreal injection of vascular endothelial growth factor Trap-Eye in patients with diabetic macular oedema" Br J Ophthalmol. 93(2):144-1449 (Feb. 2009).
Do et al., "The Ds Vinci Study: phase 2 primary results of VEGF Trap-Eye in patients with diabetic macular edema" Ophthalmology, 118(9):1819-1826 (Sep. 2011).
Do, "One-Year Outcomes of the Da Vinci Study of VEGF Trap-Eye in Eyes with Diabetic Macular Edema." Ophthalmology, 119(8):1658-65 (2012).
Do et al. "Results of a Phase 1 Study of Intravitreal VEGF Trap in Subjects with Diabetic Macular Edema: The Clear-It DME Study" ARVO Annual Meeting Abstract (May 2007).
Do et al. "VEGF Trap-Eye Vision-specific Quality of Life through 52 Weeks in Patients with Neovascular AMD in Clear-It 2: A Phase 2 Clinical Trial" ARVO Annual Meeting Abstract (Apr. 2009).
Eichten, "Rapid decrease in tumor perfusion following VEGF blockade predicts long-term tumor growth inhibition in preclinical tumor models" Angiogenesis, 16:429-441 (2013).
Engelbert, "Treat and Extend Dosing of Intravitreal Antivascular Endothelial Growth Factor Therapy for Type 3 Neovascularization/ Retinal Angiomatous Proliferation." Retina, 29(10):1424-31 (2009).
Engelbert, "Long-Term Follow-Up for Type 1 (Subretinal Pigment Epithelium) Neovascularization Using a Modified 'Treat and Extend' Dosing Regiment of Intravitreal Antivascular Endothelial Growth Factor Therapy." Retina, 30(9):1368-75 (2010).
Engelbert, "The 'Treat and Extend' Dosing Regimen of Intravitreal Anti-Vascular Endothelial Growth Factor Therapy for Neovascular Age-Related Macular Degeneration." Ophthalmology Management, Issue 42, (Jun. 2010) available at http://www.visioncareprofessional.com/emails/amdupdate/index.asp?issue=42.
Eremina et al., "Glomerular-specific alterations of VEGF-A expression lead to distinct congenital and acquired renal diseases" Journal of Clinical Investigation (Mar. 2003) 111(5):707-716.
Eriksson et al., "Structure, Expression and Receptor-Binding Properties of Novel Vascular Endothelial Growth Factors" Vascular Growth Factors and Angiogenesis, Springer (1999) pp. 41-57.
The Eyetech Study Group, "Anti-Vascular Endothelial Growth Factor Therapy for Subfoveal Choroidal Neovascularization Secondary to Age-related Macular Degeneration" American Academy of Ophthalmology, 110(5):979-986 (May 2003).
Eylea®, Highlights of Prescribing Information, Revised Aug. 2018.
Ferrara, N. "Vascular Endothelial Growth Factor: Molecular and Biological Aspects" Advances in Organ Biology (1999) pp. 1-30.
Ferrara et al., "Clinical applications of angiogenic growth factors and their inhibitors" Nature Medicine (Dec. 1999) 5(12):1359-1364.
Flyvbjerg et al., "Amelioration of Long-Term Renal Changes in Obese Type 2 Diabetic Mice by a Neutralizing Vascular Endothelial Growth Factor Antibody" Diabetes (Oct. 2002) 51:3090-3094.
Fung, "An Optical Coherence Tomography-Guided, Variable Dosing Regiment with Intravitreal Ranibizumab (Lucentis) for Neovascular Age-related Macular Degeneration." Am J Ophthalmology, 143(4):566-83 (Apr. 2007).
Gale, "Complementary and Coordinated Roles of the VEGFs and Angiopoietins during Normal and Pathologic Vascular Formation." Cold Spring Harbor Symposia on Quantitative Biology, vol. LXVII, pp. 267-273 (2002).
Garcia-Quintanilla, "Pharmacokinetics of Intravitreal Anti-VEGF Drugs in Age-Related Macular Degeneration." Pharmaceutics, 11:365 (2019).
Gomez-Manzano, "VEGF Trap induces antiglioma effect at different stages of disease." Neuro-Oncology, 10:940-945 (Dec. 2008).
Gragoudas, "Pegaptanib for Neovascular Age-Related Macular Degeneration." N Engl J Med, 351(27):2805-16, (Dec. 30, 2004).
Gutierrez et al., "Intravitreal bevacizumab (Avastin) in the treatment of macular edema secondary to retinal vein occlusion" Clin. Ophthalmol., 2(4):787,791 (2008).
Haller et al., "VEGF Trap-Eye in CRVO: Primary Endpoint Results of the Phase 3 COPERNICUS Study" ARVO Annual Meeting Abstract (Apr. 2011).
Heier et al., "Clear-It 2: Phase 2, Randomized Controlled Dose and Interval-Ranging Study of Intravitreal VEFG Trap Eye in Patients with Neovascular Age-Related Macular Degeneration: Predictive Factors for Visual Acuity" ARVO Annual Meeting Abstract (Apr. 2009).
Heier et al., "rhuFab V2 (anti-VEGF Antibody) for Treatment of Exudative AMD" Symposium 8:Experimental and Emerging Treatments for Choroidal Neovascularization, 10 pp (2002).
Heier et al., "RhuFab V2 in Wet AMD—6 Month Continued Improvement Following Multiple Intravitreal Injections" Invest Ophthalmol Vis Sci, 44(E-Abstract):972 (2003).
Heier et al., "Intravitreal Aflibercept (VEGF Trap-Eye) in Wet Age-related macular Degeneration," Ophthalmology, 119:2537-2548 (2012).

(56) References Cited

OTHER PUBLICATIONS

Heier, "Intravitreal Aflibercept for Diabetic Macular Edema: 148-Week Results from the VISTA and VIVID Studies." Ophthalmology, 123(11):2376-2385 (Nov. 2016).
Heier et al., "The 1-year Results of Clear-It 2, a Phase 2 Study of Vascular Endothelial Growth Factor Trap-Eye Dosed As-needed After 12-week Fixed Dosing" Ophthalmology 2011;118:1098-1106 (Jun. 2011).
Heier et al., "The 1-year Results of Clear-It 2, a Phase 2 Study of Vascular Endothelial Growth Factor Trap-Eye Dosed As-needed After 12-week Fixed Dosing: Erratum" Ophthalmology 2011;118:1700 (Sep. 2011).
Ho, "VEGF Trap-Eye in Wet AMD—Clear-It 2: One-Year OCT and FA Outcomes" CLEAR-IT 2 Study Group, pp. 1-24 (Sep. 28, 2008).
Ho et al., Slides entitled Clear It 2 One-Year Key Results, Retina Society (2008).
Holash et al., "Vessel Cooption, Regression, and Growth in Tumors Mediated by Angiopoietins and VEGF" Science (Jun. 18, 1999) 284(5422):1994-1998.
Holash, "VEGF-Trap: A VEGF blocker with potent antitumor effects" PNAS 99(17)11393-11398 (Aug. 20, 2002).
Holash, "Inhibitors of growth factor receptors, signaling pathways and angiogenesis as therapeutic molecular agents." Cancer Metastasis 25:243-252 (2006).
Information from ClinicalTrials.gov archive History of Changes for Study: NCT00320775 "Safety and Tolerability of Intravitreal Administration of VEGF Trap in Patients With Neovascular Age-Related Macular Degeneration" 70 pages, Latest version submitted Jun. 8, 2011 on ClinicalTrials.gov (NCT00320775_2006-2011).
Information from ClinicalTrials.gov archive History of Changes for Study: NCT00320775 "Safety and Tolerability of Intravitreal Administration of VEGF Trap in Patients With Neovascular Age-Related Macular Degeneration" 10 pages, Latest version submitted Mar. 16, 2015 on ClinicalTrials.gov (NCT00320775_2015).
Information from ClinicalTrials.gov archive History of Changes for Study: NCT00320788 "Safety and Efficacy of Repeated Intravitreal Administration of Vascular Endothelial Growth Factor (VEGF) Trap in Patients With Wet Age-Related Macular Degeneration (AMD)" 71 pages, Latest version submitted Dec. 1, 2011 on ClinicalTrials.gov (NCT00320788_2006-2011).
Information from ClinicalTrials.gov archive History of Changes for Study: NCT00320788 "Safety and Efficacy of Repeated Intravitreal Administration of Vascular Endothelial Growth Factor (VEGF) Trap in Patients With Wet Age-Related Macular Degeneration (AMD)" 31 pages, Latest version submitted Jan. 27, 2012 on ClinicalTrials.gov (NCT00320788_2012).
Information from ClinicalTrials.gov archive History of Changes for Study: NCT00320814 "Phase 1 Study of VEGF Trap in Patients With Diabetic Macular Edema" 30 pages, Latest version submitted Jun. 8, 2011 on ClinicalTrials.gov (NCT00320814_2006-2011).
Information from ClinicalTrials.gov archive History of Changes for Study: NCT00509795 "Double-Masked Study of Efficacy and Safety of IVT VEGF Trap-Eye in Subjects With Wet AMD (View 1)" 318 pages, Latest version submitted Dec. 1, 2011 on ClinicalTrials.gov (NCT00509795_2007-2011).
Information from ClinicalTrials.gov archive History of Changes for Study: NCT00509795 "Double-Masked Study of Efficacy and Safety of IVT VEGF Trap-Eye in Subjects With Wet AMD (View 1)" 200 pages, Latest version submitted Dec. 20, 2012 on ClinicalTrials.gov (NCT00509795_2012).
Information from ClinicalTrials.gov archive History of Changes for Study: NCT00527423 "Randomized, Single-Masked, Long-Term, Safety and Tolerability Study of VEGF Trap-Eye in AMD" 64 pages, Latest version submitted Nov. 1, 2011 on ClinicalTrials.gov (NCT00527423_2007-2011).
Information from ClinicalTrials.gov archive History of Changes for Study: NCT00527423 "Randomized, Single-Masked, Long-Term, Safety and Tolerability Study of VEGF Trap-Eye in AMD" 42 pages, Latest version submitted Jun. 10, 2013 on ClinicalTrials.gov (NCT00527423_2012-2013).
Information from ClinicalTrials.gov archive History of Changes for Study: NCT00637377 "Vascular Endothelial Growth Factor (VEGF) Trap-Eye: Investigation of Efficacy and Safety in Wet Age-Related Macular Degeneration (AMD) (View 2)" 667 pages, Latest version submitted Dec. 16, 2011 on ClinicalTrials.gov (NCT00637377_2008-2011).
Information from ClinicalTrials.gov archive History of Changes for Study: NCT00637377 "Vascular Endothelial Growth Factor (VEGF) Trap-Eye: Investigation of Efficacy and Safety in Wet Age-Related Macular Degeneration (AMD) (View 2)" 289 pages, Latest version submitted Nov. 28, 2014 on ClinicalTrials.gov (NCT00637377_2012-2014).
Information from ClinicalTrials.gov archive History of Changes for Study: NCT00789477 "DME and VEGF Trap-Eye [Intravitreal Aflibercept Injection (IAI;EYLEA®;BAY86-5321)] INvestigation of Clinical Impact (Da Vinci)" 135 pages, Latest version submitted May 2, 2011 on ClinicalTrials.gov (NCT00789477_2008-2011).
Information from ClinicalTrials.gov archive History of Changes for Study: NCT00789477 "DME and VEGF Trap-Eye [Intravitreal Aflibercept Injection (IAI;EYLEA®;BAY86-5321)] INvestigation of Clinical Impact (Da Vinci)" 53 pages, Latest version submitted Aug. 28, 2014 on ClinicalTrials.gov (NCT00789477_2013-2014).
Information from ClinicalTrials.gov archive History of Changes for Study: NCT00943072 "Vascular Endothelial Growth Factor (VEGF) Trap-Eye: Investigation of Efficacy and Safety in Central Retinal Vein Occlusion (CRVO)" 98 pages, Latest version submitted May 9, 2011 on ClinicalTrials.gov (NCT00943072_2009-2011).
Information from ClinicalTrials.gov archive History of Changes for Study: NCT00943072 "Vascular Endothelial Growth Factor (VEGF) Trap-Eye: Investigation of Efficacy and Safety in Central Retinal Vein Occlusion (CRVO)" 64 pages, Latest version submitted Apr. 16, 2013 on ClinicalTrials.gov (NCT00943072_2012-2013).
Information from ClinicalTrials.gov archive View of NCT00637377 "Vascular Endothelial Growth Factor (VEGF) Trap-Eye: Investigation of Efficacy and Safety in Wet Age-Related Macular Degeneration (AMD) (View 2)" ClinicalTrials.gov. Web. (Nov. 30, 2010).
Information from ClinicalTrials.gov archive on the VIEW 2 study (NCT00637377) "VEGF Trap-Eye: Investigation of Efficacy and Safety in Wet AMD (View 2)" version available (updated on Mar. 17, 2008).
Information from ClinicalTrials.gov archive on the view of NCT00509795 "Vascular Endothelial Growth Factor (VEGF) Trap-Eye: Investigation of Efficacy and Safety in Wet Age-Related Macular Degeneration (AMD)" (Dec. 1, 2009).
Information from ClinicalTrials.gov archive on the view of NCT00789477 "DME and VEGF Trap-Eye: Investigation of Clinical Impact" (Nov. 18, 2010).
Information from ClinicalTrials.gov archive on the view of NCT00509795 "Vascular Endothelial Growth Factor (VEGF) Trap-Eye: Investigation of Efficacy and Safety in Wet Age-Related Macular Degeneration (AMD)" (Jan. 7, 2011).
Information from ClinicalTrials.gov archive on the view of NCT01012973 Vascular Endothelial Growth Factor (VEGF) Trap-Eye: Investigation of Efficacy and Safety in Central Retinal Vein Occlusion (CRVO)(Galileo) 7 pages, first posted Nov. 13, 2009; results first posted Nov. 22, 2012; last update posted Nov. 3, 2014; printed Dec. 4, 2019 (https://clinicaltrials.gov/ct2/show/study/NCT01012973) (Note: May correspond to "Vascular Endothelial Growth Factor Trap‐ Eye Investigation of Efficacy and Safety in Central Retinal Vein Occlusion title, 8 pages, Nov. 12, 2009, US [Cited in Third Party Observations filed in parent U.S. Appl. No. 16/055,847]" which was cited in the Third Party Observations dated May 1, 2019).
Kaiser, "Vascular endothelial growth factor Trap-Eye for diabetic macular oedema." Br. J. Ophthalmol, 93(2):135-36 (Feb. 2009).
Karia, Niral, "Retinal vein occlusion: pathophysiology and treatment options" Clinical Ophthalmology, 4:809-816 (2010).
Korobelnik et al., "Intravitreal Aflibercept Injection for Macular Edema Resulting from Central Retinal Vein Occlusion" American Academy of Ophthalmology (2014) 121(1):202-208.
Korobelnik, "Intravitreal Aflibercept for Diabetic Macular Edema." Ophthalmology, 121(11):2247-54 (Nov. 2014).

(56) References Cited

OTHER PUBLICATIONS

Kuo, "Comparative evaluation of the antitumor activity of antiangiogenic proteins delivered by gene transfer" PNAS 98(8):4605-4610 (Apr. 10, 2001).

Krzystolik et al., "Prevention of Experimental Choroidal NEovascularization With Intravitreal Anti-Vascular Endothelial Growth Factor Antibody Fragment" Arch Ophthamol., 120:338-346 (Mar. 2002).

Lalwani, "All About PrONTO: Study Yielded Good Results in AMD With Treatment Guided by OCT." Retina Today (May 2007).

Lalwani, A Variable-dosing Regimen with Intravitreal Ranibizumab for Neovascular Age-related Macular Degeneration: Year 2 of the PrONTO Study. Am J Ophthalmology, 148(1):43-58 (Jul. 2009).

Levine, "Macular Hemorrhage in Neovascular Age-Related Macular Degeneration After Stabilization With Antiangiogenic Therapy." Retina, 29(8):1074-79 (2009).

Lucentis Label Title, 7 pages, Jun. 30, 2010 [Cited in Third Party Observations filed in parent U.S. Appl. No. 16/055,847].

Major et al., "Da Vinci: DME and VEGF Trap-Eye: Investigation of Clinical Impact: Phase 2 Study in Patients with Diabetic Macular Edema (DME)" ARVO Annual Meeting Abstract (Apr. 2010).

Margolis, "Hemorrhagic Recurrence of Neovascular Age-Related Macular Degeneration Not Predicted by Spectral Domain Optical Coherence Tomography." Retinal Cases & Brief Reports, 4:1-4 (2010).

Massin, "Safety and Efficacy of Ranibizumab in Diabetic Macular Edema (Resolve Study*)." Diabetes Care, 33(11):2399-405 (Nov. 2010).

Mitchell, "The Restore Study, Ranibizumab Monotherapy or Combined with Laser versus Laser Monotherapy for Diabetic Macular Edema." Ophthalmology, 188(4):615-25 (Apr. 2011).

Mitchell, Edith P. "Targeted Therapy for Metastatic Colorectal Cancer: Role of Aflibercept" Clinical Colorectal Cancer (2013) 12(2):73-85.

Mitra et al., "Review of anti-vascular endothelial growth factor therapy in macular edema secondary to central retinal vein occlusions" Expert Review in Ophthalmol, Taylor & Francis, GB 6(6):623-629 (Jan. 2011).

Mousa and Mousa, "Current Status of Vascular Endothelial Growth Factor Inhibition in Age-Related Macular Degeneration" Biodrugs; 24(3); 183-194 (2010).

N/A "Materials from Jun. 2011 FDA Committee Mtg" (Jun. 17, 2011).

N/A "Materials from Dec. 2011 FDA Committee Mtg"(Dec. 1, 2011).

Nguyen et al., "A Phase I Study of Intravitreal Vascular Endothelial Growth Factor Trap-Eye in Patients with Neovascular Age-Related Macular Degeneration" Opthamology, J.B. Lippincott Co., Philadelphia, PA, US, 116(11):2141-2148 (Nov. 1, 2009).

Nguyen et al., "A phase I trial of an IV-administered vascular endothelial growth factor trap for treatment in patients with choroidal neovascularization due to age-related macular degeneration" Ophthalmology, 113(9):1522e1-1522e14 (Sep. 2006) (epub Jul. 28, 2006).

Nguyen et al., "Randomized, Double-masked, Active-controlled Phase 3 Trial of the Efficacy and Safety of Intravitreal VEGF Trap-Eye in Wet AMD: One-year Results of the View 1 Study" ARVO Annual Meeting Abstract (Apr. 2011).

Nguyen, "Ranibizumab for Diabetic Macular Edema, Results from 2 Phase III Randomized Trials: Rise and Ride." Ophthalmology, 119(4):789-801 (Apr. 2012).

Nguyen et al., "Results of a Phase I, Dose-Escalation, Safety, Tolerability, and Bioactivity Study of Intravitreous VEGF Trap in Patients with Neovascular Age-Related Macular Degeneration" ARVO Annual Meeting Abstract (May 2006).

Nichols, Earl R., "AAO: Ranibizumab (rhuRab) May Improve Vision in Age-Related Macular Degeneration" Doctor's Guide Global Edition, www.pslgroup.com/dg/23f2aa.htm, pp. 1-2 (Nov. 24, 2003).

Noguera-Troise et al., "Blockade of Dll4 inhibits tumour growth by promoting non-productive angiogenesis" Nature (Dec. 2006) 444:1032-1037.

Ohr, "Aflibercept in wet age-related macular degeneration: a perspective review" Ther. Adv. Chronic Dis., 3(4):153-161 (2012).

Olivera et al., "VEGF Trap R1R2 suppresses experimental corneal angiogenesis" European Journal of Ophthalmology, 20(1):48-54 (Jan. 1, 2010).

Pai et al., "Current concepts in intravitreal drug therapy for diabetic retinopathy" Saudi Journal of Ophthalmology 24(4):143-149 (Jun. 30, 2010).

Papadppoulos, "Binding and neutralization of vascular endothelial growth factor (VEGF) and related ligands by VEGF Trap, ranibizumab and bevacizumab" Angiogenesis, 15:171-185 (2012).

Regeneron SEC Form 10-K (Feb. 27, 2008).
Regeneron SEC Form 10-K (Feb. 26, 2009).
Regeneron SEC Form 10-K (Feb. 17, 2011).
Regeneron SEC Form 10-Q (May 8, 2006).
Regeneron SEC Form 10-Q (Aug. 8, 2006).
Regeneron SEC Form 10-Q (Nov. 6, 2006).
Regeneron SEC Form 10-Q (May 4, 2007).
Regeneron SEC Form 10-Q (Aug. 3, 2007).
Regeneron SEC Form 10-Q (Apr. 30, 2009).
Regeneron SEC Form 10-Q (Nov. 3, 2009).
Regeneron SEC Form 10-Q (Apr. 29, 2010).
Regeneron SEC Form 10-Q (Jul. 28, 2010).
Regeneron SEC Form 10-Q (Oct. 28, 2010).
Regeneron SEC Form 10-Q (May 3, 2011).
Regeneron SEC Form 10-Q (Jul. 28, 2011).
Regeneron SEC Form 10-Q (Oct. 27, 2011).

Regeneron SEC Form 8-K Exhibit: "Press Release of Regeneron Pharmaceuticals, Inc. dated May 1, 2006" (May 2, 2006).

Regeneron SEC Form 8-K Exhibit: "Press Release of Regeneron Pharmaceuticals, Inc. dated May 3, 2006" (May 5, 2006).

Regeneron SEC Form 8-K Exhibit: "Slides presented at the Company's 2006 Annual Meeting of Shareholders held on Jun. 9, 2006" (Jun. 9, 2006).

Regeneron SEC Form 8-K Exhibit: "Press Release dated May 2, 2007" (May 3, 2007).

Regeneron SEC Form 8-K Exhibit: "Overheads for presentation at Regeneron's Annual Meeting of Shareholders to be held on Jun. 8, 2007" (Jun. 8, 2007).

Regeneron SEC Form 8-K Exhibit: "Press Release dated Oct. 1, 2007" (Oct. 1, 2007).

Regeneron SEC Form 8-K Exhibit: "Press Release dated Nov. 6, 2007" (Nov. 6, 2007).

Regeneron SEC Form 8-K Exhibit: "Press Release dated May 1, 2008" (May 2, 2008).

Regeneron SEC Form 8-K Exhibit: "Press Release dated Nov. 4, 2008" (Nov. 4, 2008).

Regeneron SEC Form 8-K Exhibit: "99(a) Slides that Regeneron Pharmaceuticals, Inc. intends to use in conjunction with meetings with investors at the J.P. Morgan 27th Annual Healthcare Conference in San Francisco on Jan. 12-15, 2009." (Jan. 9, 2009).

Regeneron SEC Form 8-K Exhibit: "Press Release dated Apr. 30, 2009" (May 1, 2009).

Regeneron SEC Form 8-K Exhibit: "Press Release dated Nov. 3, 2009." (Nov. 4, 2009).

Regeneron SEC Form 8-K Exhibit: "Press Release Reporting Positive Results for VEGF Trap-Eye in Phase 3 Study in Central Retinal Vein Occlusion (CRVO) and in Phase 2 Study in Diabetic Macular Edema (DME) dated Dec. 20, 2010." (Dec. 20, 2010).

Regeneron SEC Form 8-K Exhibit: "Press Release dated Feb. 17, 2011" (Feb. 18, 2011).

Regeneron SEC Form 8-K Exhibit: "Press Release Reporting Positive Results for VEGF Trap-Eye in Second Phase 3 Study in Central Retinal Vein Occlusion, dated Apr. 27, 2011" (Apr. 27, 2011).

Regeneron SEC Form 8-K Exhibit: "Press Release dated May 3, 2011." (May 3, 2011).

Regeneron SEC Form 8-K Exhibit: "Press Release, dated Jun. 17, 2011, Announcing that EYLEA™ (aflibercept ophthalmic solution) Received Unanimous Recommendation for Approval for Treatment of Wet AMD from FDA Advisory Committee." (Jun. 21, 2011).

(56) References Cited

OTHER PUBLICATIONS

Regeneron SEC Form 8-K Exhibit: "Presentation entitled VEGF Trap-Eye in CRVO: 1-year Results of the Phase 3 Copernicus Study" (Aug. 22, 2011).
Regeneron SEC Form 8-K Exhibit: "Press Release Announcing FDA Approval of EYLEA™ (aflibercept) Injection for the Treatment of Wet Age-Related Macular Degeneration, dated Nov. 18, 2011" (Nov. 21, 2011).
Regeneron Press Release "Positive Interim Phase 2 Data Reported for VEGF Trap-Eye in Age-Related Macular Degeneration" (Mar. 27, 2007).
Regeneron Press Release "VEGF Trap-Eye Phase 2 Wet AMD Results Reported at Arvo Annual Meeting" (May 9, 2007).
Regeneron Press Release "Regeneron Reports Second Quarter Financial and Operating Results" (Aug. 1, 2007).
Regeneron Pharmaceuticals, Inc., "Regeneron and Bayer Healthcare Initiate Phase 3 Global Development Program for VEGF Trap-Eye in Wet Age-Related Macular Degeneration (AMD)" (Aug. 2, 2007).
Regeneron Pharmaceuticals, Inc. Form 10-Q, published on Nov. 7, 2007 for the period ending Sep. 30, 2007.
Regeneron Press Release "Regeneron Announces Positive Primary Endpoint Results From a Phase 2 Study of VEGF Trap-Eye in Age-Related Macular Degeneration" (Oct. 1, 2007).
Regeneron Press Release "Regeneron Reports Fourth Quarter and Full Year 2007 Financial and Operating Results" (Feb. 27, 2008).
Regeneron Pharmaceuticals, Inc., "Regeneron and Bayer Healthcare Announce Encouraging 32-Week Follow-up Results from a Phase 2 Study of VEGF Trap-Eye in Age-Related Macular Degeneration" (Apr. 28, 2008).
Regeneron, Press release "Regeneron Reports First Quarter 2008 Financial and Operating Results", May 1, 2008.
Regeneron Press Release, "Bayer and Regeneron Dose First Patient in Second Phase 3 Study for VEGF Trap-Eye in Wet Age-Related Macular Degeneration." May 8, 2008.
Regeneron Pharmaceuticals Inc., "Clear-It-2: Interim Results of the Phase II, Randomized, Controlled Dose-and Interval-ranging Study of Repeated Intravitreal VEGF Trap Administration in Patients With Neovascular Age-related Macular Degeneration (AMD)" poster presented at the 2007 Association for Research in Vision and Ophthalmology meeting in Ft. Lauderdale, Florida (May 2007).
Regeneron Pharmaceuticals Inc., "An Exploratory Study of the Safety, Tolerability and Biological Effect of a Single Intravitreal Administration of VEGF Trap in Patients with Diabetic Macular Edema" poster presented at the 2007 Association for Research in Vision and Ophthalmology meeting in Ft. Lauderdale, Florida (May 2007).
Regeneron Pharmaceuticals Inc., "Optical Coherence Tomography Outcomes of a Phase 1, Dose-Escalation, Safety, Tolerability, and Bioactivity Study of Intravitreal VEGF Trap in Patients with Neovascular Age-Related Macular Degeneration: The Clear-It 1 Study" poster presented at the 2007 Association for Research in Vision and Ophthalmology meeting in Ft. Lauderdale, Florida (May 2007).
Regeneron Pharmaceuticals, Inc., "Regeneron and Bayer Healthcare Announce VEGF Trap-Eye Achieved Durable Improvement in Vision over 52 Weeks in a Phase 2 Study in Patients with Age-related Macular Degeneration" (Aug. 19, 2008).
Regeneron Pharmaceuticals Inc., "View 1 Vascular Endothelial Growth Factor (VEGF) Trap-Eye 1-Year Results: Investigation of Efficacy and Safety in Wet Age-Related Macular Degeneration (AMD)" presented at Bascom Palmer Eye Institute's Angiogenesis, Exudation and Degeneration 2011 meeting in Miami, Florida (Feb. 12, 2011).
Regeneron Pharmaceuticals Inc., "View 2 Vascular Endothelial Growth Factor (VEGF) Trap-Eye 1-Year Results: Investigation of Efficacy and Safety in Wet Age-Related Macular Degeneration (AMD)" presented at Bascom Palmer Eye Institute's Angiogenesis, Exudation and Degeneration 2011 meeting in Miami, Florida (Feb. 12, 2011).

Regeneron Pharmaceuticals Inc., "VEGF Trap-Eye Clear-It 2 Final Primary Endpoint Results" presented at the 2007 Retina Society Conference in Boston, Massachusetts (Sep. 30, 2007).
Regeneron Pharmaceuticals Inc., "VEGF Trap-Eye Final Phase 2 Results in Age-related Macular Degeneration Presented at 2008 Retina Society Meeting" (Sep. 28, 2008) (XP-002770952).
Regeneron 2008 Annual Report.
Regeneron Pharmaceuticals, Inc. "Regeneron Reports Full Year and Fourth Quarter 2008 Financial and Operating Results" (Feb. 26, 2009).
Regeneron Pharmaceuticals, Inc. "Bayer and Regeneron Extend Development Program for VEGF Trap-Eye to Include Central Retinal Vein Occlusion" (Apr. 30, 2009).
Regeneron Press Release "First Patient Enrolled in Regeneron and Bayer Healthcare VEGF Trap-Eye Phase 3 Program in Central Retinal Vein Occlusion" (Jul. 23, 2009).
Regeneron Press Release "Enrollment Completed in Regeneron and Bayer HealthCare Phase 3 Studies of VEGF Trap-Eye in Neovascular Age-Related Macular Degeneration (Wet AMD)" Sep. 14, 2009.
Regeneron 2009 Annual Report and 10-K.
Regeneron Press Release, "VEGF Trap-Eye Shows Positive Results in a Phase 2 Study in Patients With Diabetic Macular Edema." Feb. 18, 2010.
Regeneron Press Release "Regeneron Schedules Nov. 22, 2010 Teleconference and Webcast to Discuss Results of Two Phase 3 Studies With VEGF Trap-Eye in Wet Age-Related Macular Degeneration" (Nov. 19, 2010).
Regeneron Press Release "Bayer and Regeneron Report Positive Top-Line Results of Two Phase 3 Studies with VEGF Trap-Eye in Wet Age-related Macular Degeneration" Nov. 22, 2010.
Regeneron Press Release "Regeneron and Bayer Report Positive Results for VEGF Trap-Eye in Phase 3 Study in Central Retinal Vein Occlusion (CRVO) and in Phase 2 Study in Diabetic Macular Edema (DME)" Dec. 20, 2010.
Regeneron 2010 Annual Report and 10-K.
Regeneron Press Release "Regeneron and Bayer Start Phase 3 Trial to Extend Ophthalmology Research & Development Program for VEGF Trap-Eye in Asia" (Jan. 18, 2011).
Regeneron Press Release "Regeneron to Webcast Investor Briefing on VEGF Trap-Eye Clinical Program on Sunday, Feb. 13 at 9 Am Et" (Feb. 9, 2011).
Regeneron Press Release "Regeneron Submits Biologies License Application to FDA for VEGF Trap-Eye for Treatment of Wet Age-Related Macular Degeneration" (Feb. 22, 2011).
Regeneron Press Release "Regeneron and Bayer Announce Start of Phase 3 Clinical Program in Diabetic Macular Edema" (Apr. 8, 2011).
Regeneron Pharmaceuticals, Inc., "FDA Grants Priority Review for VEGF Trap-Eye for the Treatment of Wet Age-Related Macular Degeneration" (Apr. 18, 2011).
Regeneron Press Release VEGF Trap-Eye Submitted for EU Marketing Authorization for Treatment of Wet Age-Related Macular Degeneration (Jun. 7, 2011).
Regeneron Pharmaceuticals, Inc., "Regeneron Announces EYLEA™ (aflibercept ophthalmic solution) Receives Unanimous Recommendation for Approval for Treatment of Wet AMD from FDA Advisory Committee" (Jun. 17, 2011).
Regeneron Press Release "Regeneron Announces Clinical Presentations at ASRS 2011 Annual Meeting" (Aug. 17, 2011).
Regeneron Pharmaceuticals, Inc., Regeneron Announces FDA Approval of EYLEA™ (aflibercept) Injection for the Treatment of Wet Age-Related Macular Degeneration: Corrected (Nov. 18, 2011).
Regeneron Pharmaceuticals, Inc., "Regeneron and Bayer Initiate Phase 3 Clinical Program for the Treatment of Wet Age-Related Macular Degeneration in China" (Nov. 28, 2011).
Regeneron Pharmaceuticals, Inc., "Two Year Results of Phase 3 Studies with EYLEA™ (aflibercept) Injection in wet AMD Show Sustained Improvement in Visual Acuity" (Dec. 5, 2011).
Regillo et al., "Randomized, Double-Masked, Sham-Controlled Trial of Ranibizumab for Neovascular Age-related Macular Degeneration: OIER Study Year 1" American Journal of Ophthalmology, 145(2):239-248 (2008).

(56) References Cited

OTHER PUBLICATIONS

Rosenfeld, "Ranibizumab for Neovascular Age-Related Macular Degeneration." N Engl J Med, 355(14):1419-31 (Oct. 5, 2006).
Rosenfeld, "Lessons Learned From Avastin and OCT—The Great, the Good, the Bad, and the Ugly: The LXXV Edward Jackson Memorial Lecture." Am. J. Ophthalmology, 204:26-45 (Aug. 2019).
Rudge et al., "VEGF Trap complex formation measures production rates of VEGF, providing a biomarker for predicting efficacious angiogenic blockade" PNAS (Nov. 20, 2007) 104(47):18363-18370.
Rudge et al. "Clinical Development of VEGF Trap" In: Figg W.D., Folkman J. (eds) Angiogenesis (2008).
Schmidt-Erfurth, "Efficacy and Safety of Monthly versus Quarterly Ranibizumab Treatment in Neovascular Age-related Macular Degeneration: The EXCIE Study" Ophthalmology, 118(5)831-839 (2010).
Schmidt-Erfurth et al. "Primary Results of an International Phase III Study Using Intravitreal VEGF Trap-Eye Compared to Ranibizumab in Patients with Wet AMD (View 2)" ARVO Annual Meeting Abstract (Apr. 2011).
Schmidt-Erfurth, "Three-Year Outcomes of Individualized Ranibizumab Treatment in Patients with Diabetic Macular Edema." Ophthalmology, 121(5):1045-53,(May 2014).
Schmidt-Erfurth et al., "Intravitreal Aflibercept Injection for Neovascular Age-related Macular Degeneration" Ophthalmology (2014) 121:193-201.
Schnichels, "Comparative toxicity and proliferation testing of aflibercept, bevacizumab and ranibizumab on different ocular cells." Br. J. Ophthalmol., 97:917-923 (2013).
Semeraro et al., "Aflibercept in wet AMD: specific role and optimal use" Drug Design, Development and Therapy (Aug. 2, 2013) 7:711-722.
Sharma and S. and Kaiser, P. K., Update on VEGF Trap-Eye Clinical Trials and Retinal. Physician, pp. 1-6 (Nov./Dec. 2010) <URL: https://www.retinalphysician.com/issues/2010/nov-dec/update-on-vegf-trap-eye-clinical-trials>.
Simo and Hernandez, "Advances in Medical Treatment of Diabetic Retinopathy" Diabetes Care, 32(8):1556-1562 (Aug. 2009).
Slakter et al., "Influence of Baseline Angiographic Classification on Outcomes in the Clear-It 2 Phase 2 Study of Intravitreal VEGF Trap-Eye in Neovascular Age-Related Macular Degeneration" ARVO Annual Meeting Abstract (Apr. 2010).
Slakter et al., "A Phase 2, Randomized, Controlled Dose-and Interval-Ranging Study of Intravitreal VEGF Trap-Eye in Patients with Neovascular Age-Related Macular Degeneration: Optical Coherence Tomography (OCT) and Fluorescein Angiography (FA) Outcomes at 1 Year" ARVO Annual Meeting Abstract (Apr. 2009).
Slides for the 2008 Retina Society Meeting "VEGF Trap-Eye in Wet AMD Clear-It 2: Summary of One-Year Key Results", Sep. 28, 2008.
Spaide, "Ranibizumab According to Need: A Treatment for Age-related Macular Degeneration." Am J Ophthalmology, 143(4):679-680 (Apr. 2007).
Stewart, "The expanding role of vascular endothelial growth factor inhibitors in opthamology" Mayo Clin Proc. 87(1):77-88 (Jan. 2012).
Stewart et al., "Predicted biological activity of intravitreal VEGF Trap" British Journal of Ophthalmology, 92(5):667-668 (2008).
Stewart, "Aflibercept" Nature Reviews: Drug Discovery 11:269-270 (Apr. 1, 2012).
Tannock et al., "Aflibercept versus placebo in combination with docetaxel and prednisone for treatment of men with metastatic castration-resistant prostate cancer (Venice): a phase 3, double-blind randomized trial" Lancet Oncol (2013) 14:760-768.
Thomas Reuters Integrity "VEGF Trap-Eye final phase II results in age-related macular degeneration presented at 2008 Retina Society Meeting" (Sep. 28, 2008).
Thurston, Gavin "Complementary actions of VEGF and Angiopoietin-1 on blood vessel growth and leakage" J. Anat. (2002) 200:575-580.
Thurston, "Vascular endothelial growth factor and other signaling pathways in developmental and pathologic angiogenesis." International Journal of Hematology, 80:7-20 (2004).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 38 pages, Latest version submitted Oct. 27, 2014 on ClinicalTrials.gov (NCT01012973_01182013_27424.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 10 pages, Latest version submitted Oct. 27, 2014 on ClinicalTrials.gov (NCT01012973_01252011_27433.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 11 pages, Latest version submitted Oct. 27, 2014 on ClinicalTrials.gov (NCT01012973_01262012_27428.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 38 pages, Latest version submitted Oct. 27, 2014 on ClinicalTrials.gov (NCT01012973_01302013_27423.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 12 pages, Latest version submitted Oct. 27, 2014 on ClinicalTrials.gov (NCT01012973_02092010_27442.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 11 pages, Latest version submitted Oct. 27, 2014 on ClinicalTrials.gov (NCT01012973_02202012_27427.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 12 pages, Latest version submitted Oct. 27, 2014 on ClinicalTrials.gov (NCT01012973_03162010_27441.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 10 pages, Latest version submitted Oct. 27, 2014 on ClinicalTrials.gov (NCT01012973_04082011_27432.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 12 pages, Latest version submitted Oct. 27, 2014 on ClinicalTrials.gov (NCT01012973_04162010_27440.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 10 pages, Latest version submitted Oct. 27, 2014 on ClinicalTrials.gov (NCT01012973_06232011_27431.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 12 pages, Latest version submitted Oct. 27, 2014 on ClinicalTrials.gov (NCT01012973_07222010_27439.1).
Updated Information from ClinicalTrials.gov archive History of Changes for Study: NCT01012973 Vascular Endothelial Growth Factor (VEGF) Trap-Eye: Investigation of Efficacy and Safety in

(56) References Cited

OTHER PUBLICATIONS

Central Retinal Vein Occlusion (CRVO)(Galileo) 12 pages, Latest version submitted Oct. 27, 2014 on ClinicalTrials.gov (NCT01012973_08252010_27438.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 10 pages, Latest version submitted Oct. 27, 2014 on ClinicalTrials.gov (NCT01012973_08262010_27437.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 10 pages, Latest version submitted Oct. 27, 2014 on ClinicalTrials.gov (NCT01012973_09082010_27436.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 10 pages, Latest version submitted Oct. 27, 2014 on ClinicalTrials.gov (NCT01012973_09192011_27430.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 10 pages, Latest version submitted Oct. 27, 2014 on ClinicalTrials.gov (NCT01012973_10042010_27435.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 38 pages, Latest version submitted Oct. 27, 2014 on ClinicalTrials.gov (NCT01012973_10232012_27426.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 38 pages, Latest version submitted Oct. 27, 2014 on ClinicalTrials.gov (NCT01012973_10272013_27422.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 10 pages, Latest version submitted Oct. 27, 2014 on ClinicalTrials.gov (NCT01012973_11012010_27434.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 12 pages, Latest version submitted Oct. 27, 2014 on ClinicalTrials.gov (NCT01012973_11132009_27444.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 10 pages, Latest version submitted Oct. 27, 2014 on ClinicalTrials.gov (NCT01012973_11292011_27429.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 38 pages, Latest version submitted Oct. 27, 2014 on ClinicalTrials.gov (NCT01012973_12182012_27425.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo) 12 pages, Latest version submitted Oct. 27, 2014 on ClinicalTrials.gov (NCT01012973_12212010_27443.1).

Vascular Endothelial Growth Factor Trap‐ Eye Investigation of Efficacy and Safety in Central Retinal Vein Occlusion title, 8 pages, Nov. 12, 2009, US [Cited in Third Party Observations filed in parent U.S. Appl. No. 16/055,847] Note: May correspond to "Information from ClinicalTrials.gov archive on the view of NCT01012973" Vascular Endothelial Growth Factor (VEGF) Trap-Eye: Investigation of Efficacy and Safety in Central Retinal Vein Occlusion (CRVO)(Galileo) 7 pages, first posted Nov. 13, 2009; results first posted Nov. 22, 2012; last update posted Nov. 3, 2014; printed Dec. 4, 2019 (https://clinicaltrials.gov/ct2/show/study/NCT01012973) in the Office Action dated Dec. 10, 2019 in U.S. Appl. No. 16/055,847.
Wachsberger, "VEGF trap in combination with radiotherapy improves tumor control in u87 glioblastoma." Int. J. Radiation Oncology Biol Phys. 67(5):1526-1537 (2007).
WHO Drug Information, "International Nonproprietary Names for Pharmaceutical Substances (INN)" 20(2):115-119 (2006).
Wolfson, "Regeneron Focuses on Age-Related Macular Degeneration." Chemistry & Biology 15:303-304 (Apr. 2008).
Xia et al., "Transgenic delivery of VEGF to mouse skin leads to an inflammatory condition resembling human psoriasis" Blood (Jul. 1, 2003) 102(1):161-168.
Yancopoulos, "Vascular-specific growth factors and blood vessel formation." Nature 407:242-48 (Sep. 14, 2000).
Yancopoulos, "Clinical Application of Therapies Targeting VEGF." Cell 143:13-16 (Oct. 1, 2010).
Yung, "Moving Toward the Next Steps in Angiogenesis Therapy?" Society for Neuro-Oncology, 10:939 (2008).
U.S. Pat. No. 7,374,758—Patent Term Extension Application submitted Dec. 22, 2011.
ADIS R&D Profile "Aflibercept: AVE 0005, AVE 005, AVE0005, VEGF Trap—Regeneron, VEGF Trap (R1R2), VEGF Trap-Eye." Drugs R D, 9(4):261-269 (2008).
Andersen & Krummen, "Recombinant protein expression for therapeutic applications" Current Opinion in Biotechnology 13:117-123 (2002).
Anderson et al., "Delivery of Anti-Angiogenic Molecular Therapies for Retinal Disease" Drug Discovery Today 15: 272 (2010).
Article in Retinal Physician, "Subspecialty News", available online at http://www.retinalphysician.com/printarticle.aspx?articleID=104007 (Mar. 2010).
Ass'n for Res. Vision & Ophthalmology, ARVO® News (Summer 2007).
Ass'n for Res. Vision & Ophthalmology, ARVO® News (Winter/Spring 2008).
AVASTIN® label.
Avery, R. L., D. J. Pieramici, M. D. Rabena, A. A. Castellarin, M. A. Nasir and M. J. Giust, "Intravitreal bevacizumab (Avastin) for neovascular age-related macular degeneration" Ophthalmology 113(3): 363-372 e365 (2006).
Bashshur et al., "Intravitreal Bevacizumab for the Management of Choroidal Neovascularization in Age-Related Macular Degeneration" Am J. Ophthalmology 142: 1 (2006).
Bayer Press Release, "Bayer and Regeneron Dose First Patient in Second Phase 3 Study for VEGF Trap-Eye in Wet Age-Related Macular Degeneration." May 8, 2008.
Bayer Press Release, "VEGF Trap-Eye Shows Positive Results in Phase II Study in Patients with Diabetic Macular Edema" Feb. 18, 2010.
Bayer Press Release, "Bayer HealthCare and Regeneron Announce Encouraging 32-Week Follow Up Results From a Phase 2 Study of VEGF Trap-Eye in Age-Related Macular Degeneration" Apr. 28, 2008.
Bayer Press Release "Bayer HealthCare and Regeneron Announce VEGF Trap-Eye Achieved Durable Improvement in Vision Over 52 Weeks in a Phase 2 Study in Patients with Age-Related Macular Degeneration" Aug. 19, 2008.
BMJ Publishing Group Ltd., "Review: Ranibizumab (Lucentis) in Neovascular Age-Related Macular Degeneration: Evidence From Clinical Trials" British J. Ophthalmology (Dec. 2020), https://bjo.bmj.com/content/94/1/2.altmetrics.

(56) References Cited

OTHER PUBLICATIONS

Bontempo, "Preformulation Development of Parenteral Biopharmaceuticals" Drugs and the Pharmaceutical Sciences 85:91-108 (1997).
Bressler, N. M. and G. Treatment of Age-Related Macular Degeneration with Photodynamic Therapy Study, "Photodynamic therapy of subfoveal choroidal neovascularization in age-related macular degeneration with verteporfin: two-year results of 2 randomized clinical trials-tap report 2." Arch Ophthalmol 119(2): 198-207 (2001).
Brown & Regillo, "Anti-VEGF Agents in the Treatment of Neovascular Age-Related Macular Degeneration: Applying Clinical Trial Results to the Treatment of Everyday Patients" Am J. Ophthalmology 144: 627 (2007).
Chi et al., "Physical Stability of Proteins in Aqueous Solution: Mechanism and Driving Forces in Nonnative Protein Aggregation" Pharmaceutical Research vol. 20, No. 9, 1325-1336 (Sep. 2003).
Ciulla & Rosenfeld, "Antivascular Endothelial Growth Factor Therapy for Neovascular Age-Related Macular Degeneration" Current Opinion Ophthalmology 20: 158 (2009).
Clinicaltrials.gov. I-SPY 2 Trial: Neoadjuvant and Personalized Adaptive Novel Agents to Treat Breast Cancer, Accessed 2010; http://clinicaltrials.gov/ct2/show/NCT01042379?term-NCT01042379&rank=1.
CMS, Local Coverage Determination (LCD) for Ranibizumab (Lucentis) (L29266, First Coast Service Options, Inc Jun. 14, 2011).
Controls in SCI experiments, RegenBase. Retrieved Jan. 6, 2021, from http://regenbase.org/control-groups.html.
Department of Health and Human Services, Office of Inspector General, "Questionable Billing for Medicare Ophthalmology Services" Sep. 2015 OEI-04-12-00280.
Drug Vehicle (Code C927), National Cancer Institute (NCI). Retrieved Jan. 6, 2021, from https://ncithesaurus.nci.nih.gov/ncitbrowser/ConceptReport.jsp?dictionary=NCI_Thesaurus&code=C927&ns=ncit.
EP 2 663 325 File History.
Eylea® Prescribing Information, Revised May 2019.
Ferrara, N. & Kerbel, R., "Angiogenesis as a Therapeutic Target" Nature 438: 967 (2005).
Fraser et al., "Single Injections of Vascular Endothelial Growth Factor Trap Block Ovulation in the Macaque and Produce a Prolonged, Dose-Related Suppression of Ovarian Function." J. Clin. Endocrinol & Metab. 90(2): 1114-1122 (Feb. 2005).
Genentech, "FDA Approves Lucentis for the Treatment of Wet Age-Related Macular Degeneration," News Release dated Jun. 30, 2006 (Jun. 30, 2006).
Gupta, O. P., G. Shienbaum, A. H. Patel, C. Fecarotta, R. S. Kaiser and C. D. Regillo, "A treat and extend regimen using ranibizumab for neovascular age-related macular degeneration clinical and economic impact" Ophthalmology 117(11): 2134-2140 (2010).
Heier, "Intravitreal VEGF Trap for AMD: An Update" Retina Today 44 (Oct. 2009).
Heier, J. S., P. A. Campochiaro, L. Yau, Z. Li, N. Saroj, R. G. Rubio and P. Lai "Ranibizumab for macular edema due to retinal vein occlusions: long-term follow-up in the Horizon trial" Ophthalmology 119(4): 802-809 (2012).
HERCEPTIN® label.
Holz et al., "VEGF Trap-Eye for Macular Oedema Secondary to Central Retinal Vein Occlusion: 6-Month Results of the Phase III Galileo Study" British J. Ophthalmology 97: 278 (2013).
Ip, M. S., I. U. Scott, P. C. VanVeldhuisen, N. L. Oden, B. A. Blodi, M. Fisher, L. J. Singerman, M. Tolentino, C. K. Chan, V. H. Gonzalez and S. S. R. Group "A randomized trial comparing the efficacy and safety of intravitreal triamcinolone with observation to treat vision loss associated with macular edema secondary to central retinal vein occlusion: the Standard Care vs Corticosteroid for Retinal Vein Occlusion (SCORE) study report 5" Arch Ophthalmol 127(9): 1101-1114 (2009).

Janeway et al., "The structure of a typical antibody molecule" Immunobiology: The Immune System in Health and Disease. 5th edition. New York: Garland Science (2001).
Keane et al., "Effect of Ranibizumab Retreatment Frequency on Neurosensory Retinal Volume in Neovascular AMD" Retina 29: 592 (2009).
Kim et al., "Potent VEGF Blockade Causes Regression of Coopted Vessels in a Model of Neuroblastoma" Proc. Nat'l Acad. Sci. 99: 11399 (2002).
LUCENTIS Approval (2006).
LUCENTIS® Label (14 pages).
LUCENTIS® Prescribing Information (2006).
Macular Photocoagulation Study, G., "Laser photocoagulation of subfoveal neovascular lesions in age-related macular degeneration. Results of a randomized clinical trial. Macular Photocoagulation Study Group" Arch Ophthalmol 109(9): 1220-1231 (1991).
Massin, "Anti-VEGF Therapy for Diabetic Macular Edema: An Update" Retina Today 54 (Sep./Oct. 2008).
Michels, S., P. J. Rosenfeld, C. A. Puliafito, E. N. Marcus and A. S. Venkatraman, "Systemic bevacizumab (Avastin) therapy for neovascular age-related macular degeneration twelve-week results of an uncontrolled open-label clinical study" Ophthalmology 112(6): 1035-1047 (2005).
Mitchell et al., "Ranibizumab (Lucentis) in Neovascular Age-Related Macular Degeneration: Evidence from Clinical Trials" Brit. J. Ophthalmology 94: 2 (2009).
Ni & Hui, "Emerging Pharmacologic Therapies for Wet Age-Related Macular Degeneration" Ophthalmologica 223: 401 (2009).
Parkins & Lashmar, "The formulation of biopharmaceutical products" Pharmaceutical Science & Technology Today vol. 3, No. 4: 129-137 (Apr. 4, 2000).
Phosphate buffer. Cold Spring Harbor Protocols 2006: pdb.rec8543 (2006).
Randolph & Jones, "Surfactant-Protein Interactions" Rational Design of Stable Protein Formulations pp. 159-175, Springer, Boston, MA (2002).
RAPTIVA® label.
Regeneron Pharmaceuticals Inc. Regeneron Receives $20 Million Milestone Payment for Initiation of Phase 3 Study of VEGF Trap-Eye in Wet AMD. Media Release: Aug. 14, 2007. Available from URL: http://www.regeneron.com.
Regeneron Pharmaceuticals Inc. Regeneron Reports Fourth Quarter and Full Year 2004 Financial and Operating Results. Media Release: Feb. 22, 2005. Available from URL: http://www.regeneron.com.
Regeneron Pharmaceuticals Inc. Regeneron Reports Fourth Quarter and Full Year 2005 Financial and Operating Results. Media Release: Feb. 24, 2006. Available from URL: http://regeneron.com.
Regeneron Pharmaceuticals Inc. Regeneron Reports Positive Phase Data for the VEGF Trap in Age-Related Macular Degeneration; Preliminary Results Show Improvements in Vision and Reginal Swelling; VEGF Trap Was Well Tolerated at All Dose Levels. Media Release: May 1, 2006. Available from URL: http://www.regeneron.com.
Regeneron SEC Form 10-Q (Sep. 30, 2009).
Reichert, "Antibody-Based Therapeutics to Watch in 2011" MABS 3: 76 (2011).
REMICADE® label.
Retina Coding Q & A, Retinal Physician, 16: 18, 54 (Jul./Aug. 2019).
Rogers et al., "The prevalence of retinal vein occlusion: pooled data from population studies from the United States, Europe, Asia, and Australia" Ophthalmology 117(2): 313-319 e311 (2010).
Rosenfeld, P. J., A. A. Moshfeghi and C. A. Puliafito, "Optical coherence tomography findings after an intravitreal injection of bevacizumab (avastin) for neovascular age-related macular degeneration" Ophthalmic Surg Lasers Imaging 36(4): 331-335 (2005).
Rudge et al., "VEGF Trap as a Novel Antiangiogenic Treatment Currently in Clinical Trials for Cancer and Eye Diseases, and VelociGene®-based Discovery of the Next Generation of Angiogenesis Targets," Cold Spring Harbor Symposia on Quantitative Biology 70: 411-418 (2005).
Schmidt-Erfurth "Current Concepts in the Management of Diabetic Macular Edema" Proceedings 7:52 (2010).

(56) References Cited

OTHER PUBLICATIONS

Scott et al., "A randomized trial comparing the efficacy and safety of intravitreal triamcinolone with standard care to treat vision loss associated with macular Edema secondary to branch retinal vein occlusion: the Standard Care vs Corticosteroid for Retinal Vein Occlusion (SCORE) study report 6" Arch Ophthalmol 127(9): 1115-1128 (2009).
SIMULECT® label.
Spaide et al., "Prospective Study of Intravitreal Ranibizumab as a Treatment for Decreased Visual Acuity Secondary to Central Retinal Vein Occlusion" Am J. Ophthalmology 147: 298 (2009).
Spielberg, L. & Leys, A., "Intravitreal Bevacizumab for Myopic Choroidal Neovascularization: Short-Term and 1-Year Results" Bulletin Societe Beige D'Ophtalmologie 312: 17 (2009).
Steinbrook, "The Price of Sight—Ranibizumab, Bevacizumab, and the Treatment of Macular Degeneration" N. Eng. J. Med. 355:1409 (2006).
The Branch Vein Occlusion Study, G., "Argon laser photocoagulation for macular edema in branch vein occlusion" Am J Ophthalmol 98(3): 271-282 (1984).
The Central Vein Occlusion Study, G., "Evaluation of grid pattern photocoagulation for macular edema in central vein occlusion. The Central Vein Occlusion Study Group M report" Ophthalmology 102(10): 1425-1433 (1995).
U.S. Dep't Health & Human Servs., Nat'l Inst. Health, Nat'l Eye Inst., "Age-Related Macular Degeneration: What You Should Know" (Sep. 2015) https://www.nei.nih.gov/sites/default/files/healthpdfs/WYSK_AMD_English_Sept2015_PRINT.pdf.
U.S. Dep't Health & Human Servs., Nat'l Inst. Health, Nat'l Eye Inst., "Diabetic Retinopathy: What You Should Know" (Sep. 2015), https://www.nei.nih.gov/sites/default/files/2019-06/Diabetic-Retinopathy-What-You-Should-Know-508.pdf.
U.S. Department of Health and Human Services Food and Drug Administration, "Guidance for industry Q1A(R2) stability testing of new drug substances and products" Rockville, MD (Nov. 2003).
Vascular Endothelial Growth Factor (VEGF) Trap-Eye: Investigation of Efficacy and Safety in Wet Age-Related Macular Degeneration (AMD) (View1), NCT00509795, ClinicalTrials.gov (Apr. 28, 2009), https://clinicaltrials.gov/ct2/show/NCT00509795 ("NCT-795").
Wall Street Journal, "Genentech's Big Drug for Eyes Faces a Rival" (2007).
Wulff et al., "Prevention of Thecal Angiogenesis, Antral Follicular Growth, and Ovulation in the Primate by Treatment with Vascular Endothelial Growth Factor Trap R1R2" Endocrinology 143(7): 2797-2807 (Jul. 2002).
XOLAIR® label.
Zarbin & Rosenfeld, "Pathway-Based Therapies for Age-Related Macular Degeneration: An Integrated Survey of Emerging Treatment Alternatives" Retina 30: 1350 (2010).
Anonymous, Meeting Archive Titled "PA003 Eighteen-Month Results From an Extension Study of a Phase 2, Dose- and Interval-Ranging Study of VEGF Trap-Eye in Wet AMD," presented by David S Boyer, MD at Moscone Center (Oct. 2009).
Anonymous, Meeting Archive Titled "PA040 One-Year Results of the Da Vinci Study of VEGF Trap-Eye in Diabetic Macular Edema," presented by Diana V Do, MD at Orange County Convention Center (Oct. 2011).
Anonymous, Meeting Archive Titled "PA080 One-Year Results of a Phase 2 Study of Intravitreal VEGF Trap-Eye in Patients with Neovascular Age-Related Macular Degeneration," presented by David S Boyer, MD at Georgia World Congress Center (Nov. 2008).
Anonymous, Meeting Archive Titled "PO259 OCT and Fluorescein Angiography Outcomes Through 1 Year for a Phase 2 Study of Intravitreal VEGF Trap-Eye in Neovascular AMD," presented by Peter K Kaiser, MD at Moscone Center (Oct. 2009).
Anonymous, Meeting Archive Titled "PO260 VEGF Trap-Eye Vision-Specific Quality of Life Through 52 Weeks in Patients with Neovascular AMD in Clear-It 2: A Phase 2 Clinical Trial," presented by Allen C Ho, MD at Moscone Center (Oct. 2009).
Anonymous, Meeting Archive Titled "PO492 One-Year Results of the View 1 and View 2 Studies: VEGF Trap-Eye in Wet AMD," presented by David M Brown MD at Orange County Center (Oct. 2011).
Anonymous, Meeting Archive Titled "PO549 the 6-Month (Primary Endpoint) Results of the Phase 3 Galileo Study: VEGF Trap-Eye in Central Retinal Vein Occlusion," presented by Jean-Francois Korobelnik, MD at Orange County Convention Center (Oct. 2011).
Anonymous, Meeting Archive Titled "PO571 OCT and Fluorescein Angiographic Outcomes Through 1 Year for the Phase 2 Study of Intravitreal VEGF Trap-Eye in Neovascular AMD," presented by Quan Dong Nguyen, MD at Georgia World Congress Center (Nov. 2008).
Bressler, N. M. Treatment of Age-Related Macular Degeneration with Photodynamic Therapy Study Group, "Photodynamic therapy of subfoveal choroidal neovascularization in age-related macular degeneration with verteporfin: two-year results of 2 randomized clinical trials-tap report 2," Arch. Ophthalmol., 119(2):198-207 (2001).
Brown et al., "Ranibizumab for Diabetic Macular Edema (DME): 24-Month Efficacy and Safety Results of RISE—a Phase 3 Randomized Controlled Trial," ARVO Annual Meeting Abstract, *Investigative Ophthalmology & Visual Science*, 52:6647 (Apr. 2011).
Brown et al., "Sustained benefits from ranibizumab for macular edema following branch retinal vein occlusion: 12-month outcomes of a phase III study," *Ophthalmology*, 118(8):1594-2049 (2011).
Cao et al., "VEGF Trap Promotes Regression of Choroidal Neovascularization (CNV) and Inhibits Fibrosis and Inflammation in the Subretinal Matrigel CNV Model," ARVO Annual Meeting Abstract, *Investigative Ophthalmology & Visual Science*, 50:2979 (Apr. 2009).
Center for Drug Evaluation and Research BLA Application No. 125156 Medical Review, (Jun. 2006) <URL:https://www.accessdata.fda.gov/drugsatfda_docs/nda/2006/125156s0000_Lucentis_MedR.pdf>.
Cheung et al., "Combined anti-PIGF and anti-VEGF Therapy Ameliorates Pathological Neovascularization and Improves Retinal Revascularization in the Murine Model of Oxygen Induced Ischemic Retinopathy," ARVO Annual Meeting Abstract, *Investigative Ophthalmology & Visual Science*, 52:6064 (Apr. 2011).
The Eyetech Study Group, "Anti-Vascular Endothelial Growth Factor Therapy for Subfoveal Choroidal Neovascularization Secondary to Age-related Macular Degeneration," *Ophthalmology*, 110(5):979-986 (May 2003).
Heier et al., "Ranibizumab for Choroidal Neovascularization Secondary to Causes Other Than Age-Related Macular Degeneration: A Phase I Clinical Trial," *Ophthalmology*, 118(1):111-118 (Jan. 2011).
Heier, "Intravitreal Aflibercept for Diabetic Macular Edema: 148-Week Results from the VISTA and VIVID Studies," *Ophthalmology*, 123(11):2376-2385 (2016).
Herceptin label, Sep. 1998.
Information from ClinicalTrials.gov archive on the View 2 study (NCT00637377) "VEGF Trap-Eye: Investigation of Efficacy and Safety in Wet AMD (View 2)," v1 (Mar. 17, 2008).
Ip et al., "A randomized trial comparing the efficacy and safety of intravitreal triamcinolone with observation to treat vision loss associated with macular edema secondary to central retinal vein occlusion: the Standard Care vs Corticosteroid for Retinal Vein Occlusion (SCORE) study report 5," *Arch. Ophthalmol.*, 127(9):1101-1114 (2009).
Korobelnik et al., "Intravitreal Aflibercept Injection for Macular Edema Resulting from Central Retinal Vein Occlusion," *Ophthalmology*, 121(1):202-208 (2014).
Krzystolik et al., "Prevention of Experimental Choroidal Neovascularization With Intravitreal Anti-Vascular Endothelial Growth Factor Antibody Fragment," *Arch. Ophthalmol.*, 120(3):338-346 (Mar. 2002).
Lobov et al., "VEGF Trap Treatment Regresses Pathological Neovessels, Improves Revascularization and Reduces Retinal Ischemia in the Murine Oxygen-Induced Retinopathy (OIR) Model," ARVO Annual Meeting Abstract, *Investigative Ophthalmology & Visual Science*, 52:3128 (Apr. 2011).

(56) References Cited

OTHER PUBLICATIONS

Lucentis Approval (Jun. 30, 2006).
Lucentis Label Title, 7 pages, Jun. 2010 [Cited in Third Party Observations filed in parent U.S. Appl. No. 16/055,847].
Macular Photocoagulation Study Group, "Laser photocoagulation of subfoveal neovascular lesions in age-related macular degeneration. Results of a randomized clinical trial," *Arch. Ophthalmol.*, 109(9):1220-1231 (1991).
Mitchell et al., "Ranibizumab (Lucentis) in Neovascular Age-Related Macular Degeneration: Evidence from Clinical Trials," *Brit. J. Ophthalmology*, 94:2-13 (2010) (first online publication on May 20, 2009).
Regeneron Pharmaceuticals Inc., "Regeneron Receives $20 Million Milestone Payment for Initiation of Phase 3 Study of VEGF Trap-Eye in Wet AMD," Media Release: Aug. 13, 2007. Available from URL: http://www.regeneron.com.
Regeneron Pharmaceuticals Inc., "Regeneron Reports First Quarter 2008 Financial and Operating Results," Press release May 1, 2008.
Regeneron Pharmaceuticals Inc., Form 10-Q, published Nov. 7, 2007, for the period ending Sep. 30, 2007.
Rosenfeld et al., "Optical coherence tomography findings after an intravitreal injection of bevacizumab (avastin) for neovascular age-related macular degeneration," *Ophthalmic. Surg. Lasers Imaging*, 36(4):331-335 (2005).
Scott et al., "A randomized trial comparing the efficacy and safety of intravitreal triamcinolone with standard care to treat vision loss associated with macular Edema secondary to branch retinal vein occlusion: the Standard Care vs Corticosteroid for Retinal Vein Occlusion (SCORE) study report 6," *Arch. Ophthalmol.*, 127(9):1115-1128 & 127(12):1653 (2009).
Tolentino et al., "One-year Results of the Da Vinci Study of VEGF Trap-Eye in DME," ARVO Annual Meeting Abstract, *Investigative Ophthalmology & Visual Science*, 52:6646 (Apr. 2011).
Van Bruggen et al., "VEGF antagonism reduces edema formation and tissue damage after ischemia/reperfusion injury in the mouse brain," *The Journal of clinical investigation*, 104(11):1613-1620 (1999).
IPR2021-00880 dated Nov. 10, 2021, for U.S. Pat. No. 9,669,069 B2.
IPR2021-00881 dated Nov. 10, 2021, for U.S. Pat. No. 9,254,338 B2.
Anderson et al., "Delivery of Anti-Angiogenic Molecular Therapies for Retinal Disease," *Drug Discovery Today*, 15(7/8):272-282 (2010).
Avastin Label (Revised Dec. 2017).
Avery, R. L., D. J. Pieramici, M. D. Rabena, A. A. Castellarin, M. A. Nasir and M. J. Giust, "Intravitreal bevacizumab (Avastin) for neovascular age-related macular degeneration," *Ophthalmology*, 113(3):363-372e5 (2006).
Bashshur et al., "Intravitreal Bevacizumab for the Management of Choroidal Neovascularization in Age-Related Macular Degeneration," *Am. J. Ophthalmology*, 142(1):1-9 (2006).
Brown & Regillo, "Anti-VEGF Agents in the Treatment of Neovascular Age-Related Macular Degeneration: Applying Clinical Trial Results to the Treatment of Everyday Patients," *Am J. Ophthalmology*, 144(4)627-637e2 (2007).
Chi et al., "Physical Stability of Proteins in Aqueous Solution: Mechanism and Driving Forces in Nonnative Protein Aggregation" *Pharmaceutical Research*, 20(9):1325-1336 (Sep. 2003).
Ciulla & Rosenfeld, "Antivascular Endothelial Growth Factor Therapy for Neovascular Age-Related Macular Degeneration," *Current Opinion Ophthalmology*, 20:158-165 (2009).
Ferrara, N. & Kerbel, R., "Angiogenesis as a Therapeutic Target," *Nature*, 438:967-974 (2005).
Heier et al., "Ranibizumab for macular edema due to retinal vein occlusions: long-term follow-up in the Horizon trial," *Ophthalmology*, 119(4):802-809 (2012).
Holz et al., "VEGF Trap-Eye for Macular Oedema Secondary to Central Retinal Vein Occlusion: 6-Month Results of the Phase III Galileo Study," *British J. Ophthalmology*, 97:278-284 (2013).

Information from ClinicalTrials.gov archive on the View 1 study (NCT00509795) "Vascular Endothelial Growth Factor (VEGF) Trap-Eye: Investigation of Efficacy and Safety in Wet Age-Related Macular Degeneration (AMD) (View1)," changes from v8 (Mar. 3, 2009) to v9 (Apr. 28, 2009).
Keane et al., "Effect of Ranibizumab Retreatment Frequency on Neurosensory Retinal Volume in Neovascular AMD," *Retina*, 29(5):592-600 (2009).
Kim et al., "Potent VEGF Blockade Causes Regression of Coopted Vessels in a Model of Neuroblastoma," *Proc. Nat'l Acad. Sci.*, 99(17):11399-11404 (2002).
Lucentis Label (Revised 2006).
Lucentis Label (Revised 2014).
Ni & Hui, "Emerging Pharmacologic Therapies for Wet Age-Related Macular Degeneration," *Ophthalmologica*, 223:401-410 (Published Online First May 20, 2009).
Parkins & Lashmar, "The formulation of biopharmaceutical products," *Pharmaceutical Science & Technology Today*, 3(4):129-137 (Apr. 4, 2000).
Raptiva Label (Final Labelling Mar. 13, 2009).
Regeneron Pharmaceuticals Inc., Regeneron Reports Fourth Quarter and Full Year 2004 Financial and Operating Results. Media Release: Feb. 22, 2005.
Regeneron Pharmaceuticals Inc., Regeneron Reports Fourth Quarter and Full Year 2005 Financial and Operating Results. Media Release: Feb. 24, 2006.
Regeneron Pharmaceuticals Inc., Regeneron Reports Positive Phase 1 Data for the VEGF Trap in Age-Related Macular Degeneration; Preliminary Results Show Improvements in Vision and Reginal Swelling; VEGF Trap Was Well Tolerated at All Dose Levels. Media Release: May 1, 2006.
Reichert, "Antibody-Based Therapeutics to Watch in 2011," *MABS*, 3(1):76-99 (2011).
Remicade Label (Revised Nov. 2013).
Rogers et al., "The prevalence of retinal vein occlusion: pooled data from population studies from the United States, Europe, Asia, and Australia," *Ophthalmology*, 117(2):313-319e1 (2010).
Schmidt-Erfurth, "Current Concepts in the Management of Diabetic Macular Edema," *Johns Hopkins Advanced Studies in Ophthalmology*, 7(2):52-59 (2010).
Simulect Label (May 1998).
Spaide et al., "Prospective Study of Intravitreal Ranibizumab as a Treatment for Decreased Visual Acuity Secondary to Central Retinal Vein Occlusion," *Am. J. Ophthalmology*, 147(2):298-306 (2009).
Spielberg, L. & Leys, A., "Intravitreal Bevacizumab for Myopic Choroidal Neovascularization: Short-Term and 1-Year Results," *Bulletin Societe Belge D'Ophtalmologie*, 312:17-27 (2009).
Steinbrook, "The Price of Sight—Ranibizumab, Bevacizumab, and the Treatment of Macular Degeneration," *N. Eng. J. Med.*, 355(14):1409-1412 (2006).
The Branch Vein Occlusion Study, G., "Argon laser photocoagulation for macular edema in branch vein occlusion," *Am. J. Ophthalmology*, 98(3):271-282 (1984).
U.S. Department of Health and Human Services, National Institute of Health, National Eye Institute, "Age-Related Macular Degeneration: What You Should Know," (Sep. 2015) https://www.nei.nih.gov/sites/default/files/healthpdfs/WYSK_AMD_English_Sept2015_PRINT.pdf.
U.S. Department of Health and Human Services, National Institute of Health, National Eye Institute, "Diabetic Retinopathy: What You Should Know," (Sep. 2015) https://www.nei.nih.gov/sites/default/files/2019-06/Diabetic-Retinopathy-What-You-Should-Know-508.pdf.
U.S. Department of Health and Human Services, Office of Inspector General, "Questionable Billing for Medicare Ophthalmology Services" Sep. 2015 OEI-04-12-00280.
Xolair Label (2003).
Heier, J., "Intravitreal VEGF Trap for AMD: An Update, The Clear-It 2 Extension Study" Presented at the annual meeting of the Association for Research in Vision and Ophthalmology, Retina Today (2009) pp. 44-45.
Berker et al., "Surgical treatment of central retinal vein occlusion," *Acta Ophthalmol.*, 86:245-252 (2008).

(56) References Cited

OTHER PUBLICATIONS

Byeon et al., Short-Term Results of Intravitreal Bevacizumab for Macular Edema with Retinal Vein Obstruction and Diabetic Macular Edema, *J. Ocular Pharmacology and Therapeutics*, 23(4):387-394 (Nov. 2007).
ClinicalTrials.gov, "1997: Congress Passes Law (FDAMA) Requiring Trial Registration," (1997), https://clinicaltrials.gov/ct2/about-site/history, submitted in IPR2023-00099 as Exhibit 1085 (last updated May 2021).
Corrections to Kiire et al., "Managing Retinal Vein Occlusion," *BMJ*, 344(e2110):1 (2012).
Expert Declaration of Dr. Jay M. Stewart in Support of Petition for Inter Partes Review of U.S. Pat. No. 10,857,205 B2, dated Oct. 27, 2022, in IPR2023-00099.
Expert Declaration of Mary Gerritsen, Ph.D. in Support of Petition for Inter Partes Review of U.S. Pat. No. 10,857,205 B2, dated Oct. 27, 2022, in IPR2023-00099.
Gewaily et al., "Intravitreal steroids versus observation for macular edema secondary to central retinal vein occlusion," *Cochrane Database Syst. Rev.*, 1(CD007324):1-31 (2009).
Golan et al., "Current Treatment of Retinal Vein Occlusion," *Eur. Ophthalmic Rev.*, 5:62-68 (2011).
Keane et al., "Retinal vein occlusion and macular edema—critical evaluation of the clinical value of ranibizumab," *Clinical Ophthalmology*, 5:771-781 (2011).
Kiire et al., "Managing retinal vein occlusion," *BMJ*, 344(e499):1-16 (Feb. 2012).
Kinge et al., "Efficacy of Ranibizumab in Patients With Macular Edema Secondary to Central Retinal Vein Occlusion: Results From the Sham-Controlled ROCC Study," *American Journal of Ophthalmology*, 150(3):310-314 (2010).
Kreatsoulas, "Expanding Therapeutic Options for Retinal Vein Occlusion," *Retina Today*, pp. 20-21 (Jul./Aug. 2009).
Petition for Inter Partes Review of U.S. Pat. No. 10,857,205 B2, dated Oct. 28, 2022, in IPR2023-00099.
Pieramici, "Intravitreal Ranibizumab for Treatment of Macular Edema Secondary to Retinal Vein Occlusion," *Retina Today*, 44-46 (Mar. 2009).
Regeneron Pharmaceuticals, Inc., "Bayer and Regeneron Extend Development Program for VEGF Trap-Eye to Include Central Retinal Vein Occlusion," Press Release, (Apr. 30, 2009), https://investor.regeneron.com/news-releases/news-release-details/bayer-and-regeneron-extend-development-program-vegf-trap-eye, submitted in IPR2023-00099 as Exhibit 1028 (last accessed Nov. 4, 2022).
Regeneron Pharmaceuticals, Inc., "Regeneron and Bayer HealthCare Announce Encouraging 32-Week Follow Up Results from a Phase 2 Study of VEGF Trap-Eye in Age-Related Macular Degeneration," Press Release, (Apr. 28, 2008), http://newsroom.regeneron.com/releasedetail.cfm?releaseid=394066, submitted in IPR2023-00099 as Exhibit 1012 (last accessed Nov. 11, 2022).
Regeneron Pharmaceuticals, Inc., "Regeneron Reports Third Quarter 2010 Financial Results and Business Highlights," Press Release (Oct. 28, 2010) https://investor.regeneron.com/news-releases/news-release-details/regeneron-reports-third-quarter-2010-financial-results-and, submitted in IPR2023-00099 as Exhibit 1058 (last accessed Nov. 4, 2022).
Regeneron Pharmaceuticals, Inc., Quarterly Report Pursuant to Section 13 or 15(d) of the Securities Exchange Act of 1934 (Form 10-Q), submitted in IPR2023-00099 as Exhibit 1021 (Sept. 30, 2009).
Regeneron Pharmaceuticals, Inc., Quarterly Report Pursuant to Section 13 or 15(d) of the Securities Exchange Act of 1934 (Form 10-Q), submitted in IPR2023-00099 as Exhibit 1022 (Sep. 30, 2010).
Shahid et al., "The Management of Retinal Vein Occlusion: is Interventional Ophthalmology the Way Forward?," *Br. J. Ophthalmology*, 90:627-639 (2006).

Sophie et al., "Aflibercept: a Potent Vascular Endothelial Growth Factor Antagonist for Neovascular Age-Related Macular Degeneration and Other Retinal Vascular Diseases," *Biol. Ther.*, 2(3):1-22 (2012).
Wu et al., "Comparison of Two Doses of Intravitreal Bevacizumab (Avastin) for Treatment of Macular Edema Secondary to Branch Retinal Vein Occlusion," *Retina*, 28:212-219 (2008).
Final Written Decision Determining All Challenged Claims Unpatentable Denying Petitioner's Motion to Exclude Evidence Denying in part and Dismissing in Part Patent Owner's Motion to Exclude Evidence dated Nov. 9, 2022, in IPR2021-00880 dated Nov. 9, 2022, for U.S. Pat. No. 9,669,069 B2.
Final Written Decision Determining All Challenged Claims Unpatentable Denying in part and Dismissing in part Petitioners' Motion to Exclude Denying in part and Dismissing in part Denying Patent Owner's Motion to Exclude dated Nov. 9, 2022, in IPR2021-00881 dated Nov. 9, 2022, for U.S. Pat. No. 9,254,338 B2.
American Academy of Ophthalmology, "What is a Slit Lamp," https://www.aao.org/eye-health/treatments/what-is-slit-lamp (Apr. 23, 2018) (accessed Jan. 1, 2023), submitted in IPR2023-00442 as Exhibit 1039.
Brown et al., "Polypeptides and Proteins," in *Organic Chemistry* (Fourth Ed.), Thomson Brooks/Cole (CA), Chapter 27.3, pp. 1075-1096 (2005).
Chakravarthy et al., "Ranibizumab versus Bevacizumab to Treat Neovascular Age-related Macular Degeneration: One-Year Findings from the IVAN Randomized Trial," *Ophthalmology*, 119(7): pp. 1399-1411 (Jul. 2012).
ClinicalTrials.gov Archive, History of Changes for Study: NCT00090623, "A Study of rhuFab V2 (Ranibizumab) in Subjects With Subfoveal Choroidal Neovascularization Secondary to Age-Related Macular Degeneration (AMD)," Version 1 https://clinicaltrials.gov/ct2/history/NCT00090623?V_1=View#StudyPageTop (Jun. 23, 2005) (accessed Jan. 2, 2023), submitted in IPR2023-00442 as Exhibit 1053.
ClinicalTrials.gov Archive, History of Changes for Study: NCT00685854, "Pilot Study of Intravitreal Injection of Ranibizumab for Macular Telangiectasia With Neovascularization (MACTEL 2)," Version 01 https://clinicaltrials.gov/ct2/history/NCT00685854?V1=View#StudyPageTop (May 24, 2008) (accessed Jan. 6, 2023), submitted in IPR2023-00442 as Exhibit 1032.
ClinicalTrials.gov, "About the Results Database," https://clinicaltrials.gov/ct2/about-site/results (Mar. 2018) (accessed Jan. 1, 2023), submitted in IPR2023-00442 as Exhibit 1050.
ClinicalTrials.gov, "Background," https://clinicaltrials.gov/ct2/about-site/background (May 2021) (accessed Jan. 1, 2023), submitted in IPR2023-00442 as Exhibit 1049.
ClinicalTrials.gov, "How to Read a Study Record," https://clinicaltrials.gov/ct2/help/how-read-study (May 2021) (accessed Jan. 1, 2023), submitted in IPR2023-00442 as Exhibit 1051.
ClinicalTrials.gov, Study: NCT00593450, "Comparison of Age-related Macular Degeneration Treatments Trials: Lucentis-Avastin Trial," Version 25, https://clinicaltrials.gov/ct2/show/NCT00593450 (Aug. 21, 2017) (accessed Jan. 1, 2023), submitted in IPR2023-00442 as Exhibit 1035.
ClinicalTrials.gov, Study: NCT00685854, "Ranibizumab Injections to Treat Macular Telangiectasia Without New Blood Vessel Growth," https://web.archive.org/web/20081107014243/https://clinicaltrials.gov/ct2/show/NCT00685854 (Apr. 2008) (accessed Jan. 6, 2023), submitted in IPR2023-00442 as Exhibit 1033.
ClinicalTrials.gov, Study: NCT00685854, "Ranibizumab Injections to Treat Macular Telangiectasia Without New Blood Vessel Growth," Version 23, https://clinicaltrials.gov/ct2/show/NCT00685854 (Jul. 2, 2017) (accessed Jan. 1, 2023), submitted in IPR2023-00442 as Exhibit 1044.
Expert Declaration of Diana V. Do, M.D., dated Oct. 11, 2022, in IPR2022-01225.
Expert Declaration of Dr. Edward Chaum in Support of Petition for Inter Partes Review of U.S. Pat. No. 10,130,681, dated Jan. 6, 2023, in IPR2023-00442.
Halpern et al., "Resource utilization and costs of age-related macular degeneration," *Health Care Financ. Rev.*, 27(3): pp. 37-47 (Spring 2006).

(56) References Cited

OTHER PUBLICATIONS

Hashmi et al., "Conjunctivitis," in *StatPearls*, Treasure Island (FL), StatPearls Publishing, https://www.ncbi.nlm.nih.gov/books/NBK541034/ (published online Jan. 2022, updated Dec. 6, 2022) (accessed Jan. 5, 2023), submitted in IPR2023-00442 as Exhibit 1024.
Internet Archive, "CATT Patient Eligibility Criteria," https://web.archive.org/web/20100713035617/http://www.med.upenn.edu/cpob/studies/documents/CATTEligibilityCriteria_000.pdf (Jul. 13, 2010) (accessed Dec. 8, 2022), submitted in IPR2023-00442 as Exhibit 1031.
IPR2021-00880, 00881, Record of Oral Hearing in *Mylan Pharmaceuticals Inc. v. Regeneron Pharmaceuticals, Inc.*, dated Aug. 10, 2022, submitted in IPR2023-00442 as Exhibit 1055.
IPR2022-00298, Paper 1, Petition for IPR (Dec. 9, 2021), submitted in IPR2022-01524 as Exhibit 2032.
IPR2022-00301, Paper 1, Petition for IPR (Dec. 9, 2021), submitted in IPR2022-01524 as Exhibit 2030.
IPR2022-01225, Preliminary Response of Patent Owner (Oct. 13, 2022).
IPR2022-01226, Preliminary Response of Patent Owner (Oct. 13, 2022).
IPR2022-01524, Preliminary Response of Patent Owner (Dec. 23, 2022).
IPR2023-00442, Paper 1, Petition for IPR (Jan. 6, 2023).
Jaffe et al., *Intraocular Drug Delivery*, Taylor & Francis Group (NY) (2006).
Li et al., "Treatment regimens for administration of anti-vascular endothelial growth factor agents for neovascular age-related macular degeneration," *Cochrane Database Syst. Rev.*, Issue 5, Article CD012208, pp. 1-91 (2020).
Lott et al., "Bevacizumab in Inflammatory Eye Disease," *American Journal of Ophthalmology*, 148(5): pp. 711-717.e2 (Nov. 2009).
Mansour et al., "Long-term Visual Outcomes of Intravitreal Bevacizumab in Inflammatory Ocular Neovascularization," *American Journal of Ophthalmology*, 148(2): pp. 310-316.e2 (Aug. 2009).
Martin et al., "Ranibizumab and Bevacizumab for Treatment of Neovascular Age-related Macular Degeneration: Two-Year Results," *Ophthalmology*, 119(7): pp. 1388-1398 (Jul. 2012).
National Health Service, "Overview: Uveitis," https://www.nhs.uk/conditions/uveitis/ (Jan. 3, 2020) (accessed Jan. 5, 2023), submitted in IPR2023-00442 as Exhibit 1063.
Prevent Blindness, "Uveitis: What is Uveitis?" https://preventblindness.org/wp-content/uploads/2021/06/FS119-Uveitisshort.pdf (accessed Jan. 6, 2023), submitted in IPR2023-00442 as Exhibit 1023.
Retinal Physician, "Steps for a Safe Intravitreal Injection Technique," https://www.retinalphysician.com/issues/2009/july-aug/steps-for-a-safe-intravitreal-injection-technique (Jul. 1, 2009) (accessed Dec. 7, 2023), submitted in IPR2023-00442 as Exhibit 1041.
Transcript of Deposition of Thomas Albini, M.D., dated Jan. 20, 2022, in IPR2021-00880 and IPR2021-00881.
Decision Granting Institution of Inter Partes Review in IPR2022-01225 dated Jan. 11, 2023, for U.S. Pat. No. 10,130,681 B2.
Decision Granting Institution of Inter Partes Review in IPR2022-01226 dated Jan. 11, 2023, for U.S. Pat. No. 10,888,601 B2.
Abraham et al., "Randomized, Double-Masked, Sham-Controlled Trial of Ranibizumab for Neovascular Age-Related Macular Degeneration: PIER Study Year 2," *Am. J. Ophthalmology*, 150(3), pp. 315-324.e1 (Sep. 2010).
Adamis, "Ocular Angiogenesis: Vascular Endothelial Growth Factor and Other Factors," in *Retinal Pharmacotherapy* 23, Nguyen et al., eds., (2010).
American Academy of Ophthalmology, "Anti-VEGF Treatments," https://www.aao.org/eye-health/drugs/anti-vegf-treatments (accessed Nov. 8, 2021).
American Academy of Ophthalmology, "Bevacizumab," https://eyewiki.aao.org/Bevacizumab (accessed Nov. 2, 2021).
American Academy of Ophthalmology, "Ophthalmology Subspecialists," Jun. 6, 2016, https://www.aao.org/eye-health/tips-prevention/ophthalmology-subspecialists (accessed Sep. 26, 2022).
American Academy of Ophthalmology, "Retinal Vasculitis," https://eyewiki.aao.org/Retinal_Vasculitis (accessed Jan. 13, 2022).
American Academy of Ophthalmology, "What is Avastin," https://www.aao.org/eye-health/drugs/avastin (accessed Nov. 9, 2021).
American Academy of Ophthalmology, "What is Eylea," https://www.aao.org/eye-health/drugs/what-is-eylea (accessed Nov. 9, 2021).
American Academy of Ophthalmology, "What is Lucentis," https://www.aao.org/eye-health/drugs/lucentis (accessed Nov. 9, 2021).
American Society of Retina Specialists, "About Us," https://www.asrs.org/about (accessed Dec. 6, 2021).
American Society of Retina Specialists, "Age-Related Macular Degeneration," https://www.asrs.org/patients/retinal-diseases/2/agerelated-macular-degeneration (accessed Dec. 30, 2021).
American Society of Retina Specialists, "Branch Retinal Vein Occlusion," https://www.asrs.org/patients/retinal-diseases/24/branch-retinal-vein-occlusion (accessed Dec. 30, 2021).
American Society of Retina Specialists, "Central Retinal Vein Occlusion," https://www.asrs.org/patients/retinal-diseases/22/central-retinal-vein-occlusion (accessed Dec. 30, 2021).
American Society of Retina Specialists, "Diabetic Retinopathy," https://www.asrs.org/patients/retinal-diseases/3/diabetic-retinopathy (accessed Dec. 30, 2021).
American Speech-Language-Hearing Association, "Calculating Medicare Fee Schedule Rates," https://www.asha.org/practice/reimbursement/medicare/calculating-medicare-fee-schedule-rates/ (accessed Nov. 22, 2021).
*Amgen v. F. Hoffman-La Roche, Ltd.*, Case No. 05-cv-12237 (D. Mass.), ECF 610-3, Declaration of Alexander M. Klibanov, Ph.D. in Support of Defendants' Opposition to Amgen's Motion for Summary Judgment of Infringement of '422 Claim 1, '933 Claim 3, and '698 Claim 6 (Jun. 28, 2007), cited in Deposition of Dr. Alexander M. Klibanov, Ph.D., on Mar. 24, 2022.
Amgen, "Fusion Protein," https://www.amgen.com/stories/2018/08/the-shape-of-drugs-to-come/fusion-protein (accessed Jan. 7, 2022).
Amino acid sequence alignment of SEQ ID No. 2 of the '338 and '069 patents with aflibercept amino acid sequence from WHO 2006, SEQ ID No. 16 of the '758 patent, and SEQ ID No. 16 of the '959 patent, submitted on May 27, 2022, in IPR2021-00881 as Exhibit 1122.
Amino acid sequence alignment of SEQ ID No. 2 of the '338 patent with SEQ ID No. 16 of the '758 patent and SEQ ID No. 4 of Dix, submitted in IPR2022-00881 as Exhibit 1093.
Amino acid sequence alignment of SEQ ID No. 2 of the '338 patent, aflibercept amino acid sequence from WHO 2006, and SEQ ID No. 2 of the '173 patent, cited in Deposition of Dr. Alexander M. Klibanov, Ph.D., on Mar. 24, 2022, submitted in IPR2021-00881 as Exhibit 1117.
Amino acid sequence alignment of SEQ ID No. 2 of the '681 and '601 patents with aflibercept amino acid sequence from WHO 2006, SEQ ID No. 16 of the '758 patent, and SEQ ID No. 16 of the '959 patent, submitted in IPR2022-01226 as Exhibit 1087.
Amino acid sequence alignment of SEQ ID No. 2 of the '681 and '601 patents with SEQ ID No. 16 of the '758 patent and SEQ ID No. 2 of the '173 patent, submitted in IPR2022-01226 as Exhibit 1092.
Annotated version of '338 patent claim 1, cited in Deposition of Dr. Diana V. Do, M.D., on Apr. 21, 2022.
ASRS Clinical Updates, "ASRS Fights Novitas [sic] Decision to Interpret Eylea Usage More Frequently than q8 as 'Off Label'," (May 24, 2016) (accessed Apr. 7, 2022), cited in Deposition of Dr. David M. Brown, M.D., on Apr. 26, 2022.
Avastin Label (revised 2004), https://www.accessdata.fda.gov/drugsatfda_docs/label/2004/125085lb1.pdf (accessed Sep. 26, 2022).
BasePair Biotechnologies, "What is an Aptamer?—Aptamers and SELEX," https://www.basepairbio.com/what-is-an-aptamer/ (accessed Dec. 30, 2021).
Batta et al., "Trends in FDA Drug Approvals Over Last 2 Decades: An Observational Study," *J. Family Medicine & Primary Care*, 9, pp. 105-114 (2020).

(56) References Cited

OTHER PUBLICATIONS

Bausch and Lomb, "Help Your Patients Obtain Access to Visudyne," https://www.bauschretinarx.com/visudyne/ecp/ordering/ (accessed Jan. 12, 2022).
Bausch and Lomb, "Visudyne," https://www.bauschretinarx.com/visudyne/ecp/about/ (accessed Dec. 2, 2021).
Bausch Health Companies, Form 10-K, 2020.
BCBS Florida, "Vascular Endothelial Growth Factor Inhibitors for Ocular Neovascularization," revised Apr. 1, 2022.
Beovu Label (revised Jun. 2020), https://www.accessdata.fda.gov/drugsatfda_docs/label/2020/761125s0041b1.pdf (accessed Sep. 26, 2022).
Beovu Label (revised Oct. 2019), https://www.accessdata.fda.gov/drugsatfda_docs/label/2019/761125s0001b1.pdf (accessed Sep. 26, 2022).
Bhisitkul et al., "Alternative anti-VEGF treatment regimens in exudative age-related macular degeneration," *Expert Rev. Ophthalmol.*, 5(6) (Jan. 2010).
Biospace, "Bayer HealthCare AG and Regeneron Pharmaceuticals, Inc. to Collaborate on VEGF Trap for the Treatment of Eye Diseases; Regeneron Retains U.S. Commercialization Rights, Receives $75 Million Upfront, and Eligible for up to $245 Million of Milestone Payments," (Oct. 19, 2006), https://www.biospace.com/article/releases/bayer-healthcare-ag-and-regeneron-pharmaceuticals-inc-to-collaborate-on-vegf-trap-for-the-treatment-of-eye-diseases-b-regeneron-b-retains-u-s-c/ (accessed Sep. 26, 2022).
Bork et al., "Increasing the Sialylation of Therapeutic Glycoproteins: The Potential of the Sialic Acid Biosynthetic Pathway," *J. Pharm. Sci.*, 98(10), pp. 3499-3508 (Oct. 2009).
Bright Focus Foundation, "Age-Related Macular Degeneration: Facts & Figures," https://www.brightfocus.org/macular/article/age-related-macular-facts-figures (accessed Nov. 5, 2021).
Brown et al., "Intravitreal Aflibercept Injection for Macular Edema Secondary to Central Retinal Vein Occlusion: 1-Year Results from the Phase 3 Copernicus Study", *Am. J. Ophthalmol.*, 155, pp. 329-437 (Mar. 2013).
Brown et al., "Ranibizumab Versus Verteporfin Photodynamic Therapy for Neovascular Age-Related Macular Degeneration: Two-Year Results of the Anchor Study," *Ophthalmology*, 116(1), pp. 57-65.e5 (Jan. 2009).
Calculator.net, "Sample Size Calculator," https://www.calculator.net/sample-size-calculator.html?type=2&c12=95&ss2=200&pc2=50&ps2=3000&x=68&y=18#findci (accessed Jan. 25, 2022).
Campochiaro et al., "Antagonism of Vascular Endothelial Growth Factor for Macular Edema Caused by Retinal Vein Occlusions: Two-Year Outcomes," *Ophthalmology*, 117(12), pp. 2387-2394.e5 (Dec. 2010) (online publication).
Cantu et al., "Thioesterases: A New Perspective Based on Their Primary and Tertiary Structures," *Protein Science*, 19(17), pp. 1281-1295 (Jul. 2010).
CAS registry for No. 862111-32-8, cited in Deposition of Dr. Alexander M. Klibanov, Ph.D., on Mar. 24, 2022.
Center for Drug Evaluation and Research, Approved Labeling for BLA Application No. 125156 (Lucentis) (2006).
Center for Drug Evaluation and Research, Medical Review for BLA Application No. 125387 (Nov. 18, 2011).
Center for Drug Evaluation and Research, Statistical Review for BLA Application No. 125387 (Nov. 18, 2011).
Centers for Disease Control and Prevention, "Vision Loss: A Public Health Problem," https://www.cdc.gov/visionhealth/basic_information/vision_loss.htm (accessed Jun. 12, 2020).
Centers for Medicare & Medicaid Services, "Medicare Physician & Other Practitioners—by Provider and Service," https://data.cms.gov/provider-summary-by-type-of-service/medicare-physician-other-practitioners/medicare-physician-other-practitioners-by-provider-and-service (accessed Nov. 19, 2021).
Centers for Medicare & Medicaid Services, "Payment Allowance Limits for Medicare Part B Drugs: Effective Oct. 1, 2012, through Dec. 31, 2012," (Oct. 2012), https://www.cms.gov/Medicare/Medicare-Fee-for-Service-Part-B-Drugs/McrPartBDrugAvgSalesPrice/2012ASPFiles (accessed Sep. 26, 2022).
Centers for Medicare & Medicaid Services, "Payment Allowance Limits for Medicare Part B Drugs: Effective Oct. 1, 2013, through Dec. 31, 2013," (Oct. 2013), https://www.cms.gov/Medicare/Medicare-Fee-for-Service-Part-B-Drugs/McrPartBDrugAvgSalesPrice/2013ASPFiles (accessed Sep. 26, 2022).
Centers for Medicare & Medicaid Services, "Payment Allowance Limits for Medicare Part B Drugs: Effective Oct. 1, 2014, through Dec. 31, 2014," (Oct. 2014), https://www.cms.gov/Medicare/Medicare-Fee-for-Service-Part-B-Drugs/McrPartBDrugAvgSalesPrice/2014ASPFiles (accessed Sep. 26, 2022).
Centers for Medicare & Medicaid Services, "Payment Allowance Limits for Medicare Part B Drugs: Effective Oct. 1, 2015, through Dec. 31, 2015," (Oct. 2015), https://www.cms.gov/Medicare/Medicare-Fee-for-Service-Part-B-Drugs/McrPartBDrugAvgSalesPrice/2015ASPFiles (accessed Sep. 26, 2022).
Centers for Medicare & Medicaid Services, "Payment Allowance Limits for Medicare Part B Drugs: Effective Oct. 1, 2016, through Dec. 31, 2016," (Oct. 2016), https://www.cms.gov/Medicare/Medicare-Fee-for-Service-Part-B-Drugs/McrPartBDrugAvgSalesPrice/2016ASPFiles (accessed Sep. 26, 2022).
Centers for Medicare & Medicaid Services, "Payment Allowance Limits for Medicare Part B Drugs: Effective Oct. 1, 2017, through Dec. 31, 2017," (Oct. 2017), https://www.cms.gov/Medicare/Medicare-Fee-for-Service-Part-B-Drugs/McrPartBDrugAvgSalesPrice/2017ASPFiles (accessed Sep. 26, 2022).
Centers for Medicare & Medicaid Services, "Payment Allowance Limits for Medicare Part B Drugs: Effective Oct. 1, 2018, through Dec. 31, 2018," (Oct. 2018), https://www.cms.gov/Medicare/Medicare-Fee-for-Service-Part-B-Drugs/McrPartBDrugAvgSalesPrice/2018ASPFiles (accessed Sep. 26, 2022).
Centers for Medicare & Medicaid Services, "Payment Allowance Limits for Medicare Part B Drugs: Effective Oct. 1, 2019, through Dec. 31, 2019," (Oct. 2019), https://www.cms.gov/Medicare/Medicare-Fee-for-Service-Part-B-Drugs/McrPartBDrugAvgSalesPrice/2019ASPFiles (accessed Sep. 26, 2022).
Centers for Medicare & Medicaid Services, "Payment Allowance Limits for Medicare Part B Drugs: Effective Oct. 1, 2020, through Dec. 31, 2020," (Oct. 2020), https://www.cms.gov/medicare/medicare-part-b-drug-average-sales-price/2020-asp-drug-pricing-files (accessed Sep. 26, 2022).
Centers for Medicare & Medicaid Services, "Payment Allowance Limits for Medicare Part B Drugs: Effective Oct. 1, 2021, through Dec. 31, 2021," (Oct. 2021), https://www.cms.gov/medicare/medicare-part-b-drug-average-sales-price/2021-asp-drug-pricing-files (accessed Sep. 26, 2022).
Centers for Medicare & Medicaid Services, "Physician Fee Schedule," https://www.cms.gov/Medicare/Medicare-Fee-for-Service-Payment/PhysicianFeeSched (accessed Nov. 22, 2021).
Centers for Medicare & Medicare Services, "2021 ASP Drug Pricing Files," https://www.cms.gov/medicare/medicare-part-b-drug-average-sales-price/2021-asp-drug-pricing-files (accessed Nov. 22, 2021).
Centers for Medicare & Medicare Services, "Medicare Part B Drug Average Sales Price," https://www.cms.gov/Medicare/Medicare-Fee-for-Service-Part-B-Drugs/McrPartBDrugAvgSalesPrice (accessed Dec. 8, 2021).
Chen et al., "Carboxylic ester hydrolases: Classification and database derived from their primary, secondary, and tertiary structures," *Protein Science*, 25(11), pp. 1942-1953 (Nov. 2016).
Christensen, "Methodology of Superiority vs. Equivalence Trials and Non-Inferiority Trials," *J. Hepatology*, 46(5), pp. 947-954 (May 2007) (online publication).
Clark et al., "Treatment Paradigms in AMD Management: Assessing Consistent Long-Term Dosing," *Retina Today Supp.*, pp. 1-16 (Sep. 2017), cited in Deposition of Dr. David M. Brown, M.D., on Apr. 26, 2022.
ClinicalTrials.gov Archive, History of Changes for Study: NCT00473330, "A Study of Ranibizumab Injection in Subjects With Clinically Significant Macular Edema (ME) With Center Involvement Secondary to Diabetes Mellitus (RISE)," Version 13, dated Mar. 21, 2017, submitted in IPR2021-00881 as Exhibit 2122.

(56) References Cited

OTHER PUBLICATIONS

ClinicalTrials.gov Archive, History of Changes for Study: NCT00473382, "A Study of Ranibizumab Injection in Subjects With Clinically Significant Macular Edema (ME) With Center Involvement Secondary to Diabetes Mellitus (RIDE)," Version 13, dated Mar. 21, 2017, submitted in IPR2021-00881 as Exhibit 2123.

ClinicalTrials.gov Archive, History of Changes for Study: NCT00485836, "A Study of the Efficacy and Safety of Ranibizumab Injection in Patients With Macular Edema Secondary to Central Retinal Vein Occlusion (CRUISE)," Version 10, dated Jun. 29, 2017, submitted in IPR2021-00881 as Exhibit 2125.

ClinicalTrials.gov Archive, History of Changes for Study: NCT00486018, "A Study of the Efficacy and Safety of Ranibizumab Injection in Patients With Macular Edema Secondary to Branch Retinal Vein Occlusion (BRAVO)," Version 12, dated Apr. 4, 2017, submitted in IPR2021-00881 as Exhibit 2124.

ClinicalTrials.gov Archive, History of Changes for Study: NCT00519285, "Aflibercept in Combination With Docetaxel in Metastatic Androgen Independent Prostate Cancer (Venice)," Version 01, dated Aug. 21, 2007, submitted in IPR2021-00881 as Exhibit 2078.

ClinicalTrials.gov Archive, History of Changes for Study: NCT00644124, "Aflibercept and Standard Chemotherapy (R-CHOP) in First Line of Non Hodgkin B-Cell Lymphoma," Version 01, dated Mar. 21, 2008, submitted in IPR2021-00881 as Exhibit 2079.

ClinicalTrials.gov Archive, History of Changes for Study: NCT00794417, "A Study of Aflibercept Administered in Combination With Pemetrexed and Cisplatin in Patients With Advanced Carcinoma," Version 01, dated Nov. 19, 2008, submitted in IPR2021-00881 as Exhibit 2053.

ClinicalTrials.gov Archive, History of Changes for Study: NCT01148615, "A Study of Intravenous Aflibercept With Docetaxel in Chinese Patients With Solid Tumors," Version 01, dated Jun. 21, 2010, submitted in IPR2021-00881 as Exhibit 2054.

ClinicalTrials.gov Archive, History of Changes for Study: NCT01486771, "Macugen for Proliferative Diabetic Retinopathy Study With Extended Dosing (M-PDRS ED)," Version 01, dated Dec. 5, 2011, submitted in IPR2021-00881 as Exhibit 2109.

ClinicalTrials.gov Archive, History of Changes for Study: NCT01940900, "A Phase 3 Safety and Efficacy Study of Fovista (E10030) Intravitreous Administration in Combination With Lucentis Compared to Lucentis Monotherapy," Version 21, dated Aug. 13, 2018, submitted in IPR2021-00881 as Exhibit 2025.

ClinicalTrials.gov Archive, History of Changes for Study: NCT01944839, "A Phase 3 Safety and Efficacy Study of Fovista (E10030) Intravitreous Administration in Combination With Lucentis Compared to Lucentis Monotherapy," Version 27, dated Aug. 8, 2018, submitted in IPR2021-00881 as Exhibit 2024.

ClinicalTrials.gov Archive, History of Changes for Study: NCT02247479, "A Study Investigating the Efficacy and Safety of Lampalizumab Intravitreal Injections in Participants With Geographic Atrophy Secondary to Age-Related Macular Degeneration (CHROMA)," Version 60, dated Jun. 17, 2019, submitted in IPR2021-00881 as Exhibit 2021.

ClinicalTrials.gov Archive, History of Changes for Study: NCT02247531, "A Study Investigating the Safety and Efficacy of Lampalizumab Intravitreal Injections in Participants With Geographic Atrophy Secondary to Age-Related Macular Degeneration (SPECTRI)," Version 60, dated Oct. 14, 2019, submitted in IPR2021-00881 as Exhibit 2020.

ClinicalTrials.gov Archive, History of Changes for Study: NCT03577899, "Efficacy and Safety Trial of Conbercept Intravitreal Injection for Neovascular AMD(PANDA-1)," Version 06, dated Jun. 23, 2021, submitted in IPR2021-00881 as Exhibit 2023.

ClinicalTrials.gov Archive, History of Changes for Study: NCT03630952, "Efficacy and Safety Trial of Conbercept Intravitreal Injection for Neovascular AMD(PANDA-2)," Version 07, dated Jun. 22, 2021, submitted in IPR2021-00881 as Exhibit 2022.

ClinicalTrials.gov, "1997: Congress Passes Law (FDAMA) Requiring Trial Registration," https://clinicaltrials.gov/ct2/about-site/history (accessed Apr. 26, 2021).

ClinicalTrials.gov, "What Is ClinicalTrials.gov?" https://www.clinicaltrials.gov/ct2/about-site/background (accessed Jan. 20, 2021).

CloudResearch, "Determining Sample Size: How Many Survey Participants Do You Need?" https://www.cloudresearch.com/resources/guides/statistical-significance/determine-sample-size/ (accessed Jan. 25, 2022).

CMS.gov Medicare Coverage Database, "Billing and Coding: Aflibercept (Eylea)," https://www.cms.gov/medicare-coverage-database/view/article.aspx?articleid=53387&ver=28&keyword=&keywordType=starts&areaId=all&docType=6,3,5,1,F,P&contractOption=all&hcpcsOption=code&hcpcsStartCode=J0178&hcpcsEndCode=J0178&sortBy=title&bc=1 (accessed Apr. 22, 2021).

Cobo et al., "The Clearance of Intravitreal Gentamicin," *Am. J. Ophthalmology*, 92(1), pp. 59-62 (1981).

Complaint, *Horizon Healthcare Servs., Inc.* v. *Regeneron Pharms., Inc.*, No. 1:22-cv-10493-FDS (D. Mass. Apr. 4, 2022), ECF Nos. 1-1-18.

Complaint, *United States* v. *Regeneron Pharms., Inc.*, No. 1:20-cv-11217-FDS (D. Mass. Jun. 24, 2020), ECF Nos. 1-1-39.

Corporate Finance Institute, "SEC Filings—Requirements for Public Companies & Where to Find Them," https://corporatefinanceinstitute.com/resources/data/public-filings/sec-filings/ (accessed Jan. 20, 2021).

Cousins, "Controversies in the Long-term Management of Neovascular AMD: The Role of Imaging in Clinical Decision Making," *Retinal Physician* (Jan. 1, 2010), https://www.retinalphysician.com/issues/2010/jan-feb/controversies-in-the-long-term-management-of-neova (accessed Sep. 26, 2022).

Cruz, "PIER Data Suggest a Need for Tailored Injection Schedule," *Ocular Surgery News*, (Sep. 1, 2006), https://www.healio.com/news/ophthalmology/20120331/pier-data-suggest-a-need-for-tailored-injection-schedule (accessed Feb. 10, 2022).

Dadgostar et al., "Evaluation of Injection Frequency and Visual Acuity Outcomes for Ranibizumab Monotherapy in Exudative Age-related Macular Degeneration," *Ophthalmology*, 116, pp. 1740-1747 (2009).

Declaration of Doris Weber dated Mar. 7, 2022, in IPR2021-00881.

Demarest et al., "Optimization of the Antibody $C_H3$ Domain by Residue Frequency Analysis of IgG Sequences," *J. Mol. Biol.*, 335(1), pp. 41-48 (Jan. 2004).

Do et al., "Pharmacokinetic Study of Intravitreal Aflibercept in Humans with Neovascular Age-Related Macular Degeneration," *Retina*, 00, pp. 1-5 (2019), also available as Retina, 40(4), pp. 643-647 (Apr. 2020).

Donohue et al., "A Decade of Direct-to-Consumer Advertising of Prescription Drugs," *The New England Journal of Medicine*, 35(7), pp. 673-681 (Aug. 2007).

Donohue et al., "Effect of Direct-to-Consumer Advertising on Medication Choice: The Case of Antidepressants," Journal of Public Policy & Marketing, 23(2), pp. 115-127 (Sep. 2004).

Dreyfuss et al., "Ocular Angiogenesis," *Journal of Ophthalmology*, 2015, pp. Article ID 892043 (Sep. 2015).

Drugs.com, "Eylea FDA Approval History," https://www.drugs.com/history/eylea.html (accessed Nov. 16, 2021).

Drugs.com, "FDA Approves Eylea for Wet Age-Related Macular Degeneration," (Nov. 18, 2011), https://www.drugs.com/newdrugs/fda-approves-eylea-wet-age-related-macular-degeneration-2955.html (accessed Feb. 4, 2022).

Duncan et al., "Inhibition of Vascular Endothelial Growth Factor in the Primate Ovary Up-Regulates Hypoxia-Inducible Factor-1α in the Follicle and Corpus Luteum," *Endocrinology*, 149, pp. 3313-3320 (Apr. 2008) (online publication), cited in Deposition of Dr. Alexander M. Klibanov, Ph.D., on Mar. 24, 2022.

Elvidge, "Opthotech's Fovista crashes out in wet AMD," *Biopharmadive* (Aug. 14, 2017), available at https://www.biopharmadive.com/news/opthotech-fovista-phase-3-failure-setback-novartis/449248/ (accessed Aug. 2, 2021).

Elyasi et al., "Diabetic Macular Edema: Diagnosis and Management," EyeNet Magazine, May 2021: 35-37 (May 2021).

EP Patent Application No. 3 222 285 File History.

(56) References Cited

OTHER PUBLICATIONS

Ex. (a)(1)(a) to Tender Offer Statement to Momenta, filed with SEC on Sep. 2, 2020.

Excerpts from J.M. Berg et al., Biochemistry (5$^{th}$ Ed. 2002).

Expert Declaration of Angelo P. Tanna, M.D., dated Sep. 6, 2022, in IPR2022-01524.

Expert Declaration of David M. Brown, M.D., dated Feb. 10, 2022, in IPR2021-00880 and IPR2021-00881.

Expert Declaration of Dr. Alexander M. Klibanov, Ph.D., dated Feb. 8, 2022, in IPR2021-00880 and IPR2021-00881—[[Redacted]].

Expert Declaration of Dr. Diana V. Do, M.D., dated Feb. 10, 2022, in IPR2021-00881.

Expert Declaration of Dr. Lucian V. Del Priore, M.D., Ph.D., dated Feb. 9, 2022, in IPR2021-00880 and IPR2021-00881—[[Redacted]].

Expert Declaration of Dr. Thomas A. Albini in Support of Petition for Inter Partes Review of U.S. Pat. No. 10,130,681 B2, dated Jun. 30, 2022, in IPR2022-01225.

Expert Declaration of Dr. Thomas A. Albini in Support of Petition for Inter Partes Review of U.S. Pat. No. 10,888,601 B2, dated Jun. 30, 2022, in IPR2022-01226.

Expert Declaration of Dr. Thomas A. Albini in Support of Petitioner's Reply, dated May 27, 2022, in IPR2021-00881.

Expert Declaration of Ivan T. Hofmann Support of Petitioner's Reply, dated May 27, 2022, in IPR2021-00881—[[Redacted]].

Expert Declaration of Mary Gerritsen, Ph.D. in Support of Petition for Inter Partes Review of U.S. Pat. No. 10,130,681 B2, dated Jun. 30, 2022, in IPR2022-01225.

Expert Declaration of Mary Gerritsen, Ph.D. in Support of Petition for Inter Partes Review of U.S. Pat. No. 10,888,601 B2, dated Jun. 30, 2022, in IPR2022-01226.

Expert Declaration of Mary Gerritsen, Ph.D. in Support of Petitioner's Reply, dated May 26, 2022, in IPR2021-00881.

Expert Declaration of Richard Manning, Ph.D., dated Feb. 11, 2022, in IPR2021-00881—[[Redacted]].

Eye Care Surgery Center, "Macular Degeneration," https://www.eyecaresurgerycenterbr.com/diabetes-retina/macular-degeneration/ (accessed Nov. 18, 2021).

EyeGuru.org, "Intravitreal Injection Standard Dosing Table," https://eyeguru.org/blog/intravitreal-injection-dosing/ (accessed Dec. 6, 2021).

Eylea Label (revised Mar. 2021), https://www.accessdata.fda.gov/drugsatfda_docs/label/2021/125387s0691b1.pdf (accessed Sep. 26, 2022).

Eylea Label (revised May 2016), https://www.accessdata.fda.gov/drugsatfda_docs/label/2016/125387s0511b1.pdf (accessed Sep. 26, 2022).

Eylea Label (revised Oct. 2014), https://www.accessdata.fda.gov/drugsatfda_docs/label/2014/125387s0431b1.pdf (accessed Sep. 26, 2022).

Eylea Label (revised Sep. 2012), https://www.accessdata.fda.gov/drugsatfda_docs/label/2012/125387s0041b1.pdf (accessed Sep. 26, 2022).

Eylea, "Wet AMD: Dosing Flexibility," https://hcp.eylea.us/about/wet-amd-dosing/ (accessed Jan. 5, 2022).

Eylea Approval Letter (Nov. 18, 2011).

Fauser et al., "Suppression of Intraocular Vascular Endothelial Growth Factor During Aflibercept Treatment of Age-Related Macular Degeneration," *Am. J. Ophthalmology*, 158, pp. 532-536 (2014).

FDA Center for Drug Evaluation and Research, "Application No. 125387Orig1s000 [Eylea] Summary Review," https://www.accessdata.fda.gov/drugsatfda_docs/nda/2011/125387Orig1s000SumR.pdf (accessed May 20, 2022).

FDA, "Drugs@FDA: FDA-Approved Drugs, BLA 125387," https://www.accessdata.fda.gov/scripts/cder/daf/index.cfm?event=overview.process&ApplNo=125387 (accessed May 18, 2022).

FDA, "22 Case Studies Where Phase 2 and Phase 3 Trials Had Divergent Results" (Jan. 2017), submitted in IPR2021-00881 as Exhibit 1146.

FDA, "Guidance for Industry: Expedited Programs for Serious Conditions—Drugs and Biologics" (May 2014), https://www.fda.gov/media/86377/download (accessed Sep. 26, 2022).

FDA, "Macugen Drug Approval Package Page," Mar. 23, 2005, https://www.accessdata.fda.gov/drugsatfda_docs/nda/2004/21-756_Macugen.cfm (accessed Jan. 12, 2022).

FDA, "Non-Inferiority Clinical Trials to Establish Effectiveness: Guidance for Industry" (Nov. 2016), submitted in IPR2021-00881 as Exhibit 2097.

FDA, "Purple Book Database of Licensed Biological Products," https://purplebooksearch.fda.gov/patent-list (accessed May 13, 2022).

Fernández-Ferreiro et al., "Preclinical PET Study of Intravitreal Injections," *Investigative Ophthalmology & Visual Science*, 58(7), pp. 2843-2851 (Jun. 2017).

Ferrara et al., "Development of ranibizumab, an anti-vascular endothelial growth factor antigen binding fragment, as therapy for neovascular age-related macular degeneration," *Retina*, 26(8), pp. 859-870 (Oct. 2006).

FiercePharma, "Beovu, Novartis," (Oct. 25, 2021), https://www.fiercepharma.com/special-report/beovu-novartis-top-10-drug-launch-disasters (accessed Dec. 30, 2021).

FiercePharma, "Novartis' Hot New Eye Drug Beovu Tied to Potential Vision Loss: Experts," (Feb. 24, 2020), https://www.fiercepharma.com/pharma/retinal-society-flags-serious-side-effect-for-novartis-beovu (accessed Dec. 30, 2021).

FiercePharma, "The Top 20 Drugs by Worldwide sales in 2020," (May 3, 2021), https://www.fiercepharma.com/special-report/top-20-drugs-by-2020-sales (accessed Sep. 26, 2022).

FocusVision, "Survey Sample Size: How Much Do I Need?" (Apr. 11, 2019), https://www.focusvision.com/blog/survey-sample-size-how-much-do-i-need/ (accessed Jan. 25, 2022).

Fraser et al., "The Role of Vascular Endothelial Growth Factor and Estradiol in the Regulation of Endometrial Angiogenesis and Cell Proliferation in the Marmoset," *Endocrinology*, 149(9), pp. 4413-4420 (May 2008) (electronic publication).

Gagnon et al., "The Cost of Pushing Pills: A New Estimate of Pharmaceutical Promotion Expenditures in the United States," *PLoS Medicine*, 5(1), pp. 29-33 (Jan. 2008).

Gallemore et al., "When Anti-VEGF Treatment Fails: Retina Specialists Are Charting New Territory and Learning How to Spot and React to Failed Anti-VEGF Therapy," *Rev. Ophthalmology*, (Mar. 2008).

Genentech, Inc., "FDA Green-Lights Genentech's Lucentis for Macular Edema following Retinal Vein Occlusion," Press Release, (Jun. 23, 2010), https://www.genengnews.com/news/fda-green-lights-genentechs-lucentis-for-macular-edema-following-retinal-vein-occlusion/ (accessed Jan. 12, 2022).

Genentech, Inc., "Genentech, Inc. Submits Biologies License Application for FDA Review of Lucentis™ in Wet Age-Related Macular Degeneration," Press Release, (Dec. 30, 2005), https://www.biospace.com/article/releases/genentech-inc-submitsbiologics-license-application-for-fda-review-of-lucentis-tm-in-wetage- related-macular-degeneration-/ (accessed Feb. 3, 2022).

Gomez-Manzano et al., "VEGF Trap Induces Antiglioma Effect at Different Stages of Disease," *Neuro-Oncology*, 10, pp. 940-945 (Dec. 2008), cited in Deposition of Dr. Alexander M. Klibanov, Ph.D., on Mar. 24, 2022.

Good Days, https://www.mygooddays.org/ (accessed May 18, 2022).

Guha et al., "The Economics of Commercial Success in Pharmaceutical Patent Litigation," *Landslide* 1(5) (2009).

Hachiya et al., "Increase in respiratory cost at high growth temperature is attributed to high protein turnover cost in Petunia x hybrida petals," *Plant, Cell, and Environment*, 30(10), pp. 1269-1283 (Oct. 2007).

Hanhart et al., Correspondence regarding "Fellow Eye Effect of Unilateral Intravitreal Anti-VEGF Injections in Eyes with Diabetic Macular Edema," *Eye*, 29, pp. 292-293 (Nov. 2014) (online publication), cited in Deposition of Dr. Alexander M. Klibanov, Ph.D., on Mar. 24, 2022.

Hayes, "SEC Filings: Forms You Need to Know," *Investopedia*, https://www.investopedia.com/articles/fundamental-analysis/08/sec-forms.asp (accessed Jan. 20, 2021).

(56) References Cited

OTHER PUBLICATIONS

HCPCS Codes, "HCPCS Codes," https://hcpcs.codes/ (accessed Jan. 6, 2022).
Healio, "Access to Retina Providers Shows No Geographic Bias in U.S.," (Mar. 12, 2019), https://www.healio.com/news/ophthalmology/20190312/access-to-retina-providers-shows-no-geographic-bias-in-us (accessed Dec. 6, 2021).
Hecht, "Ophthalmic Preparations," *Remington: The Science and Practice of Pharmacy*, vol. II, 19th edition, Chapter 89, pp. 1563-1576 (1995) (Easton, PA).
Heier & Focus Study Group, Abstract: *Intravitreal Ranibizumab (Lucentis™) with Verteporfin Photodynamic Therapy for Neovascular Age-Related Macular Degeneration: Year One Results*, Am. Soc'y Retina Specialists Ann. Meeting 94 (2005).
Heier et al., "Intravitreal Aflibercept (VEGF Trap-Eye) in Wet Age-related Macular Degeneration," *Ophthalmology*, 119, Appendices 2-8, pp. 1-34 (Dec. 2012), submitted in IPR2022-01524 as Exhibit 1030.
Heier, "VEGF Trap-Eye for Exudative AMD," *Retinal Physician*, (Apr. 2009).
Heimann, "Intravitreal Injections: Techniques and Sequelae," in *Medical Retina*, Holz & Spaide, eds., (2007) (New York, NY).
Helzner, "Lucentis After 1 Year: Doctors praise this practice-transforming therapy—but find drawbacks," *Retinal Physician* (Jul. 1, 2007), https://www.retinalphysician.com/issues/2007/july-aug/lucentis-after-1-year (accessed Sep. 26, 2022).
Highlights of Prescribing Information for Eylea (Revised: Jun. 2021), cited in Deposition of Dr. Richard Manning, Ph.D., on May 4, 2022, submitted in IPR2021-00881 as Exhibit 1152.
Hirokawa et al., "Tau Proteins: The Molecular Structure and Mode of Binding on Microtubules," *J. Cell Biol.*, 107(4), pp. 1449-1459 (Oct. 1988).
Hopkins Medicine, "Photodynamic Therapy for Age-Related Macular Degeneration," https://www.hopkinsmedicine.org/health/treatment-tests-and-therapies/photodynamic-therapy-for-agerelated-macular-degeneration (accessed Dec. 1, 2021).
Iacono et al., "Antivascular Endothelial Growth Factor in Diabetic Retinopathy," *Dev. Ophthalmol.*, 46, pp. 39-53 (2010).
IPR2021-00880, Corrected Patent Owner Response (Feb. 11, 2022).
IPR2021-00880, Patent Owner Sur-Reply (Jul. 6, 2022).
IPR2021-00880, Petitioner Reply (May 27, 2022)—[[Redacted]].
IPR2021-00881, Corrected Patent Owner Response (Feb. 11, 2022)—[[Redacted]].
IPR2021-00881, Patent Owner Sur-Reply (Jul. 6, 2022).
IPR2021-00881, Petitioner Reply (May 27, 2022)—[[Redacted]].
IPR2022-01225, Paper 1, Petition for IPR (Jul. 1, 2022).
IPR2022-01226, Paper 1, Petition for IPR (Jul. 1, 2022).
IPR2022-01524, Paper 1, Petition for IPR (Sep. 9, 2022).
IQVIA, "Available IQVIA Data," https://www.iqvia.com/insights/the-iqvia-institute/available-iqvia-data (accessed Jan. 18, 2022).
IQVIA, Form 10-K, 2020.
Jaffe et al., "Differential Response to Anti-VEGF Regimens in Age-Related Macular Degeneration Patients with Early Persistent Retinal Fluid," *Ophthalmology*, 123(9), pp. 1856-1864 (Sep. 2016).
Jager et al., "Risks of Intravitreous Injection: A Comprehensive Review," *Retina*, 24(5), pp. 676-698 (Oct. 2004) (Philadelphia, PA).
Johnson & Johnson Services, Inc., "Johnson & Johnson Completes Acquisition of Momenta Pharmaceuticals, Inc.," Press Release, (Oct. 1, 2020), https://www.jnj.com/johnson-johnson-completes-acquisition-of-momenta-pharmaceuticals-inc (accessed Aug. 2, 2021).
Johnson & Johnson Services, Inc., "Johnson & Johnson to Acquire Momenta Pharmaceuticals, Inc., Expanding Janssen's Leadership in Novel Treatments for Autoimmune Diseases," Press Release, (Aug. 19, 2020) https://www.jnj.com/johnson-johnson-to-acquire-momenta-pharmaceuticals-inc-expanding-janssens-leadership-in-novel-treatments-for-autoimmune-diseases (accessed Aug. 2, 2021).
Kaiser Family Foundation, "A Snapshot of Sources of Coverage Among Medicare Beneficiaries in 2018," available at: https://www.kff.org/medicare/issue-brief/a-snapshot-of-sources-of-coverage-among-medicare-beneficiaries-in-2018/ (accessed Mar. 23, 2021).
Kaiser Family Foundation, "Medicare Advantage in 2021: Enrollment Update and Key Trends," https://www.kff.org/medicare/issue-brief/medicare-advantage-in-2021-enrollment-update-and-key-trends/ (accessed Jun. 21, 2021).
Kanghong Pharmaceutical, "Announcement of Chengdu Kanghong Pharmaceutical Group Co., Ltd. on Stopping the Global Multi-center Clinical Trial of Conbercept Ophthalmic Injection," Press Release, http://epaper.zqrb.cn/html/2021-04/10/content_716426.htm?div=-1 (with English translation) (accessed Sep. 26, 2022).
Kim et al., "A Brief History of Anti-VEGF for the Treatment of Ocular Angiogenesis," *The American Journal of Pathology*, 181(2), pp. 376-379 (Aug. 2012).
Kim et al., "Eyes that Do Not Meet the Eligibility Criteria of Clinical Trials on Age-Related Macular Degeneration: Proportions of the Real-World Patient Population and Reasons for Exclusion," *Journal of Ophthalmology*, 2021: Article ID 6635467, 8 pages (Apr. 2021).
Kleiger et al., "The 1.7 Å Crystal Structure of BOI: A Study of How Two Dissimilar Amino Acid Sequences Can Adopt the Same Fold," *J. Mol. Biol.*, 299(4), pp. 1019-1034 (Jun. 2000).
Kuepper, "The Best Investment Information Sources: Using SEC Filings, Analyst Reports, and Company Websites," *The Balance*, https://www.thebalance.com/top-best-sources-of-investor-information-1979207 (accessed Jan. 20, 2021).
Kuhlmann et al., "Lessons Learned from Biosimilar Epoetins and Insulins," *The British Journal of Diabetes & Vascular Disease*, 10(2), pp. 90-99 (Apr. 2010).
L36962: Medicare Part AB Local Coverage Determination (LCD) Comment Summary (May 2, 2014), cited in Deposition of Dr. David M. Brown, M.D., on Apr. 26, 2022, submitted in IPR2021-00881 as Exhibit 1140.
Li et al., "Safety and Efficacy of Conbercept in Neovascular Age-Related Macular Degeneration: Results from a 12-Month Randomized Phase 2 Study: Aurora Study," *Ophthalmology*, 121(9), pp. 1740-1747 (2014).
Ling et al., "Deregulating Direct-to-Consumer Marketing of Prescription Drugs: Effects on Prescription and Over-the-Counter Product Sales," *Journal of Law and Economics*, 45, pp. 691-723 (2002).
Liu et al., "A Novel Engineered VEGF Blocker with an Excellent Pharmacokinetic Profile and Robust Anti-Tumor Activity," *BMC Cancer*, 15(170), pp. 1-14 (Mar. 2015) (online publication), cited in Deposition of Dr. Alexander M. Klibanov, Ph.D., on Mar. 24, 2022.
Lucentis Label (revised Apr. 2017), https://www.accessdata.fda.gov/drugsatfda_docs/label/2017/125156s1141b1.pdf (accessed Sep. 26, 2022).
Lucentis Label (revised Aug. 2012), https://www.accessdata.fda.gov/drugsatfda_docs/label/2012/125156s0069s00761b1.pdf (accessed Sep. 26, 2022).
Lucentis Label (revised Jun. 2010), https://www.accessdata.fda.gov/drugsatfda_docs/label/2010/125156s0531b1.pdf (accessed Sep. 26, 2022).
Lucentis Label (revised Mar. 2018), https://www.accessdata.fda.gov/drugsatfda_docs/label/2018/125156s1171b1.pdf (accessed Sep. 26, 2022).
Macugen Approval Letter (Dec. 17, 2004).
Macugen Label (revised Dec. 2004), https://www.accessdata.fda.gov/drugsatfda_docs/label/2004/0217561b1.pdf (accessed Sep. 26, 2022).
Macugen Label (submitted with NDA 21-756), submitted in IPR2021-00881 as Exhibit 2038.
Mankiw, *Principles of Microeconomics*, 5th ed., South-Western Cengage Learning (Mason, OH) (Sep. 2009).
Manning et al., "Similar Products at Different Prices: Can Biopharmaceutical Companies Segment Markets?" *International Journal of the Economics of Business*, 22(2), pp. 231-243 (Jun. 2015).
Mathis, "Fine-Tuning Your Anti-VEGF Injection Protocols: The Second Article in Our Series Recapping Research and Analysis Presented at Our Annual Meeting," *Retinal Physician* (Oct. 1, 2009), https://www.retinalphysician.corn/issues/2009/october-2009/fine-tuning-your-anti-vegf-injection-protocols (accessed Feb. 4, 2022).

(56) References Cited

OTHER PUBLICATIONS

Mayo Clinic, "Wet Macular Degeneration Symptoms and Causes," https://www.mayoclinic.org/diseases-conditions/wet-macular-degeneration/symptoms-causes/syc-20351107 (accessed Nov. 11, 2021).
Mayo Clinic, "Wet Macular Degeneration," https://www.mayoclinic.org/diseases-conditions/wet-macular-degeneration/diagnosis-treatment/drc-20351113 (accessed Nov. 11, 2021).
Medicare Interactive, "Medicare Part B Covered Services," https://www.medicareinteractive.org/get-answers/medicare-covered-services/medicare-coverage-overview/summary-of-part-b-covered-services (accessed Nov. 22, 2021).
Medicare Interactive, "The Parts of Medicare (A, B, C, D)," https://www.medicareinteractive.org/get-answers/medicare-basics/medicare-coverage-overview/original-medicare (accessed Nov. 30, 2021).
Medicare.gov, "Macular Degeneration Tests & Treatment," https://www.medicare.gov/coverage/macular-degeneration-tests-treatment (accessed Nov. 22, 2021).
Medicare.gov, "Medicare Advantage Plans," https://www.medicare.gov/sign-up-change-plans/types-of-medicare-health-plans/medicare-advantage-plans (accessed Dec. 31, 2021).
Medicare.gov, "When Does Medicare Coverage Start?" https://www.medicare.gov/basics/get-started-with-medicare/sign-up/when-does-medicare-coverage-start (accessed Dec. 15, 2021).
Medline Plus, "Laser Photocoagulation—Eye," https://medlineplus.gov/ency/article/007664.htm (accessed Dec. 2, 2021).
Miller & Zois, LLC, "Novartis Looking to Repurpose its Dangerous Beovu Drug," Nov. 28, 2020, https://www.drugrecalllawyerblog.com/novartis-repurpose-beovu.html (accessed Sep. 23, 2021).
Miller, "Taking Advantage of the New Purple Book Patent Requirements for Biologics," (Apr. 26, 2021), https://www.morganlewis.com/pubs/2021/04/taking-advantage-of-the-new-purple-book-patent-requirements-for-biologics (accessed Sep. 26, 2022).
Moroney et al., "Aflibercept in Epithelial Ovarian Carcinoma," *Future Oncology*, 5(5), pp. 591-600 (Jun. 2009).
Mueller et al., "Ocular Infection and Inflammation," Emergency Med. Clinics N. Am., 26(1), pp. 57-72 (Feb. 2008) (Philadelphia, PA).
Murphy et al., "Protein Folding, Misfolding, Stability and Aggregation: An Overview," in *Misbehaving Proteins—Protein (Mis)Folding, Aggregation, and Stability*; Murphy et al., eds., Springer, (2006) (New York, NY).
Nieto et al., "Ocular silicon distribution and clearance following intravitreal injection of porous silicon microparticles," *Exp. Eye Res.*, 116, pp. 161-168 (Nov. 2013).
Novartis Press Release, "Novartis Receives FDA Approval for Beovu, Offering Wet AMD Patients Vision Gains and Greater Fluid Reductions vs Aflibercept," (Oct. 8, 2019), https://www.novartis.com/news/media-releases/novartis-receives-fda-approval-beovu-offering-wet-amd-patients-vision-gains-and-greater-fluid-reductions-vs-aflibercept (accessed Sep. 26, 2022).
Novartis Press Release, "US FDA Approves Updated Novartis Beovu Label, to Include Additional Safety Information," (Jun. 11, 2020), https://www.novartis.com/news/media-releases/us-fda-approves-updated-novartis-beovu-label-include-additional-safety-information (accessed Sep. 26, 2022).
Novartis, Annual Report, 2020, submitted in IPR2021-00881 as Exhibit 2230.
Nucleic acid sequence alignment of SEQ ID No. 1 of the '338 and '069 patents with SEQ ID No. 15 of the '758 patent and SEQ ID No. 15 of the '959 patent, submitted in IPR2021-00881 as Exhibit 1124.
Nucleotide sequence alignment of SEQ ID No. 1 of the '338 patent with SEQ ID No. 15 of the '758 patent and SEQ ID No. 3 of Dix, submitted in IPR2022-00881 as Exhibit 1094.
Nucleotide sequence alignment of SEQ ID No. 1 of the '681 and '601 patents with SEQ ID No. 15 of the '758 patent and SEQ ID No. 1 of the '173 patent, submitted in IPR2022-01226 as Exhibit 1093.

Park et al., "New Approach to Anti-VEGF Agents for Age-Related Macular Degeneration," *Journal of Ophthalmology*, 2012:Article ID 637316 (Feb. 2012).
Pflugfelder et al., "Intravitreal Vancomycin: Retinal Toxicity, Clearance, and Interaction with Gentamicin," *Arch. Ophthalmol.*, 105(6), pp. 831-837 (Jun. 1987).
Pindyck et al., *Microeconomics*, Upper Saddle River: Prentice Hall (2013).
Piques et al., "Ribosome and transcript copy numbers, polysome occupancy and enzyme dynamics in *Arabidopsis,*" *Molecular Systems Biology*, 5(1), pp. 314 (Jan. 2009).
Prangé et al., "Exploring Hydrophobic Sites in Proteins with Xenon or Krypton," *Proteins: Structure, Function, and Genetics*, 30(1), pp. 61-73 (Jan. 1998).
Publication of OIG Special Fraud Alerts, 59 Fed. Reg. 242, (Dec. 19, 1994), https://oig.hhs.gov/documents/physicians-resources/980/121994.pdf (accessed Sep. 26, 2022).
Quiram et al., "Exudative Age-Related Macular Degeneration: Current Therapies and Potential Treatments," *Clinical Medicine: Therapeutics*, 1, pp. 1003-1011 (2009) (online publication).
Ramazi et al., "Post-translational modifications in proteins: resources, tools and prediction methods," *Database*, 2021(1):baab012 (Apr. 2021).
Regeneron Form 10-K for the year ended Dec. 31, 2005, submitted in IPR2021-00881 as Exhibit 1147.
Regeneron Form 10-K for the year ended Dec. 31, 2011, submitted in IPR2021-00881 as Exhibit 1149.
Regeneron Pharmaceuticals, Inc., "About," https://www.regeneron.com/about (accessed Nov. 3, 2021).
Regeneron Pharmaceuticals, Inc., "Eylea (aflibercept) Injection: Components of Reimbursement," 2015—[[Redacted]].
Regeneron Pharmaceuticals, Inc., "Eylea Injection Receives FDA Approval for Macular Edema Following Retinal Vein Occlusion (RVO)," Press Release, (Oct. 6, 2014) https://investor.regeneron.com/news-releases/news-release-details/eylear-aflibercept-injection-receives-fda-approval-macular-edema (accessed Sep. 26, 2022).
Regeneron Pharmaceuticals, Inc., "Eylea Injection Receives FDA Approval for the Treatment of Diabetic Macular Edema (DME)," Press Release, (Jul. 29, 2014) https://investor.regeneron.com/news-releases/news-release-details/eylear-aflibercept-injection-receives-fda-approval-treatment (accessed Sep. 26, 2022).
Regeneron Pharmaceuticals, Inc., "Eylea," https://eylea.us/ (accessed May 18, 2022).
Regeneron Pharmaceuticals, Inc., "FDA Approves Eylea Injection for Diabetic Retinopathy," (May 13, 2019) https://investor.regeneron.com/news-releases/news-release-details/fda-approves-eylear-aflibercept-injection-diabetic-retinopathy (accessed Sep. 26, 2022).
Regeneron Pharmaceuticals, Inc., "For the Treatment of Wet Age-Related Macular Degeneration," 2012.
Regeneron Pharmaceuticals, Inc., "History," https://www.regeneron.com/about/history (accessed Dec. 15, 2021).
Regeneron Pharmaceuticals, Inc., "Regeneron Announces FDA Approval of Eylea (Aflibercept) Injection for Macular Edema Following Central Retinal Vein Occlusion," Press Release, (Sep. 21, 2012) https://investor.regeneron.com/news-releases/news-release-details/regeneron-announces-fda-approval-eylear-aflibercept-injection (accessed Sep. 26, 2022).
Regeneron Pharmaceuticals, Inc., "Regeneron Reports Fourth Quarter and Full Year 2012 Financial and Operating Results," Press Release (Feb. 14, 2013), https://investor.regeneron.com/news-releases/news-release-details/regeneron-reports-fourth-quarter-and-full-year-2012-financial (accessed Aug. 2, 2021).
Regeneron Pharmaceuticals, Inc., "Regeneron Reports Fourth Quarter and Full Year 2019 Financial and Operating Results," Press Release, (Feb. 6, 2020), https://investor.regeneron.com/news-releases/news-release-details/regeneron-reports-fourth-quarter-and-full-year-2019-financial (accessed Aug. 2, 2021).
Regeneron Pharmaceuticals, Inc., "Regeneron's Yancopoulos Receives Columbia College's Alexander Hamilton Award," Press Release, (Nov. 22, 2019) https://www.prnewswire.com/news-releases/regenerons-yancopoulos-receives-columbia-colleges-alexander-hamilton-award-300963506.html (accessed Sep. 26, 2022), cited in Deposition of Dr. Diana V. Do, M.D., on Apr. 21, 2022.

(56) References Cited

OTHER PUBLICATIONS

Regeneron Pharmaceuticals, Inc., "Representative Regeneron U.S. Product Related Patents, Eylea (aflibercept) Injection," (Jan. 2022), https://www.regeneron.com/downloads/us-patent-products.pdf (accessed Sep. 26, 2022), cited in Deposition of Dr. Richard Manning, Ph.D., on May 4, 2022.
Regeneron Pharmaceuticals, Inc., "Research Areas," https://www.regeneron.com/science/research-areas (accessed Nov. 3, 2021).
Regeneron Pharmaceuticals, Inc., "U.S. Eylea Historical Brand P&L," May 2021, submitted in IPR2021-00881 as Exhibit 2200—[[Redacted]].
Regeneron Pharmaceuticals, Inc., "US Eylea P&L Ltd," Dec. 2021, submitted in IPR2021-00881 as Exhibit 2170—[[Redacted]].
Regeneron Pharmaceuticals, Inc., ATU Sales Share Data: All Indications, 2021, submitted in IPR2021-00881 as Exhibit 2279.
Regeneron Pharmaceuticals, Inc., ATU Sales Share Data: BRVO, 2021, submitted in IPR2021-00881 as Exhibit 2283.
Regeneron Pharmaceuticals, Inc., ATU Sales Share Data: CRVO, 2021, submitted in IPR2021-00881 as Exhibit 2282.
Regeneron Pharmaceuticals, Inc., ATU Sales Share Data: DME, 2021, submitted in IPR2021-00881 as Exhibit 2281.
Regeneron Pharmaceuticals, Inc., ATU Sales Share Data: DR w/o DME, 2021, submitted in IPR2021-00881 as Exhibit 2284.
Regeneron Pharmaceuticals, Inc., ATU Sales Share Data: Wet AMD, 2021, submitted in IPR2021-00881 as Exhibit 2280.
Regeneron Pharmaceuticals, Inc., Earnings Call Transcript, Apr. 26, 2012, submitted in IPR2021-00881 as Exhibit 2134.
Regeneron Pharmaceuticals, Inc., Earnings Call Transcript, Feb. 13, 2012, submitted in IPR2021-00881 as Exhibit 2133.
Regeneron Pharmaceuticals, Inc., Earnings Call Transcript, Jul. 25, 2012, submitted in IPR2021-00881 as Exhibit 2135.
Regeneron Pharmaceuticals, Inc., Eylea Gross & Net Sales P&L YTD, 2021, submitted in IPR2021-00881 as Exhibit 2285—[[Redacted]].
Regeneron Pharmaceuticals, Inc., Eylea Marketing Material, 2013, submitted in IPR2021-00881 as Exhibit 2136.
Regeneron Pharmaceuticals, Inc., Eylea Marketing Material, Nov. 2013, submitted in IPR2021-00881 as Exhibit 2137.
Regeneron Pharmaceuticals, Inc., Form 10-K, 2020, submitted in IPR2021-00881 as Exhibit 2254.
Retinal Physician, "Ongoing Treatment for Patients with Neovascular AMD," (Oct. 1, 2007), https://www.retinalphysician.com/issues/2007/october-2007/ongoing-treatment-for-patients-with-neovascular-am (accessed Sep. 26, 2022).
Retinal Physician, "Retinal Physician Symposium Covers Broad Range of Topics," (Sep. 1, 2006), https://www.retinalphysician.com/issues/2006/septemer-2006/retinal-physician-symposium-covers-broad-range-of (accessed Feb. 4, 2022).
Retinal Physician, "Revisiting an Early Treatment for Wet AMD: Is There a Role for Thermal Laser in the Era of Anti-VEGF Therapy?" Press Release, (Sep. 1, 2011) https://www.retinalphysician.com/issues/2011/september-2011/revisiting-an-early-treatment-for-wet-amd (accessed Sep. 26, 2022).
Roche, "FDA Approves Lucentis for Treatment of Diabetic Macular Edema," Press Release, (Aug. 13, 2012) https://www.roche.com/investors/updates/inv-update-2012-08-13.htm (accessed Sep. 26, 2022).
Roche, "FDA Approves Roche's Lucentis for Diabetic Retinopathy, the Leading Cause of Blindness Among Working Age Adults in the United States," Press Release, (Apr. 18, 2017) https://www.roche.com/media/releases/med-cor-2017-04-18b.htm (accessed Sep. 26, 2022).
Roche, Finance Report, 2020, submitted in IPR2021-00881 as Exhibit 2256.
Rowe et al., *Handbook of Pharmaceutical Excipients*, Cover to Preface (5th ed. 2006) (London, UK).
Schneider, "Nits, Grits, and Soft Information in SEC Filings," *U. PA. L. Rev.*, 121(2), pp. 254-305 (1972) (Philadelphia, PA).
Schweitzer, *Pharmaceutical Economics and Policy: Second Edition*, Oxford University Press (2007) (New York, NY).
ScienceDaily, "FDA Approves First Angiogenesis Inhibitor to Treat Colorectal Cancer," Press Release, (Feb. 27, 2004) https://www.sciencedaily.com/releases/2004/02/040227071334.htm (accessed Sep. 26, 2022).
Shen et al., "Clearance of Intravitreal Voriconazole," *Invest. Ophthalmology & Visual Sci.*, 45(5), pp. 2238-2241 (May 2007).
Sivaprasad, "Sustained-Release Steroid Options for DME Therapy," *Retina Today*, pp. 34-36 (Sep. 2021).
Solá et al., "Effects of Glycosylation on the Stability of Protein Pharmaceuticals," *Journal of Pharmaceutical Sciences*, 98(4), pp. 1223-1245 (Apr. 2009).
Stefanini et al., "Increase of Plasma VEGF after Intravenous Administration of Bevacizumab Is Predicted by a Pharmacokinetic Model," *Cancer Research*, 70(23), pp. 9886-9894 (Dec. 2010), cited in Deposition of Dr. Alexander M. Klibanov, Ph.D., on Mar. 24, 2022.
Thomas et al., "Comparative Effectiveness of Aflibercept for the Treatment of Patients with Neovascular Age-related Macular Degeneration," *Clinical Ophthalmology*, 7, pp. 495-501 (Mar. 2013).
Thomson Reuters, "Thomson Reuters Links Discovery and Literature Citation Databases," Press Release (Jan. 4, 2010).
Transcript of Deposition of Doris Weber dated May 13, 2022, in IPR2021-00881.
Transcript of Deposition of Dr. Alexander M. Klibanov, Ph.D., dated Mar. 24, 2022, in IPR2021-00880 and IPR2021-00881—[[Redacted]].
Transcript of Deposition of Dr. David M. Brown, M.D., dated Apr. 26, 2022, in IPR2021-00880 and IPR2021-00881.
Transcript of Deposition of Dr. Diana V. Do, M.D., dated Apr. 21, 2022, in IPR2021-00881.
Transcript of Deposition of Dr. Lucian V. Del Priore, M.D., dated Apr. 29, 2022, in IPR2021-00881—[[Redacted]].
Transcript of Deposition of Dr. Richard Manning, Ph.D., dated May 4, 2022, in IPR2021-00881—[[Redacted]].
Transcript of Deposition of Ivan Hofmann dated Jun. 23, 2022, in IPR2021-00880 and IPR2021-00881—[[Redacted]].
Transcript of Deposition of Mary Gerritsen, Ph.D., dated Jun. 17, 2022, in IPR2021-00880 and IPR2021-00881.
Transcript of Deposition of Thomas Albini, M.D., dated Jun. 22, 2022, in IPR2021-00880 and IPR2021-00881.
Transcript of the Teleconference before the United States Patent Trial and Appeal Board dated Feb. 23, 2022, in IPR2021-00881.
Transcript of the Teleconference before the United States Patent Trial and Appeal Board dated May 19, 2022, in IPR2021-00880 and IPR2021-00881.
Transcript of the Teleconference before the United States Patent Trial and Appeal Board dated Sep. 8, 2021, in IPR2021-00881.
U.S. Department of Health and Human Services (ASPE), "Medicare Part B Reimbursement of Prescription Drugs," Jun. 2014, available at: https://aspe.hhs.gov/sites/default/files/private/pdf/106966/ib_mprpd.pdf (accessed Sep. 26, 2022).
United Healthcare, "Ophthalmologic Policy: VEGF Inhibitors," effective Jan. 1, 2022, submitted in IPR2021-00881 as Exhibit 1167.
USC-Brookings, "Medicare Payment for Physician-Administered (Part B) Drugs: The Interim Final Rule and a Better Way Forward," https://www.brookings.edu/blog/usc-brookings-schaeffer-on-health-policy/2021/02/10/medicare-payment-for-physician-administered-part-b-drugs/ (accessed Sep. 26, 2022).
Vanderkam, "George Yancopoulos: Doing Well by Trying to Do Good," *Scientific American*, https://www.scientificamerican.com/article/george-yancopoulos-westinghouse/ (accessed Apr. 14, 2022), cited in Deposition of Dr. Diana V. Do, M.D., on Apr. 21, 2022.
Verywell Health, "Macular Degeneration: Timeline of Vision Loss Progression," https://www.verywellhealth.com/macular-degeneration-timeline-5069947 (accessed Mar. 21, 2021).
Vestrum Health, "Pharmaceutical Companies," https://www.vestrumhealth.com/pharma.php (accessed Jan. 3, 2022).
Vestum Health, "Homepage," https://www.vestrumhealth.com/index.php (accessed Jan. 3, 2022).
Visudyne Label (revised Apr. 2016), https://www.accessdata.fda.gov/drugsatfda_docs/label/2016/021119s0271b1.pdf (accessed Sep. 26, 2022).

(56) References Cited

OTHER PUBLICATIONS

Volkin et al., "Alterations in the Structure of Proteins that Cause Their Irreversible Inactivation," *Developments in Biological Standardization*, 74, pp. 73-81 (1992) (Basel, SI).
Weidner et al., "Observations Regarding the Average Sales Price Reimbursement Methodology," *Evidence-Based Oncology*, 27(4), pp. 156-160 (2021).
Wells et al., "Aflibercept, Bevacizumab, or Ranibizumab for Diabetic Macular Edema," *The New England Journal of Medicine*, 372(13), pp. 1193-1203 (2015).
Wilhelmus, "The Red Eye, Infectious Conjunctivitis, Keratitis, Endophthalmitis, and Periocular Cellulitis," *Infectious Disease Clinics N. Am.*, 2(1), pp. 99-116 (Mar. 1988) (Philadelphia, PA).
Wirbelauer, "Management of the Red Eye for the Primary Care Physician," *Am. J. Med.*, 119(4), pp. 302-306 (Apr. 2006) (online publication).
World Health Organization, "Blindness and Vision Impairment Fact Sheet," Press Release, (Oct. 14, 2021) https://www.who.int/news-room/fact-sheets/detail/blindness-and-visual-impairment (accessed Sep. 26, 2022).
World Health Organization, "International Nonproprietary Names for Pharmaceutical Substances (INN)," *WHO Drug Information*, 20, pp. 118-119 (2006), cited in Deposition of Dr. Alexander M. Klibanov, Ph.D., on Mar. 24, 2022.
Yahoo Finance, "Beovu Now Publicly Reimbursed in Ontario and New Brunswick for the Treatment of Neovascular Wet AMD," Press Release, (Dec. 17, 2021) https://finance.yahoo.com/news/beovu-brolucizumab-injection-now-publicly-120000109.html (accessed Dec. 30, 2021).
Yang, "Comparison of Binding Characteristics and in vitro Activities of Three Inhibitors of Vascular Endothelial Growth Factor A," *Molecular Pharmaceutics*, 11(10), pp. 3421-3429 (Oct. 2014), cited in Deposition of Dr. Alexander M. Klibanov, Ph.D., on Mar. 24, 2022.
Yorston, "Anti-VEGF Drugs in the Prevention of Blindness," *Community Eye Health Journal*, 27(87), pp. 44-46 (2014).
Zucchi, "Edgar: Investors' One-Stop-Shop for Company Filings," *Yahoo!Life*, https://www.yahoo.com/lifestyle/tagged/health/edgar-investors-one-stop-shop-170000800.html (accessed Jan. 20, 2021).
Clark, Slides entitled "Extended injection Interval ($\geq$q12wks) Maintains Vision in Neovascular Age-related Macular Degeneration: Year 2 VIEW Subanalysis," pp. 1-14 (Jan. 10, 2018), submitted in Office Action Response dated Feb. 23, 2023, in Canadian Patent Application No. 2,824,422.
Do et al., "Incorporating the Latest Findings From Clinical Trials Into the Management of Diabetic Retinopathy for the Comprehensive Ophthalmologist," https://aao.scientificposters.com/epsView.cfm?xvTgEJiNo9X9FY1srbBjRKZ9ICSVGWMJbEunzn9LGZqaMHKIw4tNfg%3D%3D (Oct. 25, 2009) (accessed Mar. 26, 2023), submitted in IPR2023-00739 as Exhibit 1023.
Expert Declaration of Dr. Edward Chaum in Support of Petition for Inter Partes Review of U.S. Pat. No. 10,888,601, dated Mar. 24, 2023, in IPR2023-00739.
Elman et al., "Randomized trial evaluating ranibizumab plus prompt or deferred laser or triamcinolone plus prompt laser for diabetic macular edema," Ophthalmology, 117(6): pp. 1064-1077.e35 (Jun. 2010).
Eylea Label (revised Feb. 2023), https://www.accessdata.fda.gov/drugsatfda_docs/label/2023/125387s0751b1.pdf (accessed Apr. 4, 2023).
IPR2023-00739, Paper 1, Petition for IPR (Mar. 26, 2023).
Decision Denying Institution of Inter Partes Review in *Apotex Inc. v. Regeneron Pharmaceuticals, Inc.*, IPR2022-01524.
Claim Construction Order entered in *Regeneron Pharmaceuticals, Inc. v. Mylan Pharmaceuticals Inc.*, Case No. 1:22-cv-00061-TSK, Northern District of West Virginia (Dkt. 427), Apr. 19, 2023.
Expert Declaration of Dr. Edward Chaum in Support of Petition for Inter Partes Review of U.S. Pat. No. 11,253,572, dated Apr. 27, 2023, IPR2023-00884.
IPR2023-00884, Paper 2, Petition for IPR (Apr. 27, 2023).

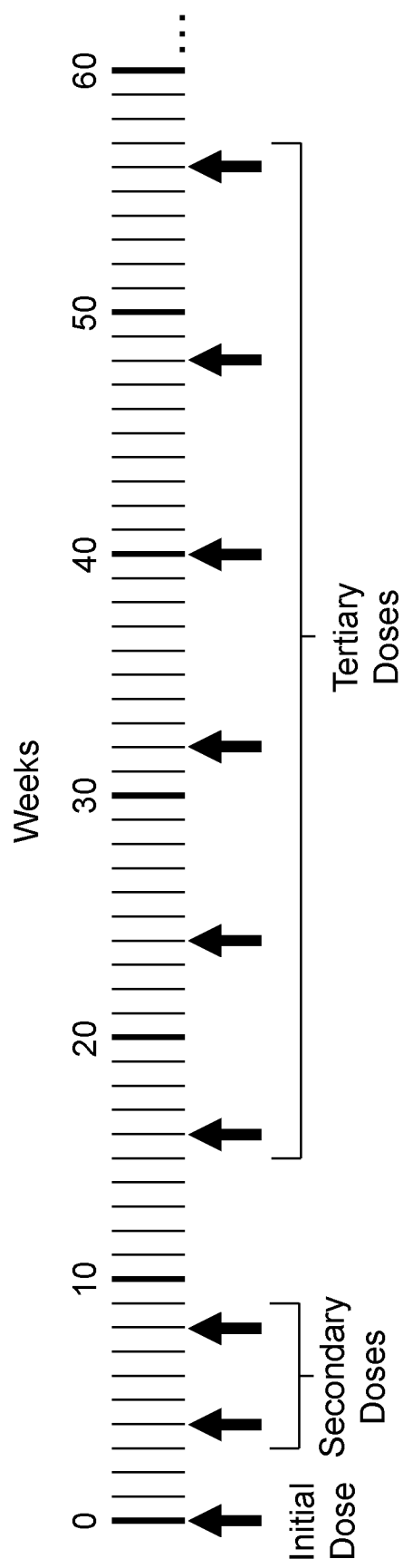

SEQUENCE LISTING

<160> NUMBER OF SEQ ID NOS: 2

<210> SEQ ID NO 1
<211> LENGTH: 1377
<212> TYPE: DNA
<213> ORGANISM: Artificial Sequence
<220> FEATURE:
<223> OTHER INFORMATION: Synthetic

<400> SEQUENCE: 1
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300

```
gggcttctga cctgtgaagc aacagtcaat gggcatttgt ataagacaaa ctatctcaca    360
catcgacaaa ccaatacaat catagatgtg gttctgagtc cgtctcatgg aattgaacta    420
tctgttggag aaaagcttgt cttaaattgt acagcaagaa ctgaactaaa tgtggggatt    480
gacttcaact gggaataccc ttcttcgaag catcagcata agaaacttgt aaaccgagac    540
ctaaaaaccc agtctgggag tgagatgaag aaattttttga gcaccttaac tatagatggt    600
gtaacccgga gtgaccaagg attgtacacc tgtgcagcat ccagtgggct gatgaccaag    660
aagaacagca catttgtcag ggtccatgaa aaggacaaaa ctcacacatg cccaccgtgc    720
ccagcacctg aactcctggg gggaccgtca gtcttcctct tccccccaaa acccaaggac    780
accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta caacagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aagggcagcc ccgagaacc acaggtgtac    1080 accctgcccc catcccggga tgagctgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga      1377
```

```
<210> SEQ ID NO 2
<211> LENGTH: 458
<212> TYPE: PRT
<213> ORGANISM: Artificial Sequence
<220> FEATURE:
<223> OTHER INFORMATION: Synthetic

<400> SEQUENCE: 2

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175
```

-continued

```
Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

USE OF A VEGF ANTAGONIST TO TREAT ANGIOGENIC EYE DISORDERS

CROSS-REFERENCE TO RELATED APPLICATIONS

This application is a continuation of Ser. No. 17/072,417 filed Oct. 16, 2020 which is a continuation of Ser. No. 16/397,267 filed Apr. 29, 2019, which is a continuation of Ser. No. 16/159,282 filed Oct. 12, 2018, now U.S. Pat. No. 10,828,345 issued Nov. 10, 2020, which is a continuation of Ser. No. 15/471,506 filed Mar. 28, 2017, now U.S. Pat. No. 10,130,681 issued Nov. 20, 2018, which is a continuation of Ser. No. 14/972,560 filed Dec. 17, 2015, now U.S. Pat. No. 9,669,069 issued Jun. 6, 2017, which is a continuation of Ser. No. 13/940,370 filed Jul. 12, 2013, now U.S. Pat. No. 9,254,338 issued Feb. 9, 2016, which is a continuation-in-part of International Patent Application No. PCT/US2012/020855, filed on Jan. 11, 2012, which claims the benefit of U.S. Provisional Application Nos. 61/432,245, filed on Jan. 13, 2011, 61/434,836, filed on Jan. 21, 2011, and 61/561,957, filed on Nov. 21, 2011, the contents of which are hereby incorporated by reference in their entireties.

FIELD OF THE INVENTION

The present invention relates to the field of therapeutic treatments of eye disorders. More specifically, the invention relates to the administration of VEGF antagonists to treat eye disorders caused by or associated with angiogenesis.

BACKGROUND

Several eye disorders are associated with pathological angiogenesis. For example, the development of age-related macular degeneration (AMD) is associated with a process called choroidal neovascularization (CNV). Leakage from the CNV causes macular edema and collection of fluid beneath the macula resulting in vision loss. Diabetic macular edema (DME) is another eye disorder with an angiogenic component. DME is the most prevalent cause of moderate vision loss in patients with diabetes and is a common complication of diabetic retinopathy, a disease affecting the blood vessels of the retina. Clinically significant DME occurs when fluid leaks into the center of the macula, the light-sensitive part of the retina responsible for sharp, direct vision. Fluid in the macula can cause severe vision loss or blindness. Yet another eye disorder associated with abnormal angiogenesis is central retinal vein occlusion (CRVO). CRVO is caused by obstruction of the central retinal vein that leads to a back-up of blood and fluid in the retina. The retina can also become ischemic, resulting in the growth of new, inappropriate blood vessels that can cause further vision loss and more serious complications. Release of vascular endothelial growth factor (VEGF) contributes to increased vascular permeability in the eye and inappropriate new vessel growth. Thus, inhibiting the angiogenic-promoting properties of VEGF appears to be an effective strategy for treating angiogenic eye disorders.

FDA-approved treatments of angiogenic eye disorders such as AMD and CRVO include the administration of an anti-VEGF antibody called ranibizumab (Lucentis®, Genentech, Inc.) on a monthly basis by intravitreal injection.

Methods for treating eye disorders using VEGF antagonists are mentioned in, e.g., U.S. Pat. Nos. 7,303,746; 7,306,799; 7,300,563; 7,303,748; and US 2007/0190058. Nonetheless, there remains a need in the art for new administration regimens for angiogenic eye disorders, especially those which allow for less frequent dosing while maintaining a high level of efficacy.

BRIEF SUMMARY OF THE INVENTION

The present invention provides methods for treating angiogenic eye disorders. The methods of the invention comprise sequentially administering multiple doses of a VEGF antagonist to a patient over time. In particular, the methods of the invention comprise sequentially administering to the patient a single initial dose of a VEGF antagonist, followed by one or more secondary doses of the VEGF antagonist, followed by one or more tertiary doses of the VEGF antagonists. The present inventors have surprisingly discovered that beneficial therapeutic effects can be achieved in patients suffering from angiogenic eye disorders by administering a VEGF antagonist to a patient at a frequency of once every 8 or more weeks, especially when such doses are preceded by about three doses administered to the patient at a frequency of about 2 to 4 weeks. Thus, according to the methods of the present invention, each secondary dose of VEGF antagonist is administered 2 to 4 weeks after the immediately preceding dose, and each tertiary dose is administered at least 8 weeks after the immediately preceding dose. An example of a dosing regimen of the present invention is shown in FIG. 1. One advantage of such a dosing regimen is that, for most of the course of treatment (i.e., the tertiary doses), it allows for less frequent dosing (e.g., once every 8 weeks) compared to prior administration regimens for angiogenic eye disorders which require monthly administrations throughout the entire course of treatment. (See, e.g., prescribing information for Lucentis® [ranibizumab], Genentech, Inc.).

The methods of the present invention can be used to treat any angiogenic eye disorder, including, e.g., age related macular degeneration, diabetic retinopathy, diabetic macular edema, central retinal vein occlusion, corneal neovascularization, etc.

The methods of the present invention comprise administering any VEGF antagonist to the patient. In one embodiment, the VEGF antagonist comprises one or more VEGF receptor-based chimeric molecule(s), (also referred to herein as a "VEGF-Trap" or "VEGFT"). An exemplary VEGF antagonist that can be used in the context of the present invention is a multimeric VEGF-binding protein comprising two or more VEGF receptor-based chimeric molecules referred to herein as "VEGFR1R2-FcΔC1(a)" or "aflibercept."

Various administration routes are contemplated for use in the methods of the present invention, including, e.g., topical administration or intraocular administration (e.g., intravitreal administration).

Aflibercept (EYLEA™, Regeneron Pharmaceuticals, Inc) was approved by the FDA in November 2011, for the treatment of patients with neovascular (wet) age-related macular degeneration, with a recommended dose of 2 mg administered by intravitreal injection every 4 weeks for the first three months, followed by 2 mg administered by intravitreal injection once every 8 weeks.

Other embodiments of the present invention will become apparent from a review of the ensuing detailed description.

BRIEF DESCRIPTION OF THE FIGURE

FIG. 1 shows an exemplary dosing regimen of the present invention. In this regimen, a single "initial dose" of VEGF antagonist ("VEGFT") is administered at the beginning of the treatment regimen (i.e. at "week 0"), two "secondary doses" are administered at weeks 4 and 8, respectively, and at least six "tertiary doses" are administered once every 8 weeks thereafter, i.e., at weeks 16, 24, 32, 40, 48, 56, etc.).

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described.

Dosing Regimens

The present invention provides methods for treating angiogenic eye disorders. The methods of the invention comprise sequentially administering to a patient multiple doses of a VEGF antagonist. As used herein, "sequentially administering" means that each dose of VEGF antagonist is administered to the patient at a different point in time, e.g., on different days separated by a predetermined interval (e.g., hours, days, weeks or months). The present invention includes methods which comprise sequentially administering to the patient a single initial dose of a VEGF antagonist, followed by one or more secondary doses of the VEGF antagonist, followed by one or more tertiary doses of the VEGF antagonist.

The terms "initial dose," "secondary doses," and "tertiary doses," refer to the temporal sequence of administration of the VEGF antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of VEGF antagonist, but will generally differ from one another in terms of frequency of administration. In certain embodiments, however, the amount of VEGF antagonist contained in the initial, secondary and/or tertiary doses will vary from one another (e.g., adjusted up or down as appropriate) during the course of treatment.

In one exemplary embodiment of the present invention, each secondary dose is administered 2 to 4 (e.g., 2, 2 ½, 3, 3 ½, or 4) weeks after the immediately preceding dose, and each tertiary dose is administered at least 8 (e.g., 8, 8 ½, 9, 9 ½, 10, 10 ½, 11, 11 ½, 12, 12 ½, 13, 13 ½, 14, 14 ½, or more) weeks after the immediately preceding dose. The phrase "the immediately preceding dose," as used herein, means, in a sequence of multiple administrations, the dose of VEGF antagonist which is administered to a patient prior to the administration of the very next dose in the sequence with no intervening doses.

In one exemplary embodiment of the present invention, a single initial dose of a VEGF antagonist is administered to a patient on the first day of the treatment regimen (i.e., at week 0), followed by two secondary doses, each administered four weeks after the immediately preceding dose (i.e., at week 4 and at week 8), followed by at least 5 tertiary doses, each administered eight weeks after the immediately preceding dose (i.e., at weeks 16, 24, 32, 40 and 48). The tertiary doses may continue (at intervals of 8 or more weeks) indefinitely during the course of the treatment regimen. This exemplary administration regimen is depicted graphically in FIG. 1.

The methods of the invention may comprise administering to a patient any number of secondary and/or tertiary doses of a VEGF antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 4 weeks after the immediately preceding dose. Similarly, in embodiments involving multiple tertiary doses, each tertiary dose may be administered at the same frequency as the other tertiary doses. For example, each tertiary dose may be administered to the patient 8 weeks after the immediately preceding dose. Alternatively, the frequency at which the secondary and/or tertiary doses are administered to a patient can vary over the course of the treatment regimen. For example, the present invention includes methods which comprise administering to the patient a single initial dose of a VEGF antagonist, followed by one or more secondary doses of the VEGF antagonist, followed by at least 5 tertiary doses of the VEGF antagonist, wherein the first four tertiary doses are administered 8 weeks after the immediately preceding dose, and wherein each subsequent tertiary dose is administered from 8 to 12 (e.g., 8, 8 ½, 9, 9 ½, 10, 10 ½, 11, 11 ½, 12) weeks after the immediately preceding dose. The frequency of administration may also be adjusted during the course of treatment by a physician depending on the needs of the individual patient following clinical examination.

VEGF Antagonists

The methods of the present invention comprise administering to a patient a VEGF antagonist according to specified dosing regimens. As used herein, the expression "VEGF antagonist" means any molecule that blocks, reduces or interferes with the normal biological activity of VEGF.

VEGF antagonists include molecules which interfere with the interaction between VEGF and a natural VEGF receptor, e.g., molecules which bind to VEGF or a VEGF receptor and prevent or otherwise hinder the interaction between VEGF and a VEGF receptor. Specific exemplary VEGF antagonists include anti-VEGF antibodies, anti-VEGF receptor antibodies, and VEGF receptor-based chimeric molecules (also referred to herein as "VEGF-Traps").

VEGF receptor-based chimeric molecules include chimeric polypeptides which comprise two or more immunoglobulin (Ig)-like domains of a VEGF receptor such as VEGFR1 (also referred to as Flt1) and/or VEGFR2 (also referred to as Flk1 or KDR), and may also contain a multimerizing domain (e.g., an Fc domain which facilitates the multimerization [e.g., dimerization] of two or more chimeric polypeptides). An exemplary VEGF receptor-based chimeric molecule is a molecule referred to as VEGFR1R2-FcΔC1(a) which is encoded by the nucleic acid sequence of SEQ ID NO:1. VEGFR1R2-FcΔC1(a) comprises three components: (1) a VEGFR1 component comprising amino acids 27 to 129 of SEQ ID NO:2; (2) a VEGFR2 component comprising amino acids 130 to 231 of SEQ ID NO:2; and (3) a multimerization component ("FcΔC1(a)") comprising amino acids 232 to 457 of SEQ ID NO:2 (the C-terminal amino acid of SEQ ID NO:2 [i.e., K458] may or may not be included in the VEGF antagonist used in the methods of the invention; see e.g., U.S. Pat. No. 7,396,664). Amino acids 1-26 of SEQ ID NO:2 are the signal sequence.

The VEGF antagonist used in the Examples set forth herein below is a dimeric molecule comprising two VEGFR1R2-FcΔC1(a) molecules and is referred to herein as "VEGFT." Additional VEGF receptor-based chimeric molecules which can be used in the context of the present invention are disclosed in U.S. Pat. Nos. 7,396,664, 7,303, 746 and WO 00/75319.

Angiogenic Eye Disorders

The methods of the present invention can be used to treat any angiogenic eye disorder. The expression "angiogenic eye disorder," as used herein, means any disease of the eye which is caused by or associated with the growth or proliferation of blood vessels or by blood vessel leakage. Non-limiting examples of angiogenic eye disorders that are treatable using the methods of the present invention include age-related macular degeneration (e.g., wet AMD, exudative AMD, etc.), retinal vein occlusion (RVO), central retinal vein occlusion (CRVO; e.g., macular edema following CRVO), branch retinal vein occlusion (BRVO), diabetic macular edema (DME), choroidal neovascularization (CNV; e.g., myopic CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, and diabetic retinopathies.

Pharmaceutical Formulations

The present invention includes methods in which the VEGF antagonist that is administered to the patient is contained within a pharmaceutical formulation. The pharmaceutical formulation may comprise the VEGF antagonist along with at least one inactive ingredient such as, e.g., a pharmaceutically acceptable carrier. Other agents may be incorporated into the pharmaceutical composition to provide improved transfer, delivery, tolerance, and the like. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the antibody is administered. A multitude of appropriate formulations can be found in the formulary known to all pharmaceutical chemists: Remington's Pharmaceutical Sciences (15th ed, Mack Publishing Company, Easton, Pa., 1975), particularly Chapter 87 by Blaug, Seymour, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in the context of the methods of the present invention, provided that the VEGF antagonist is not inactivated by the formulation and the formulation is physiologically compatible and tolerable with the route of administration. See also Powell et al. PDA (1998) J Pharm Sci Technol. 52:238-311 and the citations therein for additional information related to excipients and carriers well known to pharmaceutical chemists.

Pharmaceutical formulations useful for administration by injection in the context of the present invention may be prepared by dissolving, suspending or emulsifying a VEGF antagonist in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there may be employed, e.g., sesame oil, soybean oil, etc., which may be used in combination with a solubilizing agent such as benzyl benzoate, benzyl alcohol, etc. The injection thus prepared can be filled in an appropriate ampoule if desired.

Modes of Administration

The VEGF antagonist (or pharmaceutical formulation comprising the VEGF antagonist) may be administered to the patient by any known delivery system and/or administration method. In certain embodiments, the VEGF antagonist is administered to the patient by ocular, intraocular, intravitreal or subconjunctival injection. In other embodiments, the VEGF antagonist can be administered to the patient by topical administration, e.g., via eye drops or other liquid, gel, ointment or fluid which contains the VEGF antagonist and can be applied directly to the eye. Other possible routes of administration include, e.g., intradermal, intramuscular, intraperitoneal, intravenous, subcutaneous, intranasal, epidural, and oral.

Amount of VEGF Antagonist Administered

Each dose of VEGF antagonist administered to the patient over the course of the treatment regimen may contain the same, or substantially the same, amount of VEGF antagonist. Alternatively, the quantity of VEGF antagonist contained within the individual doses may vary over the course of the treatment regimen. For example, in certain embodiments, a first quantity of VEGF antagonist is administered in the initial dose, a second quantity of VEGF antagonist is administered in the secondary doses, and a third quantity of VEGF antagonist is administered in the tertiary doses. The present invention contemplates dosing schemes in which the quantity of VEGF antagonist contained within the individual doses increases over time (e.g., each subsequent dose contains more VEGF antagonist than the last), decreases over time (e.g., each subsequent dose contains less VEGF antagonist than the last), initially increases then decreases, initially decreases then increases, or remains the same throughout the course of the administration regimen.

The amount of VEGF antagonist administered to the patient in each dose is, in most cases, a therapeutically effective amount. As used herein, the phrase "therapeutically effective amount" means a dose of VEGF antagonist that results in a detectable improvement in one or more symptoms or indicia of an angiogenic eye disorder, or a dose of VEGF antagonist that inhibits, prevents, lessens, or delays the progression of an angiogenic eye disorder. In the case of an anti-VEGF antibody or a VEGF receptor-based chimeric molecule such as VEGFR1R2-FcΔC1(a), a therapeutically effective amount can be from about 0.05 mg to about 5 mg, e.g., about 0.05 mg, about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 1.0 mg, about 1.05 mg, about 1.1 mg, about 1.15 mg, about 1.2 mg, about 1.25 mg, about 1.3 mg, about 1.35 mg, about 1.4 mg, about 1.45 mg, about 1.5 mg, about 1.55 mg, about 1.6 mg, about 1.65 mg, about 1.7 mg, about 1.75 mg, about 1.8 mg, about 1.85 mg, about 1.9 mg, about 2.0 mg, about 2.05 mg, about 2.1 mg, about 2.15 mg, about 2.2 mg, about 2.25 mg, about 2.3 mg, about 2.35 mg, about 2.4 mg, about 2.45 mg, about 2.5 mg, about 2.55 mg, about 2.6 mg, about 2.65 mg, about 2.7 mg, about 2.75 mg, about 2.8 mg, about 2.85 mg, about 2.9 mg, about 3.0 mg, about 3.5 mg, about 4.0 mg, about 4.5 mg, or about 5.0 mg of the antibody or receptor-based chimeric molecule.

The amount of VEGF antagonist contained within the individual doses may be expressed in terms of milligrams of antibody per kilogram of patient body weight (i.e., mg/kg). For example, the VEGF antagonist may be administered to a patient at a dose of about 0.0001 to about 10 mg/kg of patient body weight.

Treatment Population and Efficacy

The methods of the present invention are useful for treating angiogenic eye disorders in patients that have been diagnosed with or are at risk of being afflicted with an angiogenic eye disorder. Generally, the methods of the present invention demonstrate efficacy within 104 weeks of the initiation of the treatment regimen (with the initial dose administered at "week 0"), e.g., by the end of week 16, by the end of week 24, by the end of week 32, by the end of week 40, by the end of week 48, by the end of week 56, etc. In the context of methods for treating angiogenic eye disorders such as AMD, CRVO, and DME, "efficacy" means that, from the initiation of treatment, the patient exhibits a loss of 15 or fewer letters on the Early Treatment Diabetic Retinopathy Study (ETDRS) visual acuity chart. In certain embodiments, "efficacy" means a gain of one or more (e.g., 1, 2, 3, 4, 5, 6, 7, 8, 9, 10, 11 or more) letters on the ETDRS chart from the time of initiation of treatment.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The exemplary VEGF antagonist used in all Examples set forth below is a dimeric molecule having two functional VEGF binding units. Each functional binding unit is comprised of Ig domain 2 from VEGFR1 fused to Ig domain 3 from VEGFR2, which in turn is fused to the hinge region of a human IgG1 Fc domain (VEGFR1R2-FcΔC1(a); encoded by SEQ ID NO:1). This VEGF antagonist is referred to in the examples below as "VEGFT". For purposes of the following Examples, "monthly" dosing is equivalent to dosing once every four weeks.

Example 1: Phase I Clinical Trial of Intravitreally Administered VEGF Receptor-Based Chimeric Molecule (VEGFT) in Subjects with Neovascular AMD In this Phase I study, 21 subjects with neovascular AMD received a single intravitreal (IVT) dose of VEGFT. Five groups of three subjects each received either 0.05, 0.15, 0.5, 2 or 4 mg of VEGFT, and a sixth group of six subjects received 1 mg. No serious adverse events related to the study drug, and no identifiable intraocular inflammation was reported. Preliminary results showed that, following injection of VEGFT, a rapid decrease in foveal thickness and macular volume was observed that was maintained through 6 weeks. At Day 43 across all dose groups, mean excess retinal thickness [excess retinal thickness=(retinal thickness−179 μ)] on optical coherence tomography (OCT) was reduced from 119 μ to 27 μ as assessed by Fast Macular Scan and from 194 μ to 60 μ as assessed using a single Posterior Pole scan. The mean increase in best corrected visual acuity (BCVA) was 4.75 letters, and BCVA was stable or improved in 95% of subjects. In the 2 highest dose groups (2 and 4 mg), the mean increase in BCVA was 13.5 letters, with 3 of 6 subjects demonstrating improvement of ≥3 lines.

Example 2: Phase II Clinical Trial of Repeated Doses of Intravitreally Administered VEGF Receptor-Based Chimeric Molecule (VEGFT) in Subjects with Neovascular AMD This study was a double-masked, randomized study of 3 doses (0.5, 2, and 4 mg) of VEGFT tested at 4-week and/or 12-week dosing intervals. There were 5 treatment arms in this study, as follows: 1) 0.5 mg every 4 weeks, 2) 0.5 mg every 12 weeks, 3) 2 mg every 4 weeks, 4) 2 mg every 12 weeks and 5) 4 mg every 12 weeks. Subjects were dosed at a fixed interval for the first 12 weeks, after which they were evaluated every 4 weeks for 9 months, during which additional doses were administered based on pre-specified criteria. All subjects were then followed for one year after their last dose of VEGFT. Preliminary data from a pre-planned interim analysis indicated that VEGFT met its primary endpoint of a statistically significant reduction in retinal thickness after 12 weeks compared with baseline (all groups combined, decrease of 135 μ, p<0.0001). Mean change from baseline in visual acuity, a key secondary endpoint of the study, also demonstrated statistically significant improvement (all groups combined, increase of 5.9 letters, p<0.0001). Moreover, patients in the dose groups that received only a single dose, on average, demonstrated a decrease in excess retinal thickness (p<0.0001) and an increase in visual acuity (p=0.012) at 12 weeks. There were no drug-related serious adverse events, and treatment with the VEGF antagonists was generally well-tolerated. The most common adverse events were those typically associated with intravitreal injections.

Example 3: Phase I Clinical Trial of Systemically Administered VEGF Receptor-Based Chimeric Molecule (VEGFT) in Subjects with Neovascular AMD This study was a placebo-controlled, sequential-group, dose-escalating safety, tolerability and bioeffect study of VEGFT by IV infusion in subjects with neovascular AMD. Groups of 8 subjects meeting eligibility criteria for subfoveal choroidal neovascularization (CNV) related to AMD were assigned to receive 4 IV injections of VEGFT or placebo at dose levels of 0.3, 1, or 3 mg/kg over an 8-week period.

Most adverse events that were attributed to VEGFT were mild to moderate in severity, but 2 of 5 subjects treated with 3 mg/kg experienced dose-limiting toxicity (DLT) (one with Grade 4 hypertension and one with Grade 2 proteinuria); therefore, all subjects in the 3 mg/kg dose group did not enter the study. The mean percent changes in excess retinal thickness were: −12%, −10%, −66%, and −60% for the placebo, 0.3, 1, and 3 mg/kg dose groups at day 15 (ANOVA p<0.02), and −5.6%, +47.1%, and −63.3% for the placebo, 0.3, and 1 mg/kg dose groups at day 71 (ANOVA p<0.02). There was a numerical improvement in BCVA in the subjects treated with VEGFT. As would be expected in such a small study, the results were not statistically significant.

Example 4: Phase III Clinical Trials of the Efficacy, Safety, and Tolerability of Repeated Doses of Intravitreal VEGFT in Subjects with Neovascular Age-Related Macular Degeneration

A. Objectives, Hypotheses and Endpoints

Two parallel Phase III clinical trials were carried out to investigate the use of VEGFT to treat patients with the neovascular form of age-related macular degeneration (Study 1 and Study 2). The primary objective of these studies was to assess the efficacy of IVT administered VEGFT compared to ranibizumab (Lucentis®, Genentech, Inc.), in a non-inferiority paradigm, in preventing moderate vision loss in subjects with all subtypes of neovascular AMD.

The secondary objectives were (a) to assess the safety and tolerability of repeated IVT administration of VEGFT in subjects with all sub-types of neovascular AMD for periods up to 2 years; and (b) to assess the effect of repeated IVT administration of VEGFT on Vision-Related Quality of Life (QOL) in subjects with all sub-types of neovascular AMD.

The primary hypothesis of these studies was that the proportion of subjects treated with VEGFT with stable or improved BCVA (<15 letters lost) is similar to the proportion treated with ranibizumab who have stable or improved BCVA, thereby demonstrating non-inferiority.

The primary endpoint for these studies was the prevention of vision loss of greater than or equal to 15 letters on the ETDRS chart, compared to baseline, at 52 weeks. Secondary endpoints were as follows: (a) change from baseline to Week 52 in letter score on the ETDRS chart; (b) gain from baseline to Week 52 of 15 letters or more on the ETDRS chart; (c) change from baseline to Week 52 in total NEI VFQ-25 score; and (d) change from baseline to Week 52 in CNV area.

B. Study Design

For each study, subjects were randomly assigned in a 1:1:1:1 ratio to 1 of 4 dosing regimens: (1) 2 mg VEGFT administered every 4 weeks (2Q4); (2) 0.5 mg VEGFT administered every 4 weeks (0.5Q4); (3) 2 mg VEGFT administered every 4 weeks to week 8 and then every 8 weeks (with sham injection at the interim 4-week visits when study drug was not administered (2Q8); and (4) 0.5 mg ranibizumab administered every 4 weeks (RQ4). Subjects assigned to (2Q8) received the 2 mg injection every 4 weeks to week 8 and then a sham injection at interim 4-week visits (when study drug is not to be administered) during the first 52 weeks of the studies. (No sham injection were given at Week 52).

The study duration for each subject was scheduled to be 96 weeks plus the recruitment period. For the first 52 weeks (Year 1), subjects received an IVT or sham injection in the study eye every 4 weeks. (No sham injections were given at Week 52). During the second year of the study, subjects will be evaluated every 4 weeks and will receive IVT injection of study drug at intervals determined by specific dosing criteria, but at least every 12 weeks. (During the second year of the study, sham injections will not be given.) During this period, injections may be given as frequently as every 4 weeks, but no less frequently than every 12 weeks, according to the following criteria: (i) increase in central retinal thickness of ≥100 μm compared to the lowest previous value as measured by optical coherence tomography (OCT); or (ii) a loss from the best previous letter score of at least 5 ETDRS letters in conjunction with recurrent fluid as indicated by OCT; or (iii) new or persistent fluid as indicated by OCT; or (iv) new onset classic neovascularization, or new or persistent leak on fluorescein angiography (FA); or (v) new macular hemorrhage; or (vi) 12 weeks have elapsed since the previous injection. According to the present protocol, subjects must receive an injection at least every 12 weeks.

Subjects were evaluated at 4 weeks intervals for safety and best corrected visual acuity (BCVA) using the 4 meter ETDRS protocol. Quality of Life (QOL) was evaluated using the NEI VFQ-25 questionnaire. OCT and FA examinations were conducted periodically.

Approximately 1200 subjects were enrolled, with a target enrollment of 300 subjects per treatment arm.

To be eligible for this study, subjects were required to have subfoveal choroidal neovascularization (CNV) secondary to AMD. "Subfoveal" CNV was defined as the presence of subfoveal neovascularization, documented by FA, or presence of a lesion that is juxtafoveal in location angiographically but affects the fovea. Subject eligibility was confirmed based on angiographic criteria prior to randomization.

Only one eye was designated as the study eye. For subjects who met eligibility criteria in both eyes, the eye with the worse VA was selected as the study eye. If both eyes had equal VA, the eye with the clearest lens and ocular media and least amount of subfoveal scar or geographic atrophy was selected. If there was no objective basis for selecting the study eye, factors such as ocular dominance, other ocular pathology and subject preference were considered in making the selection.

Inclusion criteria for both studies were as follows: (i) signed Informed consent; (ii) at least 50 years of age; (iii)

active primary subfoveal CNV lesions secondary to AMD, including juxtafoveal lesions that affect the fovea as evidenced by FA in the study eye; (iv) CNV at least 50% of total lesion size; (v) early treatment diabetic retinopathy study (ETDRS) best-corrected visual acuity of: 20/40 to 20/320 (letter score of 73 to 25) in the study eye; (vi) willing, committed, and able to return for all clinic visits and complete all study-related procedures; and (vii) able to read, understand and willing to sign the informed consent form (or, if unable to read due to visual impairment, be read to verbatim by the person administering the informed consent or a family member).

Exclusion criteria for both studies were as follows: 1. Any prior ocular (in the study eye) or systemic treatment or surgery for neovascular AMD except dietary supplements or vitamins. 2. Any prior or concomitant therapy with another investigational agent to treat neovascular AMD in the study eye, except dietary supplements or vitamins. 3. Prior treatment with anti-VEGF agents as follows: (a) Prior treatment with anti-VEGF therapy in the study eye was not allowed; (b) Prior treatment with anti-VEGF therapy in the fellow eye with an investigational agent (not FDA approved, e.g. bevacizumab) was allowed up to 3 months prior to first dose in the study, and such treatments were not allowed during the study. Prior treatment with an approved anti-VEGF therapy in the fellow eye was allowed; (c) Prior systemic anti-VEGF therapy, investigational or FDA/Health Canada approved, was only allowed up to 3 months prior to first dose, and was not allowed during the study. 4. Total lesion size >12 disc areas (30.5 mm2, including blood, scars and neovascularization) as assessed by FA in the study eye. 5. Subretinal hemorrhage that is either 50% or more of the total lesion area, or if the blood is under the fovea and is 1 or more disc areas in size in the study eye. (If the blood is under the fovea, then the fovea must be surrounded 270 degrees by visible CNV.) 6. Scar or fibrosis, making up >50% of total lesion in the study eye. 7. Scar, fibrosis, or atrophy involving the center of the fovea. 8. Presence of retinal pigment epithelial tears or rips involving the macula in the study eye. 9. History of any vitreous hemorrhage within 4 weeks prior to Visit 1 in the study eye. 10. Presence of other causes of CNV, including pathologic myopia (spherical equivalent of −8 diopters or more negative, or axial length of 25 mm or more), ocular histoplasmosis syndrome, angioid streaks, choroidal rupture, or multifocal choroiditis in the study eye. 11. History or clinical evidence of diabetic retinopathy, diabetic macular edema or any other vascular disease affecting the retina, other than AMD, in either eye. 12. Prior vitrectomy in the study eye. 13. History of retinal detachment or treatment or surgery for retinal detachment in the study eye. 14. Any history of macular hole of stage 2 and above in the study eye. 15. Any intraocular or periocular surgery within 3 months of Day 1 on the study eye, except lid surgery, which may not have taken place within 1 month of day 1, as long as it was unlikely to interfere with the injection. 16. Prior trabeculectomy or other filtration surgery in the study eye. 17. Uncontrolled glaucoma (defined as intraocular pressure greater than or equal to 25 mm Hg despite treatment with anti-glaucoma medication) in the study eye. 18. Active intraocular inflammation in either eye. 19. Active ocular or periocular infection in either eye. 20. Any ocular or periocular infection within the last 2 weeks prior to Screening in either eye. 21. Any history of uveitis in either eye. 22. Active scleritis or episcleritis in either eye. 23. Presence or history of scleromalacia in either eye. 24. Aphakia or pseudophakia with absence of posterior capsule (unless it occurred as a result of a yttrium aluminum garnet [YAG] posterior capsulotomy) in the study eye. 25. Previous therapeutic radiation in the region of the study eye. 26. History of corneal transplant or corneal dystrophy in the study eye. 27. Significant media opacities, including cataract, in the study eye which might interfere with visual acuity, assessment of safety, or fundus photography. 28. Any concurrent intraocular condition in the study eye (e.g. cataract) that, in the opinion of the investigator, could require either medical or surgical intervention during the 96 week study period. 29. Any concurrent ocular condition in the study eye which, in the opinion of the investigator, could either increase the risk to the subject beyond what is to be expected from standard procedures of intraocular injection, or which otherwise may interfere with the injection procedure or with evaluation of efficacy or safety. 30. History of other disease, metabolic dysfunction, physical examination finding, or clinical laboratory finding giving reasonable suspicion of a disease or condition that contraindicates the use of an investigational drug or that might affect interpretation of the results of the study or render the subject at high risk for treatment complications. 31. Participation as a subject in any clinical study within the 12 weeks prior to Day 1. 32. Any systemic or ocular treatment with an investigational agent in the past 3 months prior to Day 1. 33. The use of long acting steroids, either systemically or intraocularly, in the 6 months prior to day 1. 34. Any history of allergy to povidone iodine. 35. Known serious allergy to the fluorescein sodium for injection in angiography. 36. Presence of any contraindications indicated in the FDA Approved label for ranibizumab (Lucentis®). 37. Females who were pregnant, breastfeeding, or of childbearing potential, unwilling to practice adequate contraception throughout the study. Adequate contraceptive measures include oral contraceptives (stable use for 2 or more cycles prior to screening); IUD; Depo-Provera®; Norplant® System implants; bilateral tubal ligation; vasectomy; condom or diaphragm plus either contraceptive sponge, foam or jelly.

Subjects were not allowed to receive any standard or investigational agents for treatment of their AMD in the study eye other than their assigned study treatment with VEGFT or ranibizumab as specified in the protocol until they completed the Completion/Early Termination visit assessments. This includes medications administered locally (e.g., IVT, topical, juxtascleral or periorbital routes), as well as those administered systemically with the intent of treating the study and/or fellow eye.

The study procedures are summarized as follows:

Best Corrected Visual Acuity: Visual function of the study eye and the fellow eye were assessed using the ETDRS protocol (The Early Treatment Diabetic Retinopathy Study Group) at 4 meters. Visual Acuity examiners were certified to ensure consistent measurement of BCVA. The VA examiners were required to remain masked to treatment assignment.

Optical Coherence Tomography: Retinal and lesion characteristics were evaluated using OCT on the study eye. At the Screen Visit (Visit 1) images were captured and transmitted for both eyes. All OCT images were captured using the Zeiss Stratus OCT™ with software Version 3 or greater. OCT images were sent to an independent reading center where images were read by masked readers at visits where OCTs were required. All OCTs were electronically archived at the site as part of the source documentation. A subset of OCT images were read. OCT technicians were required to be certified by the reading center to ensure consistency and quality in image acquisition. Adequate efforts were made to ensure that OCT technicians at the site remained masked to treatment assignment.

Fundus Photography and Fluorescein Angiography (FA): The anatomical state of the retinal vasculature of the study eye was evaluated by funduscopic examination, fundus photography and FA. At the Screen Visit (Visit 1) funduscopic examination, fundus photography and FA were captured and transmitted for both eyes. Fundus and angiographic images were sent to an independent reading center where images were read by masked readers. The reading center confirmed subject eligibility based on angiographic criteria prior to randomization. All FAs and fundus photographs were archived at the site as part of the source documentation. Photographers were required to be certified by the reading center to ensure consistency and quality in image acquisition. Adequate efforts were made to ensure that all photographers at the site remain masked to treatment assignment.

Vision-Related Quality of Life: Vision-related QOL was assessed using the National Eye Institute 25-Item Visual Function Questionnaire (NEI VFQ-25) in the interviewer-administered format. NEI VFQ-25 was administered by certified personnel at a contracted call center. At the screening visit, the sites assisted the subject and initiated the first call to the call center to collect all of the subject's contact information and to complete the first NEI VFQ-25 on the phone prior to randomization and IVT injection. For all subsequent visits, the call center called the subject on the phone, prior to IVT injection, to complete the questionnaire.

Intraocular Pressure: Intraocular pressure (IOP) of the study eye was measured using applanation tonometry or Tonopen. The same method of IOP measurement was used in each subject throughout the study.

C. Results Summary (52 Week Data)

The primary endpoint (prevention of moderate or severe vision loss as defined above) was met for all three VEGFT groups (2Q4, 0.5Q4 and 2Q8) in this study. The results from both studies are summarized in Table 1.

TABLE 1

|  | Ranibizumab 0.5 mg monthly (RQ4) | VEGFT 0.5 mg monthly (0.5Q4) | VEGFT 2 mg monthly (2Q4) | VEGFT 2 mg every 8 weeks[a] (2Q8) |
|---|---|---|---|---|
| Maintenance of vision* (% patients losing <15 letters) at week 52 versus baseline | | | | |
| Study 1 | 94.4% | 95.9%** | 95.1%** | 95.1%** |
| Study 2 | 94.4% | 96.3%** | 95.6%** | 95.6%** |
| Mean improvement in vision* (letters) at 52 weeks versus baseline (p-value vs RQ4)*** | | | | |
| Study 1 | 8.1 | 6.9 (NS) | 10.9 (p < 0.01) | 7.9 (NS) |
| Study 2 | 9.4 | 9.7 (NS) | 7.6 (NS) | 8.9 (NS |

[a]Following three initial monthly doses
*Visual acuity was measured as the total number of letters read correctly on the Early Treatment Diabetic Retinopathy Study (ETDRS) eye chart.
**Statistically non-inferior based on a non-inferiority margin of 10%, using confidence interval approach (95.1% and 95% for Study 1 and Study 2, respectively)
***Test for superiority
NS = non-significant In Study 1, patients receiving VEGFT 2 mg monthly (2Q4) achieved a statistically significant greater mean improvement in visual acuity at week 52 versus baseline (secondary endpoint), compared to ranibizumab 0.5 mg monthly (RQ4); patients receiving VEGFT 2 mg monthly on average gained 10.9 letters, compared to a mean 8.1 letter gain with ranibizumab 0.5 mg dosed every month (p<0.01). All other dose groups of VEGFT in Study 1 and all dose groups in Study 2 were not statistically different from ranibizumab in this secondary endpoint.

A generally favorable safety profile was observed for both VEGFT and ranibizumab. The incidence of ocular treatment emergent adverse events was balanced across all four treatment groups in both studies, with the most frequent events associated with the injection procedure, the underlying disease, and/or the aging process. The most frequent ocular adverse events were conjunctival hemorrhage, macular degeneration, eye pain, retinal hemorrhage, and vitreous floaters. The most frequent serious non-ocular adverse events were typical of those reported in this elderly population who receive intravitreal treatment for wet AMD; the most frequently reported events were falls, pneumonia, myocardial infarction, atrial fibrillation, breast cancer, and acute coronary syndrome. There were no notable differences among the study arms.

Example 5: Phase II Clinical Trial of VEGFT in Subjects with Diabetic Macular Edema (DME)

In this study, 221 patients with clinically significant DME with central macular involvement were randomized, and 219 patients were treated with balanced distribution over five groups. The control group received macular laser therapy at baseline, and patients were eligible for repeat laser treatments, but no more frequently than at 16 week intervals. The remaining four groups received VEGFT by intravitreal injection as follows: Two groups received 0.5 or 2 mg of VEGFT once every four weeks throughout the 12-month dosing period (0.5Q4 and 2Q4, respectively). Two groups received three initial doses of 2 mg VEGFT once every four weeks (i.e., at baseline, and weeks 4 and 8), followed through week 52 by either once every 8 weeks dosing (2Q8) or as needed dosing with very strict repeat dosing criteria (PRN). Mean gains in visual acuity versus baseline were as shown in Table 2:

TABLE 2

|  | n | Mean change in visual acuity at week 24 versus baseline (letters) | Mean change in visual acuity at week 52 versus baseline (letters) |
|---|---|---|---|
| Laser | 44 | 2.5 | −1.3 |
| VEGFT 0.5 mg monthly (0.5Q4) | 44 | 8.6** | 11.0** |
| VEGFT 2 mg monthly (2Q4) | 44 | 11.4** | 13.1** |
| VEGFT 2 mg every 8 weeks[a] (2Q8) | 42 | 8.5** | 9.7** |
| VEGFT 2 mg as needed[a] (PRN) | 45 | 10.3** | 12.0** |

[a]Following three initial monthly doses
**p < 0.01 versus laser

In this study, the visual acuity gains achieved with VEGFT administration at week 24 were maintained or numerically improved up to completion of the study at week 52 in all VEGFT study groups, including 2 mg dosed every other month As demonstrated in the foregoing Examples, the administration of VEGFT to patients suffering from angiogenic eye disorders (e.g., AMD and DME) at a frequency of once every 8 weeks, following a single initial dose and two secondary doses administered four weeks apart, resulted in significant prevention of moderate or severe vision loss or improvements in visual acuity.

Example 6: A Randomized, Multicenter, Double-Masked Trial in Treatment Naïve Patients with Macular Edema Secondary to CRVO In this randomized, double-masked, Phase 3 study, patients received 6 monthly injections of either 2 mg intravitreal VEGFT (114 patients) or sham injections (73 patients). From Week 24 to Week 52, all patients received 2 mg VEGFT as-needed (PRN) according to retreatment criteria. Thus, "sham-treated patients" means patients who received sham injections once every four weeks from Week 0 through Week 20, followed by intravitreal VEGFT as needed from Week 24 through Week 52. "VEGFT-treated patients" means patients who received VEGFT intravitreal injections once every four weeks from Week 0 through Week 20, followed by intravitreal VEGFT as needed from Week 24 through Week 52. The primary endpoint was the proportion of patients who gained ≥15 ETDRS letters from baseline at Week 24. Secondary visual, anatomic, and Quality of Life NEI VFQ-25 outcomes at Weeks 24 and 52 were also evaluated.

At Week 24, 56.1% of VEGFT-treated patients gained ETDRS letters from baseline vs 12.3% of sham-treated patients (P<0.0001). Similarly, at Week 52, 55.3% of VEGFT-treated patients gained letters vs 30.1% of sham-treated patients (P<0.01). At Week 52, VEGFT-treated patients gained a mean of 16.2 letters vs 3.8 letters for sham-treated patients (P<0.001). Mean number of injections was 2.7 for VEGFT-treated patients vs 3.9 for sham-treated patients. Mean change in central retinal thickness was −413.0 μm for VEGFT-treated patients vs −381.8 μm for sham-treated patients. The proportion of patients with ocular neovascularization at Week 24 were 0% for VEGFT-treated patients and 6.8% for sham-treated patients, respectively; at Week 52 after receiving VEGFT PRN, proportions were 0% and 6.8% for VEGFT-treated and sham-treated. At Week 24, the mean change from baseline in the VFQ-25 total score was 7.2 vs 0.7 for the VEGFT-treated and sham-treated groups; at Week 52, the scores were 7.5 vs 5.1 for the VEGFT-treated and sham-treated groups.

This Example confirms that dosing monthly with 2 mg intravitreal VEGFT injection resulted in a statistically significant improvement in visual acuity at Week 24 that was maintained through Week 52 with PRN dosing compared with sham PRN treatment. VEGFT was generally well tolerated and had a generally favorable safety profile.

Example 7: Dosing Regimens

Specific, non-limiting examples of dosing regimens within the scope of the present invention are as follows:

VEGFT 2 mg (0.05 mL) administered by intravitreal injection once every 4 weeks (monthly).

VEGFT 2 mg (0.5 mL) administered by intravitreal injection once every 4 weeks for the first 8 weeks, followed by 2 mg (0.05 mL) via intravitreal injection once every 8 weeks.

VEGFT 2 mg (0.5 mL) administered by intravitreal injection once every 4 weeks for the first 8 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 8 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 12 weeks, followed by 2 mg (0.05 mL) via intravitreal injection once every 8 weeks.

VEGFT 2 mg (0.5 mL) administered by intravitreal injection once every 4 weeks for the first 12 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 12 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 16 weeks, followed by 2 mg (0.05 mL) via intravitreal injection once every 8 weeks.

VEGFT 2 mg (0.5 mL) administered by intravitreal injection once every 4 weeks for the first 16 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 16 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 20 weeks, followed by 2 mg (0.05 mL) via intravitreal injection once every 8 weeks.

VEGFT 2 mg (0.5 mL) administered by intravitreal injection once every 4 weeks for the first 20 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 20 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 24 weeks, followed by 2 mg (0.05 mL) via intravitreal injection once every 8 weeks.

VEGFT 2 mg (0.5 mL) administered by intravitreal injection once every 4 weeks for the first 24 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 24 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 28 weeks, followed by 2 mg (0.05 mL) via intravitreal injection once every 8 weeks.

VEGFT 2 mg (0.5 mL) administered by intravitreal injection once every 4 weeks for the first 28 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 28 weeks, followed by 2 mg (0.05 mL) via intravitreal injection administered pro re nata (PRN) based on visual and/or anatomical outcomes (as assessed by a physician or other qualified medical professional).

VEGFT 2 mg (0.05 mL) administered by intravitreal injection as a single initial dose, followed by additional doses administered pro re nata (PRN) based on visual and/or anatomical outcomes (as assessed by a physician or other qualified medical professional).

Variations on the above-described dosing regimens would be appreciated by persons of ordinary skill in the art and are also within the scope of the present invention. For example, the amount of VEGFT and/or volume of formulation administered to a patient may be varied based on patient characteristics, severity of disease, and other diagnostic assessments by a physician or other qualified medical professional.

Any of the foregoing administration regimens may be used for the treatment of, e.g., age-related macular degeneration (e.g., wet AMD, exudative AMD, etc.), retinal vein occlusion (RVO), central retinal vein occlusion (CRVO; e.g., macular edema following CRVO), branch retinal vein occlusion (BRVO), diabetic macular edema (DME), choroidal neovascularization (CNV; e.g., myopic CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, etc.

SEQUENCES

SEQ ID NO: 1 (DNA sequence having 1377 nucleotides):
ATGGTCAGCTACTGGGACACCGGGGTCCTGCTGTGCGCGCTGCTCAGCTG
TCTGCTTCTCACAGGATCTAGTTCCGGAAGTGATACCGGTAGACCTTTCG
TAGAGATGTACAGTGAAATCCCCGAAATTATACACATGACTGAAGGAAGG
GAGCTCGTCATTCCCTGCCGGGTTACGTCACCTAACATCACTGTTACTTT
AAAAAAGTTTCCACTTGACACTTTGATCCCTGATGGAAAACGCATAATCT
GGGACAGTAGAAAGGGCTTCATCATATCAAATGCAACGTACAAAGAAATA
GGGCTTCTGACCTGTGAAGCAACAGTCAATGGGCATTTGTATAAGACAAA
CTATCTCACACATCGACAAACCAATACAATCATAGATGTGGTTCTGAGTC
CGTCTCATGGAATTGAACTATCTGTTGGAGAAAAGCTTGTCTTAAATTGT
ACAGCAAGAACTGAACTAAATGTGGGGATTGACTTCAACTGGGAATACCC
TTCTTCGAAGCATCAGCATAAGAAACTTGTAAACCGAGACCTAAAAACCC
AGTCTGGGAGTGAGATGAAGAAATTTTTGAGCACCTTAACTATAGATGGT
GTAACCCGGAGTGACCAAGGATTGTACACCTGTGCAGCATCCAGTGGGCT
GATGACCAAGAAGAACAGCACATTTGTCAGGGTCCATGAAAAGGACAAAA
CTCACACATGCCCACCGTGCCCAGCACCTGAACTCCTGGGGGGACCGTCA
GTCTTCCTCTTCCCCCCAAAACCCAAGGACACCCTCATGATCTCCCGGAC
CCCTGAGGTCACATGCGTGGTGGTGGACGTGAGCCACGAAGACCCTGAGG
TCAAGTTCAACTGGTACGTGGACGGCGTGGAGGTGCATAATGCCAAGACA
AAGCCGCGGGAGGAGCAGTACAACAGCACGTACCGTGTGGTCAGCGTCCT
CACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGA
TGAGCTGACCAAGAACCAGGTCAGCCTGACCTGCCTGGTCAAAGGCTTCT
ATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCT
CTACAGCAAGCTCACCGTGGACAAGAGCAGGTGGCAGCAGGGGAACGTCT
TCTCATGCTCCGTGATGCATGAGGCTCTGCACAACCACTACACGCAGAAG
AGCCTCTCCCTGTCTCCGGGTAAATGA SEQ ID NO: 2 (polypeptide sequence having 458 amino acids):
MVSYWDTGVLLCALLSCLLLTGSSSGSDTGRPFVEMYSEIPEIIHMTEGR
ELVIPCRVTSPNITVTLKKFPLDTLIPDGKRIIWDSRKGFIISNATYKEI
GLLTCEATVNGHLYKTNYLTHRQTNTIIDVVLSPSHGIELSVGEKLVLNC
TARTELNVGIDFNWEYPSSKHQHKKLVNRDLKTQSGSEMKKFLSTLTIDG
VTRSDQGLYTCAASSGLMTKKNSTFVRVHEKDKTHTCPPCPAPELLGGPS
VFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQK
SLSLSPGK The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of treating an angiogenic eye disorder in a patient in need thereof comprising sequentially administering to the patient a single initial dose of 2 mg of aflibercept, followed by two secondary doses of 2 mg of aflibercept followed by one or more tertiary doses of 2 mg of aflibercept;
   wherein each secondary dose is administered to the patient by intravitreal injection approximately 4 weeks following the immediately preceding dose; and
   wherein each tertiary dose is administered on an as needed or pro re nata (PRN) basis, based on visual or anatomic outcomes as assessed by a qualified medical professional;
   wherein the patient achieves a gain in visual acuity within 52 weeks following the initial dose.

2. The method of claim 1 wherein the patient gains at least 8 letters Best Corrected Visual Acuity (BCVA) as measured by Early Treatment Diabetic Retinopathy Study (ETDRS) letter score.

3. The method of claim 2 wherein the patient achieves the gain in visual acuity within 24 weeks following the initial dose.

4. The method of claim 1 wherein the patient gains at least 9 letters Best Corrected Visual Acuity (BCVA) as measured by Early Treatment Diabetic Retinopathy Study (ETDRS) letter score.

5. The method of claim 4 wherein the patient achieves the gain in visual acuity within 24 weeks following the initial dose.

6. The method of claim 1 wherein the patient gains at least 10 letters Best Corrected Visual Acuity (BCVA) as measured by Early Treatment Diabetic Retinopathy Study (ETDRS) letter score.

7. The method of claim 6 wherein the aflibercept is formulated as an isotonic solution.

8. The method of claim 7 wherein the isotonic solution contains a sugar.

9. The method of claim 6 wherein the aflibercept is formulated with a non-ionic surfactant.

10. The method of claim 6 wherein the patient achieves the gain in visual acuity within 24 weeks following the initial dose.

11. The method of claim 10 wherein the aflibercept is formulated as an isotonic solution.

12. The method of claim 11 wherein the isotonic solution contains a sugar.

13. The method of claim 10 wherein the aflibercept is formulated with a non-ionic surfactant.

14. The method of claim 1, wherein each tertiary dose is administered on an as needed or pro re nata (PRN) basis, based on visual and anatomic outcomes as assessed by a qualified medical professional.

15. The method of claim 1, wherein each tertiary dose is administered on an as needed or pro re nata (PRN) basis, based on visual outcomes as assessed by a qualified medical professional.

16. The method of claim 1, wherein each tertiary dose is administered on an as needed or pro re nata (PRN) basis, based on anatomic outcomes as assessed by a qualified medical professional.

17. The method of claim 1, wherein the qualified medical professional is a physician.

18. A method of treating diabetic macular edema in a patient in need thereof comprising sequentially administering to the patient a single initial dose of 2 mg of aflibercept, followed by one or more secondary doses of 2 mg of aflibercept, followed by one or more tertiary doses of 2 mg of aflibercept;
    wherein each secondary dose is administered to the patient by intravitreal injection approximately 4 weeks following the immediately preceding dose; and
    wherein each tertiary dose is administered on an as needed or pro re nata (PRN) basis, based on visual or anatomic outcomes as assessed by a qualified medical professional.

19. The method of claim 18 wherein the patient gains at least 9 letters Best Corrected Visual Acuity (BCVA) as measured by Early Treatment Diabetic Retinopathy Study (ETDRS) letter score within 52 weeks following the initial dose.

20. The method of claim 19 wherein the patient achieves the gain in visual acuity within 24 weeks following the initial dose.

21. The method of claim 18 wherein the patient gains at least 10 letters Best Corrected Visual Acuity (BCVA) as measured by Early Treatment Diabetic Retinopathy Study (ETDRS) letter score within 52 weeks following the initial dose.

22. The method of claim 21 wherein the aflibercept is formulated as an isotonic solution.

23. The method of claim 22 wherein the isotonic solution contains a sugar.

24. The method of claim 21 wherein the aflibercept is formulated with a non-ionic surfactant.

25. The method of claim 21 wherein the patient achieves the gain in visual acuity within 24 weeks following the initial dose.

26. The method of claim 25 wherein the aflibercept is formulated as an isotonic solution.

27. The method of claim 26 wherein the isotonic solution contains a sugar.

28. The method of claim 25 wherein the aflibercept is formulated with a non-ionic surfactant.

29. The method of claim 18 wherein exclusion criteria for the patient include both of:
    (1) active ocular inflammation; and
    (2) active ocular or periocular infection.

30. The method of claim 18 wherein four secondary doses are administered to the patient.

31. The method of claim 18, wherein each tertiary dose is administered on an as needed or pro re nata (PRN) basis, based on visual and anatomic outcomes as assessed by a qualified medical professional.

32. The method of claim 18, wherein each tertiary dose is administered on an as needed or pro re nata (PRN) basis, based on visual outcomes as assessed by a qualified medical professional.

33. The method of claim 18, wherein each tertiary dose is administered on an as needed or pro re nata (PRN) basis, based on anatomic outcomes as assessed by a qualified medical professional.

34. The method of claim 18, wherein the qualified medical professional is a physician.

35. A method of treating age-related macular degeneration in a patient in need thereof comprising sequentially administering to the patient a single initial dose of 2 mg of aflibercept, followed by one or more secondary doses of 2 mg of aflibercept, followed by one or more tertiary doses of 2 mg of aflibercept;
    wherein each secondary dose is administered to the patient by intravitreal injection approximately 4 weeks following the immediately preceding dose; and
    wherein each tertiary dose is administered on an as needed or pro re nata (PRN) basis, based on visual or anatomic outcomes as assessed by a qualified medical professional;
    wherein the method is as effective in achieving a gain in visual acuity as monthly administration of 0.5 mg of ranibizumab by intravitreal injection in human subjects with age-related macular degeneration at 52 weeks following the initial dose.

36. The method of claim 35 wherein only two secondary doses are administered to the patient.

37. The method of claim 35 wherein the gain in visual acuity is measured by Early Treatment Diabetic Retinopathy Study (ETDRS) letter score.

38. The method of claim 35, wherein each tertiary dose is administered on an as needed or pro re nata (PRN) basis, based on visual and anatomic outcomes as assessed by a qualified medical professional.

39. The method of claim 35, wherein each tertiary dose is administered on an as needed or pro re nata (PRN) basis, based on visual outcomes as assessed by a qualified medical professional.

40. The method of claim 35, wherein each tertiary dose is administered on an as needed or pro re nata (PRN) basis, based on anatomic outcomes as assessed by a qualified medical professional.

41. The method of claim 35, wherein the qualified medical professional is a physician.

* * * * *